US007803397B2

(12) United States Patent
Heyes et al.

(10) Patent No.: US 7,803,397 B2
(45) Date of Patent: Sep. 28, 2010

(54) POLYETHYLENEGLYCOL-MODIFIED LIPID COMPOUNDS AND USES THEREOF

(75) Inventors: James Heyes, Vancouver (CA); Ian MacLachlan, Vancouver (CA); Ellen Grace Ambegia, Vancouver (CA)

(73) Assignee: Protiva Biotherapeutics, Inc., Burnaby, British Columbia (CA)

( * ) Notice: Subject to any disclaimer, the term of this patent is extended or adjusted under 35 U.S.C. 154(b) by 0 days.

(21) Appl. No.: 10/942,379

(22) Filed: Sep. 15, 2004

(65) Prior Publication Data

US 2005/0175682 A1     Aug. 11, 2005

Related U.S. Application Data

(60) Provisional application No. 60/503,239, filed on Sep. 15, 2003.

(51) Int. Cl.
*A61K 9/127* (2006.01)
*A61K 31/70* (2006.01)
(52) U.S. Cl. .......................................... 424/450; 514/44
(58) Field of Classification Search ....................... None
See application file for complete search history.

(56) References Cited

U.S. PATENT DOCUMENTS

| | | | |
|---|---|---|---|
| 4,394,448 A | 7/1983 | Szoka, Jr. et al. | |
| 4,438,052 A | 3/1984 | Weder et al. | |
| 4,515,736 A | 5/1985 | Deamer | |
| 4,598,051 A | 7/1986 | Papahadjopoulos et al. | |
| 4,897,355 A | 1/1990 | Eppstein et al. | |
| 5,013,556 A | 5/1991 | Woodle et al. | |
| 5,171,678 A | 12/1992 | Behr et al. | |
| 5,208,036 A | 5/1993 | Eppstein et al. | |
| 5,225,212 A | 7/1993 | Martin et al. | |
| 5,264,618 A | 11/1993 | Felgner et al. | |
| 5,279,833 A | 1/1994 | Rose | |
| 5,283,185 A | 2/1994 | Epand et al. | |
| 5,320,906 A | 6/1994 | Eley et al. | |
| 5,545,412 A | 8/1996 | Eppstein et al. | |
| 5,578,475 A | 11/1996 | Jessee | |
| 5,641,662 A | 6/1997 | Debs et al. | |
| 5,656,743 A | 8/1997 | Busch et al. | |
| 5,703,055 A | 12/1997 | Felgner et al. | |
| 5,705,385 A | 1/1998 | Bally et al. | |
| 5,820,873 A | 10/1998 | Choi et al. | |
| 5,885,613 A | 3/1999 | Holland et al. | |
| 5,976,567 A | 11/1999 | Wheeler et al. | |
| 5,981,501 A | 11/1999 | Wheeler et al. | |
| 6,165,501 A | 12/2000 | Tirosh et al. | |
| 6,284,267 B1 * | 9/2001 | Aneja .......................... | 424/450 |
| 6,287,591 B1 * | 9/2001 | Semple et al. ............... | 424/450 |
| 6,534,484 B1 | 3/2003 | Wheeler et al. | |
| 6,586,410 B1 | 7/2003 | Wheeler et al. | |
| 6,696,424 B1 * | 2/2004 | Wheeler ....................... | 514/44 |
| 6,815,432 B2 | 11/2004 | Wheeler et al. | |
| 6,858,224 B2 | 2/2005 | Wheeler et al. | |

| | | | |
|---|---|---|---|
| 2005/0064595 A1 * | 3/2005 | MacLachlan et al. ....... | 435/458 |

FOREIGN PATENT DOCUMENTS

| | | | |
|---|---|---|---|
| CA | 2 309 727 A1 | 4/1999 | |
| CA | 2 271 582 A1 | 11/1999 | |
| CA | 2 330 741 A1 | 11/1999 | |
| CA | 2 397 016 A1 | 7/2001 | |
| JP | 05-202085 A | * | 10/1993 |
| JP | 06080560 | * | 3/1994 |
| WO | WO 91/16024 A1 | 10/1991 | |
| WO | WO 93/05162 A1 | 3/1993 | |
| WO | WO 93/12240 A1 | 6/1993 | |
| WO | WO 93/12756 A2 | 7/1993 | |
| WO | WO 93/24640 A2 | 12/1993 | |
| WO | WO 93/25673 A1 | 12/1993 | |
| WO | WO 95/02698 A1 | 1/1995 | |
| WO | WO 95/18863 A1 | 7/1995 | |
| WO | WO 95/35301 A1 | 12/1995 | |
| WO | WO 96/02655 A1 | 2/1996 | |
| WO | WO 96/10390 A1 | 4/1996 | |
| WO | WO 96/41873 A1 | 12/1996 | |
| WO | WO 98/51285 A2 | 11/1998 | |
| WO | WO 00/03683 A2 | 1/2000 | |
| WO | WO 00/62813 A2 | 10/2000 | |
| WO | WO 0062813 A2 | * | 10/2000 |
| WO | WO 02/087541 A1 | 11/2002 | |

OTHER PUBLICATIONS

Lawrence et al. Synthesis and aggregation properties of dialkyl polyoxyethylene glycerol ethers. Chemistry and Physics of Lipids (1996), 82(2), 89-100.*

Murahashi et al. Synthesis and evaluation of neoglycolipid for liposome modification. Biol. Pharm. Bull. (1997) vol. 20, No. 6, pp. 704-707.*

JP06080560-1994-English abstract from CAplus.*

Ballas, N. et al., "Liposomes bearing a quaternary ammonium detergent as an efficient vehicle for functional transfer of TMV-RNA into plant protoplasts," *Biochim. Biophys. Acta*, 1998, pp. 8-18, vol. 939.

Barinaga, M., "Step Taken Toward Improved Vectors for Gene Transfer," *Science*, 1994, p. 1326, vol. 266.

Behr, J-P., "Synthetic Gene-Transfer Vectors," *Acc. Chem. Res.* 1993, pp. 274-278, vol. 26.

Brigham, K. et al., "Rapid Communication: In vivo Transfection of Murine Lungs with a Functioning Prokaryotic Gene Using a Liposome Vehicle," *Am. J. Med. Sci.*, 1989, pp. 278-281, vol. 298.

Chonn and Cullis, "Recent advances in liposomal drug-delivery systems," *Current Opinion in Biotechnology*, 1995, pp. 698-708, vol. 6.

(Continued)

*Primary Examiner*—Janet Epps-Smith
(74) *Attorney, Agent, or Firm*—Townsend and Townsend and Crew LLP

(57) ABSTRACT

The present invention provides compositions comprising polytheylyene-dialkyloxypropyl conjugates (PEG-DAA), liposomes, SNALP, and SPLP comprising such compositions, and methods of using such compositions, liposomes, SNALP, and SPLP.

15 Claims, 23 Drawing Sheets

OTHER PUBLICATIONS

Cortesi, R., et al., "Effect of cationic liposome composition on in vitro cytotoxicity and protective effect on carried DNA," *International Journal of Pharmaceutics*, 1996, pp. 69-78, vol. 139.

Crystal, R., "Transfer of Genes to Humans: Early Lessons and Obstacles to Success," *Science*, 1995, pp. 404-410, vol. 270.

Culver K.,, "The First Human Gene Therapy Experiment," *Gene Therapy: A Handbook for Physicians*, 1994, pp. 33-40.

Duzgunes, N., "Membrane Fusion," *Subcellular Biochemistry*, 1985, pp. 195-286, vol. 11.

Dwarki, V.J., et al., "Cationic Liposime-Mediated RNA Transfection," *Methods in Enzymology*, 1993, pp. 644-654, vol. 217.

Enoch, H. et al., "Formation and properties of 1000-Å-diameter, single-bilayer phospholipid vesicles," *Proc. Natl. Acad. Sci. USA*, 1979, pp. 145-149, vol. 76, No. 1.

Felgner, P. et al., "Lipofection: A highly efficient, lipid-mediated DNA-transfection procedure," *Proc. Natl. Acad. Sci. USA*, 1987, pp. 7413-7417, vol. 84.

Felgner, J.H., et al., "Enhanced Gene Delivery and Mechanism Studies with a Novel Series of Cationic Lipid Formulations," *The Journal of Biological Chemistry*, Jan. 1994, pp. 2550-2561, vol. 269, No. 4.

Felgner, J., et al., "Cationic Lipid-Mediated Transfection in Mammalian Cells: "Lipofection"," *J. Tiss. Cult. Meth.*, 1993, pp. 63-68, vol. 15.

Felgner, P.L., et al., "Cationic Liposome Mediated Transfection," *Proc. West. Pharmacol. Soc.*, 1989, pp. 115-121, vol. 32.

Gao, X. et al., "A Novel Cationic Liposome Reagent for Efficient Transfection of Mammalian Cells," *Biochem. Biophys. Res. Comm.*, 1991, pp. 280-285, vol. 179.

Gershon, H. et al., "Mode of Formation and Structural Feature of DNA-Cationic Liposome Complexes Used for Transfection," *Biochemistry*, 1993, pp. 7413-7151, vol. 32.

Guy-Caffey, J., et al., "Novel Polyaminolipids Enhance the Cellular Uptake of Oligonucleotides," *The Journal of Biological Chemistry*, Dec. 1995, pp. 31391-31396, vol. 270, No. 52.

Hawley-Nelson, et al., "LipofectAmine™ Reagent: A New, Higher Efficiency Polycationic Liposome Transfection Reagent," *Focus*, 1993, p. 73-80, vol. 15, No. 3.

Hyde, S., et al., "Correction of the ion transport defect in cystic fibrosis transgenic mice by gene therapy," *Nature*, 1993, pp. 250-256, vol. 362.

Juliano R., and Stamp, D., "The Effect of Particle Size and Charge on the Clearance Rates of Liposomes and Liposome Encapsulated Drugs," *Biochem. Biophys. Res. Commun.*, 1975, pp. 651-658, vol. 63.

Legendre, J.Y. and Szoka, F., "Delivery of Plasmid DNA into Mammalian Cell Lines Using pH-Sensitive Liposomes: Comparison with Cationic Liposomes," *Pharm. Res.*, 1992, pp. 1235-1242, vol. 9, No. 10.

Leventis, R., et al.,, "Interactions of mammalian cells with lipid dispersions containing novel metabolizable cationic amphiphiles," *Biochem. Biophys. Acta*, 1990, p. 124, vol. 1023.

Marshall, Gene Therapy's Growing Pains, *Science*, Aug. 1995, pp. 1050-1055, vol. 269.

Orkin, et al., *NIH Report, Report and Recommendations of the Panel to Assess the NIH Investment in Research on Gene Therapy*, 1995.

Puyal, et al., "A New Cationic Liposome Encapsulating Genetic Material: A Potential Delivery System for Polynucleotides," *Eur. J. Biochem.*, 1995, pp. 697-703, vol. 228.

Stamatatos, L., et al., "Interactions of Cationic Lipid Vesicles with Negatively Charged Phospholipid Vesicles and Biological Membranes," *Biochemistry*, 1988, pp. 3917-3925, vol. 27.

Sawada, K., et al., Microemulsions in supercritical $CO_2$ utilizing the polyethyleneglycol dialkylglycerol and their use for the solubilization of hydrophiles, *Dyes and Pigments*, 2005, pp. 64-74, vol. 65.

Szoka, F. et al., "Comparative Properties and Methods of Preparation of Lipid Vesicles (Liposomes)," *Ann. Rev. Biophys. Bioeng.*, 1980, pp. 467-508, vol. 9.

Szoka, F. et al., "Procedure for preparation of liposomes with large internal aqueous space and high capture by reverse-phase evaporation," *Proc. Natl. Acad. Sci. USA*, 1978, pp. 4194-4198, vol. 75, No. 9.

Van Der Woude, I., et al., "Parameters influencing the introduction of plasmid DNA into cells by the use of synthetic amphiphiles as a carrier system," *Biochimica et Biophysica Acta*, 1995, pp. 34-40, vol. 1240.

Wheeler, J., et al., "Stabilized plasmid-lipid particles: construction and characterization," *Gene Therapy*, 1999, pp. 271-281, vol. 6.

Wilson, R. et al., "Counterion-Induced Condensation of Deoxyribonucleic Acid. A Light-Scattering Study." *Biochemistry*, 1979, pp. 2192-2196, vol. 18.

Woodle, M.C., et al., "Versatility in lipid compositions showing prolonged circulation with sterically stabilized liposomes," *Biochim. Biophys. Acta*, 1992, pp. 193-200, vol. 1105.

Zhu, N., et al., "Systemic Gene Expression After Intravenous DNA Delivery into Adult Mice," *Science*, 1993, pp. 209-211, vol. 261.

Parr et al. "Factors influencing the retention and chemical stability of poly(ethylene glycol)-lipid conjugates incorporated into large unilamellar vesicles," Biochimica et Biophysica Acta, 1994, 1195:21-30.

Song, L.Y. et al. "Characterization of the inhibitory effect of PEG-lipid conjugates on the intracellular delivery of plasmid and antisense DNA mediated by cationic lipid liposomes," Biochimica et Biophysica Acta, 2002, 1558:1-13.

Heyes, James et al., "Cationic lipid saturation influences intracellular delivery of encapsulated nucleic acids," Journal of Controlled Release, 2005, vol. 107, pp. 276-287.

Heyes, James et al., "Synthesis of Novel Cationic Lipids: Effect of Structural Modification on the Efficiency of Gene Transfer," J. Med. Chem., 2002, vol. 45, pp. 99-114.

* cited by examiner

*N*-(2,3-dimyristyloxypropyl) amide PEG₂₀₀₀ methyl ether (PEG-A-DMA)

*N*-(2,3-dimyristyloxypropyl) carbamate PEG₂₀₀₀ methyl ether (PEG-C-DMA)

N-(2,3-dimyristyloxypropyl) succinamide PEG₂₀₀₀ methyl ether (PEG-S-DMA)

Timecourse silencing effect of anti-luc siRNA and pL055 SNALP (PEG-A-DMA) on luciferase gene expression in the tumour after a single iv dose of 50 ug of anti-luc siRNA & 50 ug of pL055 in Neuro-2a tumour bearing male AJ mice Timecourse silencing effect of anti-luc siRNA and pL055 SNALP (PEG-A-DMA) on luciferase gene expression in the tumour after a single iv dose of 50 ug of anti-luc siRNA & 50 ug of pL055 in Neuro-2a tumour bearing male AJ mice Effect on 48hr Luciferase Gene Expression of SPLP Containing 15mol% DODMA with Varying Amounts of PEG-C-DMA (PRO-272)

SEQUENCE LISTING

```
<160> NUMBER OF SEQ ID NOS: 2

<210> SEQ ID NO 1
<211> LENGTH: 21
<212> TYPE: RNA
<213> ORGANISM: Artificial Sequence
<220> FEATURE:
<223> OTHER INFORMATION: Anti-luciferase siRNA sense sequence

<400> SEQUENCE: 1
gauuaugucc gguuauguau u                                             21

<210> SEQ ID NO 2
<211> LENGTH: 21
<212> TYPE: DNA
<213> ORGANISM: Artificial Sequence
<220> FEATURE:
<223> OTHER INFORMATION: Anti-luciferase siRNA target sequence

<400> SEQUENCE: 2
gattatgtcc ggttatgtat t                                             21
```

US 7,803,397 B2

POLYETHYLENEGLYCOL-MODIFIED LIPID COMPOUNDS AND USES THEREOF

CROSS-REFERENCES TO RELATED APPLICATIONS

This patent application claims the benefit of U.S. Patent Application No. 60/503,239, filed on Sep. 15, 2003, and is related to U.S. patent application Ser. No. 10/893,121 which claims the benefit of U.S. Provisional Patent Application Nos. 60/488,144, filed on Jul. 16, 2003, 60/503,279, filed on Sep. 15, 2003, and 60/529,406, filed on Dec. 11, 2003, the teachings of each of which are incorporated herein by reference in their entirety for all purposes.

BACKGROUND OF THE INVENTION

An effective and safe gene delivery system is required for gene therapy to be clinically useful. Viral vectors are relatively efficient gene delivery systems, but suffer from a variety of limitations, such as the potential for reversion to the wild type as well as immune response concerns. As a result, nonviral gene delivery systems are receiving increasing attention (Worgall, et al., *Human Gene Therapy* 8:37-44 (1997); Peeters, et al., *Human Gene Therapy* 7:1693-1699 (1996); Yei, et al., *Gene Therapy* 1:192-200 (1994); Hope, et al., *Molecular Membrane Biology* 15:1-14 (1998)). Plasmid DNA-cationic liposome complexes are currently the most commonly employed nonviral gene delivery vehicles (Felgner, *Scientific American* 276:102-106 (1997); Chonn, et al., *Current Opinion in Biotechnology* 6:698-708 (1995)). However, complexes are large, poorly defined systems that are not suited for systemic applications and can elicit considerable toxic side effects (Harrison, et al., *Biotechniques* 19:816-823 (1995); Huang, et al., *Nature Biotechnology* 15:620-621 (1997); Templeton, et al., *Nature Biotechnology* 15:647-652 (1997); Hofland, et al., *Pharmaceutical Research* 14:742-749 (1997)).

Recent work has shown that plasmid DNA can be encapsulated in small (~70 nm diameter) "stabilized plasmid-lipid particles" (SPLP) that consist of a single plasmid encapsulated within a bilayer lipid vesicle (Wheeler, et al., *Gene Therapy* 6:271-281 (1999)). These SPLPs typically contain the "fusogenic" lipid dioleoylphosphatidyl-ethanolamine (DOPE), low levels of cationic lipid, and are stabilized in aqueous media by the presence of a poly(ethylene glycol) (PEG) coating. SPLP have systemic application as they exhibit extended circulation lifetimes following intravenous (i.v.) injection, accumulate preferentially at distal tumor sites due to the enhanced vascular permeability in such regions, and can mediate transgene expression at these tumor sites. The levels of transgene expression observed at the tumor site following i.v. injection of SPLP containing the luciferase marker gene are superior to the levels that can be achieved employing plasmid DNA-cationic liposome complexes (lipoplexes) or naked DNA. Still, improved levels of expression may be required for optimal therapeutic benefit in some applications (see, e.g., Monck, et al., *J. Drug Targ.* 7:439-452 (2000)).

Typically, both liposomes and SPLPs comprise PEG-lipid derivatives. Typically, PEG-lipids are prepared by derivatization of the polar head group of a diacylglycerophospholipid, such as distearoylphosphatidylethanolamine (DSPE), with PEG. These phospholipids usually contain two fatty acyl chains bonded to the 1- and 2-position of glycerol by ester linkages. Unfortunately, these acyl groups are susceptible to cleavage under acidic or basic conditions. The resulting hydrolytic products, such as analogs of lysophospholipid and glycerophosphate, do not remain associated with the bilayer structure of the liposome or the SPLP. Unfortunately, such dissociation can weaken the integrity of the liposome or SPLP structure, leading to significant leakage of the bioactive agent or drug from the liposome or SPLP and contributing to instability during storage, and thus shortened shelf-life of the liposome or SPLP product. In addition, the loss of these hydrolysis products, such as PEG-lysophospholipid, from the liposome or SPLP negates the benefits otherwise resulting from the presence of the PEG-phospholipid.

Lipid stability is important in the development of liposomal or SPLP drug delivery systems. Therefore, it is desirable to develop PEG-lipids that are less susceptible to hydrolysis, thereby, increasing the circulation longevity of the liposomes or the SPLP. The present invention addresses this and other needs.

SUMMARY OF THE INVENTION

The present invention provides novel polyethyleneglycol-dialkyloxypropyl (PEG-DAA) conjugates that have increased stability over commonly used PEG-lipid conjugates (such as PEG-PE conjugates). The PEG-modified dialkylpropyl conjugates of the present invention enhance the properties of liposomes as well as nucleic acid-lipid particles (e.g., SNALPs and SPLPs) by increasing the circulation longevity or lifetime of the liposome, SNALP, or SPLP. In fact, it has surprisingly been found that the PEG-DAA conjugates of the present invention are more stable than other commonly used PEG-lipid derivatives. As a result of their increased stability, the PEG-DAA conjugates of the present invention increase the circulation longevity or lifetime of the liposome or SPLP and also reduce leakage due to hydrolysis of the fatty acyl chains of the liposome bilayer or the SPLP when other PEG-lipid conjugates are used.

The present invention provides novel PEG-DAA conjugates of Formula I having the following structure:

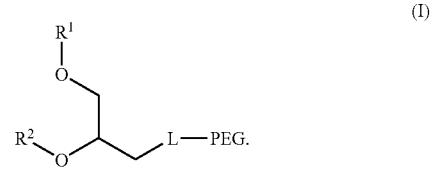

In Formula I, above, "$R^1$ and $R^2$" are independently selected and are alkyl groups having from about 10 to about 20 carbon atoms; PEG is a polyethyleneglycol; and L is a linker moiety (e.g., a non-ester-containing linker moiety or a ester containing linker moiety). Suitable alkyl groups include, but are not limited to, lauryl (C12), myristyl (C14), palmityl (C16), stearyl (C18) and icosyl (C20). In a preferred embodiment; $R^1$ and $R^2$ are the same, i.e., they are both myristyl (C14) or both palmityl (C16) or both stearyl (C18). In a preferred embodiment, the alkyl groups are saturated.

In Formula I, above, "PEG" is a polyethylene glycol having an average molecular weight ranging of about 550 daltons to about 10,000 daltons, more preferably of about 750 daltons to about 5,000 daltons, more preferably of about 1,000 daltons to about 5,000 daltons, more preferably of about 1,500 daltons to about 3,000 daltons and, even more preferably, of about 2,000 daltons, or about 750 daltons. The PEG can be optionally substituted with alkyl, alkoxy, acyl or aryl. In a preferred embodiment, the terminal hydroxyl group is substituted with a methoxy or methyl group. PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In a preferred embodiment, the linker moiety is a non-ester containing linker moiety. As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CCH$_2$CH$_2$C(O)—), succinamidyl (—NHC(O)CH$_2$CH$_2$C(O)NH—), ether, disulphide, etc. as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof.

In Formula I, above, "L" is a non-ester containing linker moiety or an ester containing linker moiety. In a preferred embodiment, L is a non-ester containing linker moiety. Suitable non-ester containing linkers include, but are not limited to, an amido linker moiety, an amino linker moiety, a carbonyl linker moiety, a carbamate linker moiety, a urea linker moiety, an ether linker moiety, a disulphide linker moiety, a succinamidyl linker moiety and combinations thereof. In a preferred embodiment, the non-ester containing linker moiety is a carbamate linker moiety (i.e., a PEG-C-DAA conjugate). In another preferred embodiment, the non-ester containing linker moiety is an amido linker moiety (i.e., a PEG-A-DAA conjugate). In a preferred embodiment, the non-ester containing linker moiety is a succinamidyl linker moiety (i.e., a PEG-S-DAA conjugate).

In another aspect, the present invention provides a liposome comprising a polyethyleneglycol-dialkyloxypropyl (PEG-DAA) conjugate of Formula I. The liposome typically also comprises a cationic lipid and a non-cationic lipid. In some aspects, the liposome further comprises a sterol (e.g., cholesterol). The liposome can be empty or, alternatively, the liposome can further comprise one or more bioactive agents (e.g., a therapeutic product as described herein). Suitable bioactive agents include, but are not limited to, antineoplastic agents, antibiotics, immunomodulators, anti-inflammatory agents and agents acting on the central nervous system. Similarly, suitable bioactive agents include, but are not limited to, peptides, proteins and nucleic acids.

In another aspect the present invention provides a method of delivering a bioactive agent to a cell, the methods comprising contacting the cell with a liposome comprising a PEG-DAA conjugate of Formula I, wherein the bioactive agent is encapsulated in the liposome. Similarly, in another aspect, the present invention provides a method of delivering a bioactive agent to a patient, the method comprising administering to the patient a liposome comprising a PEG-DAA conjugate of Formula I, wherein the bioactive agent is encapsulated in the liposome.

In another aspect, the present invention provides a nucleic acid-lipid particle, the nucleic acid-lipid particle comprising: a nucleic acid; a cationic lipid; a non-cationic lipid; and a PEG-DAA conjugate of Formula I. In some aspects, the nucleic acid-lipid particle further comprises a sterol (e.g., cholesterol).

In yet another aspect, the present invention provides a method of introducing a nucleic acid into a cell, the method comprising contacting the cell with a nucleic acid-lipid particle comprising a cationic lipid, a non-cationic lipid, a PEG-DAA conjugate of Formula I, and a nucleic acid.

Other features, objects and advantages of the invention and its preferred embodiments will become apparent from the detailed description, examples, claims and figures that follow.

DETAILED DESCRIPTION OF THE INVENTION

I. Introduction

Figure 1:
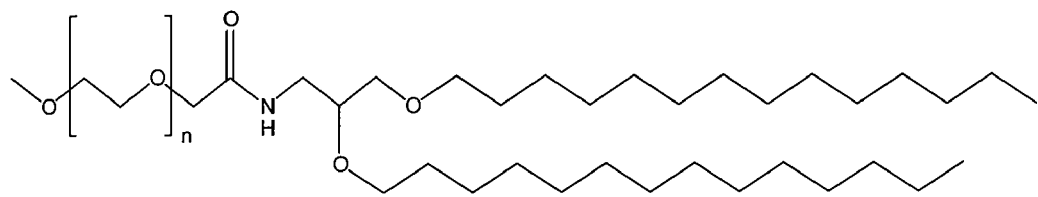
FIG. 1 illustrates the structures of two exemplary PEG-dialkyloxypropyl derivatives, i.e., N-(2,3-dimyristyloxypropyl) carbamate PEG$_{2000}$ methyl ether (i.e., PEG-C-DMA), N-(2,3-dimyristyloxypropyl)amide PEG$_{2000}$ methyl ether (i.e., PEG-A-DMA), and N-(2,3-dimyristyloxypropyl) succinamide PEG$_{2000}$ methyl ether (i.e., PEG-S-DMA).
Figure 1:
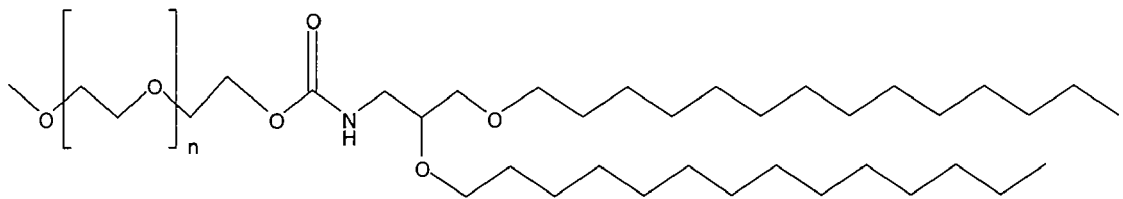
Figure 1:
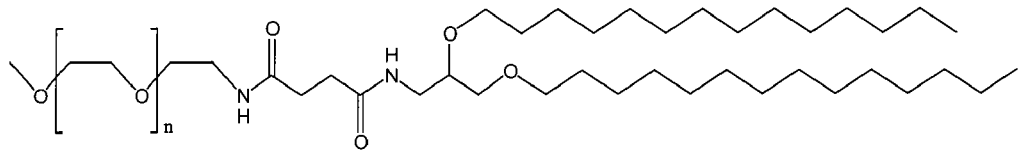

The present invention provides novel polyethyleneglycol-dialkyloxypropyl (PEG-DAA) conjugates that have increased stability over commonly used PEG-lipid conjugates (such as PEG-PE conjugates). The PEG-modified dialkylpropyl conjugates of the present invention enhance the properties of liposomes as well as nucleic acid-lipid particles (e.g., SNALPs and SPLPs) by increasing the circulation longevity or lifetime of the liposome, SNALP, or SPLP. In fact, it has surprisingly been found that the PEG-DAA conjugates comprising a PEG conjugated to a DAA via a linker are more stable than other commonly used PEG-lipid derivatives. In particular, it has surprisingly been found the use of a non-ester containing linker moiety results in PEG-DAA conjugates that have increased stability compared to commonly used PEG-lipid conjugates (e.g., PEG-PE conjugates). As a result of their increased stability, the PEG-DAA conjugates of the present invention increase the circulation longevity or lifetime of the liposome, SNALP, or SPLP and also reduce leakage due to hydrolysis of the fatty acyl chains of the liposome bilayer, SNALP, or SPLP when other PEG-lipid conjugates are used.

II. Definitions

The term "dialkyloxypropyl" refers to a compound having 2-alkyl chains, $R^1$ and $R^2$, both of which have independently between 2 and 30 carbons. The alkyl groups can be saturated or have varying degrees of unsaturation. Dialkyloxypropyls have the following general formula:

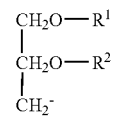

The term "PEG" refers to a polyethylene glycol, a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, for example, the following: monomethoxypolyethylene glycol (MePEG-OH), monomethoxypolyethylene glycol-succinate (MePEG-S), monomethoxypolyethylene glycol-succinimidyl succinate (MePEG-S—NHS), monomethoxypolyethylene glycol-amine (MePEG-$NH_2$), monomethoxypolyethylene glycol-tresylate (MePEG-TRES), and monomethoxypolyethylene glycol-imidazolyl-carbonyl (MePEG-IM). In addition, the example provide a protocol for synthesizing monomethoxypolyethyleneglycol-acetic acid (MePEG-$CH_2$COOH), which is particularly useful for preparing the PEG-DAA conjugates of the present invention.

In a preferred embodiment, the PEG is a polyethylene glycol with an average molecular weight of about 550 to about 10,000 daltons and is optionally substituted by alkyl, alkoxy, acyl or aryl. In a preferred embodiment, the PEG is substituted with methyl at the terminal hydroxyl position. In another preferred embodiment, the PEG has an average molecular weight of about 750 to about 5,000 daltons, more preferably, of about 1,000 to about 5,000 daltons, more preferably about 1,500 to about 3,000 daltons and, even more preferably, of about 2,000 daltons or of about 750 daltons. The PEG can be optionally substituted with alkyl, alkoxy, acyl or aryl. In a preferred embodiment, the terminal hydroxyl group is substituted with a methoxy or methyl group.

As used herein, a PEG-DAA conjugate refers to a polyethylene glycol conjugated to a dialkyloxypropyl. The PEG may be directly conjugated to the DAA or may be conjugated to the DAA via a linker moiety. Suitable linker moieties include nonester-containing linker moieties and ester containing linker moieties.

As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CCH$_2$CH$_2$C(O)—), succinamidyl (—NHC(O)CH$_2$CH$_2$C(O)NH—), ether, disulphide, etc. as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof.

The term "lipid" refers to a group of organic compounds that include, but are not limited to, esters of fatty acids and are characterized by being insoluble in water, but soluble in many organic solvents. They are usually divided into at least three classes: (1) "simple lipids" which include fats and oils as well as waxes; (2) "compound lipids" which include phospholipids and glycolipids; (3) "derived lipids" such as steroids.

"Lipid vesicle" refers to any lipid composition that can be used to deliver a compound including, but not limited to, liposomes, wherein an aqueous volume is encapsulated by an amphipathic lipid bilayer; or wherein the lipids coat an interior comprising a large molecular component, such as a plasmid comprising an interfering RNA sequence, with a reduced aqueous interior; or lipid aggregates or micelles, wherein the encapsulated component is contained within a relatively disordered lipid mixture.

As used herein, "lipid encapsulated" can refer to a lipid formulation that provides a compound with full encapsulation, partial encapsulation, or both. In a preferred embodiment, the nucleic acid is fully encapsulated in the lipid formulation (e.g., to form an SPLP, pSPLP, SNALP, or other nucleic-acid lipid particle). Nucleic-acid lipid particles and their method of preparation are disclosed in U.S. Pat. No. 5,976,567, U.S. Pat. No. 5,981,501 and PCT Patent Publication No. WO 96/40964.

As used herein, the term "SNALP" refers to a stable nucleic acid lipid particle, including SPLP. A SNALP represents a vesicle of lipids coating a reduced aqueous interior comprising a nucleic acid (e.g., ssDNA, dsDNA, ssRNA, dsRNA, siRNA, or a plasmid, including plasmids from which an interfering RNA is transcribed). As used herein, the term "SPLP" refers to a nucleic acid lipid particle comprising a nucleic acid (e.g., a plasmid) encapsulated within a lipid vesicle. SNALPs and SPLPs typically contain a cationic lipid, a non-cationic lipid, and a lipid that prevents aggregation of the particle (e.g., a PEG-lipid conjugate). SNALPs and SPLPs have systemic application as they exhibit extended circulation lifetimes following intravenous (i.v.) injection, accumulate at distal sites (e.g., sites physically separated from the administration site and can mediate expression of the transfected gene at these distal sites. SPLPs include "pSPLP" which comprise an encapsulated condensing agent-nucleic acid complex as set forth in WO 00/03683.

The term "vesicle-forming lipid" is intended to include any amphipathic lipid having a hydrophobic moiety and a polar head group, and which by itself can form spontaneously into bilayer vesicles in water, as exemplified by most phospholipids.

The term "vesicle-adopting lipid" is intended to include any amphipathic lipid that is stably incorporated into lipid bilayers in combination with other amphipathic lipids, with its hydrophobic moiety in contact with the interior, hydrophobic region of the bilayer membrane, and its polar head group moiety oriented toward the exterior, polar surface of the membrane. Vesicle-adopting lipids include lipids that on their own tend to adopt a nonlamellar phase, yet which are capable of assuming a bilayer structure in the presence of a bilayer-stabilizing component. A typical example is DOPE (dioleoylphosphatidylethanolamine). Bilayer stabilizing components include, but are not limited to, conjugated lipids that inhibit aggregation of the SNALPs, polyamide oligomers (e.g., ATTA-lipid derivatives), peptides, proteins, detergents, lipid-derivatives, PEG-lipid derivatives such as PEG coupled to dialkyloxypropyls, PEG coupled to diacylglycerols, PEG coupled to phosphatidyl-ethanolamines, and PEG conjugated to ceramides (see, U.S. Pat. No. 5,885,613, which is incorporated herein by reference). PEG can be conjugated directly to the lipid or may be linked to the lipid via a linker moiety. Any linker moiety suitable for coupling the PEG to a lipid can be used including, e.g., non-ester containing linker moieties and ester-containing linker moieties.

The term "amphipathic lipid" refers, in part, to any suitable material wherein the hydrophobic portion of the lipid material orients into a hydrophobic phase, while the hydrophilic portion orients toward the aqueous phase. Amphipathic lipids are usually the major component of a lipid vesicle. Hydrophilic characteristics derive from the presence of polar or charged groups such as carbohydrates, phosphate, carboxylic, sulfato, amino, sulfhydryl, nitro, hydroxy and other like groups. Hydrophobicity can be conferred by the inclusion of apolar groups that include, but are not limited to, long chain saturated and unsaturated aliphatic hydrocarbon groups and such groups substituted by one or more aromatic, cycloaliphatic or heterocyclic group(s). Examples of amphipathic compounds include, but are not limited to, phospholipids, aminolipids and sphingolipids. Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine or dilinoleoylphosphatidylcholine. Other compounds lacking in phosphorus, such as sphingolipid, glycosphingolipid families, diacylglycerols and .beta.-acyloxyacids, are also within the group designated as amphipathic lipids. Additionally, the amphipathic lipid described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides and diacylglycerols.

The term "noncationic lipid" refers to any neutral lipid as described above as well as anionic lipids.

The term "anionic lipid" refers to any lipid that is negatively charged at physiological pH. These lipids include, but are not limited to, phosphatidylglycerol, cardiolipin, diacylphosphatidylserine, diacylphosphatidic acid, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The term "cationic lipid" refers to any of a number of lipid species that carry a net positive charge at a selected pH, such as physiological pH. Such lipids include, but are not limited to, N,N-dioleyl-N,N-dimethylammonium chloride ("DODAC"); N-(2,3-dioleyloxy)propyl)-N,N,N-trimethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 3-(N-(N',N'-dimethylaminoethane)-carbamoyl)cholesterol ("DC-Chol") and N-(1,2-dimyristyloxyprop-3-yl)-N,N-dimethyl-N-hydroxyethyl ammonium bromide ("DMRIE"). The following lipids are cationic and have a positive charge at below physiological pH: DODAP, DODMA, DMDMA and the like.

The term "hydrophobic lipid" refers to compounds having apolar groups that include, but are not limited to, long chain saturated and unsaturated aliphatic hydrocarbon groups and such groups optionally substituted by one or more aromatic, cycloaliphatic or heterocyclic group(s). Suitable examples include, but are not limited to, diacylglycerol, dialkylglycerol, N-N-dialkylamino, 1,2-diacyloxy-3-aminopropane and 1,2-dialkyl-3-aminopropane.

The term "fusogenic" refers to the ability of a liposome, an SNALP or other drug delivery system to fuse with membranes of a cell. The membranes can be either the plasma membrane or membranes surrounding organelles, e.g., endosome, nucleus, etc.

The term "diacylglycerol" refers to a compound having 2-fatty acyl chains, $R^1$ and $R^2$, both of which have independently between 2 and 30 carbons bonded to the 1- and 2-position of glycerol by ester linkages. The acyl groups can be saturated or have varying degrees of unsaturation. Diacylglycerols have the following general formula:

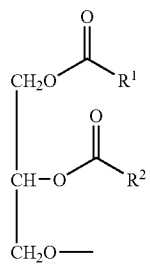

The term "ATTA" or "polyamide" refers to, but is not limited to, compounds disclosed in U.S. Pat. Nos. 6,320,017 and 6,586,559, both of which are incorporated herein by reference. These compounds include a compound having the formula

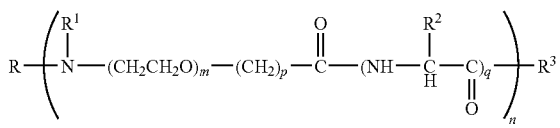

wherein: R is a member selected from the group consisting of hydrogen, alkyl and acyl; $R^1$ is a member selected from the group consisting of hydrogen and alkyl; or optionally, R and $R^1$ and the nitrogen to which they are bound form an azido moiety; $R^2$ is a member of the group selected from hydrogen, optionally substituted alkyl, optionally substituted aryl and a side chain of an amino acid; $R^3$ is a member selected from the group consisting of hydrogen, halogen, hydroxy, alkoxy, mercapto, hydrazino, amino and $NR^4R^5$, wherein $R^4$ and $R^5$ are independently hydrogen or alkyl; n is 4 to 80; m is 2 to 6; p is 1 to 4; and q is 0 or 1. It will be apparent to those of skill in the art that other polyamides can be used in the compounds of the present invention.

The term "nucleic acid" or "polynucleotide" refers to a polymer containing at least two deoxyribonucleotides or ribonucleotides in either single- or double-stranded form. Nucleic acids include nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). Unless specifically limited, the terms encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides. DNA may be in the form of antisense, plasmid DNA, parts of a plasmid DNA, pre-condensed DNA, product of a polymerase chain reaction (PCR), vectors (P1, PAC, BAC, YAC, artificial chromosomes), expression cassettes, chimeric sequences, chromosomal DNA, or derivatives of these groups. The term nucleic acid is used interchangeably with gene, cDNA, mRNA encoded by a gene, and an interfering RNA molecule.

The term "gene" refers to a nucleic acid (e.g., DNA or RNA) sequence that comprises partial length or entire length coding sequences necessary for the production of a polypeptide or a polypeptide precursor (e.g., polypeptides or polypeptide preursors from hepatitis virus A, B, C, D, E, or G; or herpes simplex virus).

"Gene product," as used herein, refers to a product of a gene such as an RNA transcript, including, e.g., mRNA.

III. Polyethyleneglycol-Modified Dialkyloxypropyl (PEG-DAA) Conjugates

The present invention provides novel polyethyleneglycol-dialkyloxypropyl (PEG-DAA) conjugates that have increased stability over commonly used PEG-lipid conjugates (such as PEG-PE conjugates). More particularly, the present invention provides novel PEG-DAA conjugates of Formula I having the following structure:

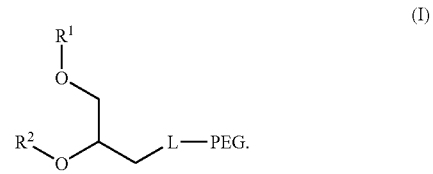

In Formula I, above, $R^1$ and $R^2$ are independently selected and are alkyl groups having from about 10 to about 20 carbon atoms. The alkyl groups can be saturated or unsaturated. Suitable alkyl groups include, but are not limited to, lauryl (C12), myristyl (C14), palmityl (C 16), stearyl (C18) and icosyl (C20). In one embodiment, $R^1$ and $R^2$ are both the same, i.e., $R^1$ and $R^2$ are both myristyl (C14) or both stearyl (C18), etc. In another embodiment, $R^1$ and $R^2$ are different, i.e., $R^1$ is myristyl (C14) and $R^2$ is stearyl (C18). In a preferred embodiment, the PEG-DAA conjugates of the present invention are symmetrical, i.e., $R^1$ and $R^2$ are both the same.

In Formula I, above, PEG is a polyethylene glycol, a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, for example, the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH$_2$), monomethoxypolyethylene glycol-tresylate (MePEG-TRES), and monomethoxypolyethylene glycol-imidazolyl-carbonyl (MePEG-IM). In addition, the example provide a protocol for synthesizing monomethoxypolyethyleneglycol-acetic acid (MePEG-CH$_2$COOH), which is particularly useful for preparing the PEG-DAA conjugates of the present invention.

In a preferred embodiment, the PEG is a polyethylene glycol with an average molecular weight of about 550 to about 10,000 daltons and is optionally substituted by alkyl, alkoxy, acyl or aryl. In a preferred embodiment, the PEG is substituted with methyl at the terminal hydroxyl position. In another preferred embodiment, the PEG has an average molecular weight of about 750 to about 5,000 daltons, more preferably, of about 1,000 to about 5,000 daltons, more preferably about 1,500 to about 3,000 daltons and, even more preferably, of about 2,000 daltons or of about 750 daltons.

In Formula I, above, "L" is a non-ester containing linker moiety or an ester containing linker moiety. In a preferred embodiment, L is a non-ester containing linker moiety, i.e., a linker moiety that does not contain a carboxylic ester bond (—OC(O)—). Suitable non-ester containing linkers include, but are not limited to, an amido linker moiety, an amino linker moiety, a carbonyl linker moiety, a carbamate linker moiety, a urea linker moiety, an ether linker moiety, a disulphide linker moiety, a succinamidyl linker moiety, a succinyl linker moiety, and combinations thereof. In a preferred embodiment, the non-ester containing linker moiety is a carbamate linker moiety (i.e., a PEG-C-DAA conjugate). In another preferred embodiment, the non-ester containing linker moiety is an amido linker moiety (i.e., a PEG-A-DAA conjugate). In a preferred embodiment, the non-ester containing linker moiety is a succinamidyl linker moiety (i.e., a PEG-S-DAA conjugate).

In other embodiments, L is an ester containing linker moiety. Suitable ester containing linker moieties include, e.g., carbonate (—OC(O)O—), succinoyl, phosphate esters (—O—(O)POH—O—), sulfonate esters, and combinations thereof.

The PEG-DAA conjugates of the present invention are synthesized using standard techniques and reagents known to those of skill in the art. It will be recognized that the PEG-DAA conjugates of the present invention will contain various amide, amine, ether, thio, carbamate and urea linkages. Those of skill in the art will recognize that methods and reagents for forming these bonds are well known and readily available. See, e.g., March, ADVANCED ORGANIC CHEMISTRY (Wiley 1992), Larock, COMPREHENSIVE ORGANIC TRANSFORMATIONS (VCH 1989); and Furniss, VOGEL'S TEXTBOOK OF PRACTICAL ORGANIC CHEMISTRY 5th ed. (Longman 1989). It will also be appreciated that any functional groups present may require protection and deprotection at different points in the synthesis of the PEG-DAA conjugates of the present invention. Those of skill in the art will recognize that such techniques are well known. See, e.g., Green and Wuts, PROTECTIVE GROUPS IN ORGANIC SYNTHESIS (Wiley 1991).

A general sequence of reactions for forming the PEG-DAA conjugates of the present invention is set forth in Example Section below. The examples provide synthesis schemes for preparing PEG-A-DMA, PEG-C-DMA and PEG-S-DMA conjugates of the present invention. Using similar protocols, one of skill in the art can readily generate the other PEG-DAA conjugates of the present invention.

In addition to the foregoing, it will be readily apparent to those of skill in the art that other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses, such as hydroxymethylcellulose or hydroxyethylcellulose.

IV. SPLPs and SNALPs Containing PEG-DAA Conjugates

In one embodiment, the present invention provides stabilized nucleic acid-lipid particles (e.g., SPLPs and SNALPs) and other lipid-based carrier systems containing polyethyleneglycol (PEG)-dialkyloxypropyl (DAA) conjugates, i.e., PEG-DAA conjugates. The lipid-nucleic acid particles of the present invention typically comprise a nucleic acid, a cationic lipid, a non-cationic lipid and a PEG-DAA conjugate. The cationic lipid typically comprises from about 2% to about 60% of the total lipid present in said particle, preferably from about 5% to about 45% of the total lipid present in said particle. In certain preferred embodiments, the cationic lipid comprises from about 5% to about 15% of the total lipid present in said particle. In other preferred embodiments, the cationic lipid comprises from about 40% to about 50% of the total lipid present in said particle. The non-cationic lipid typically comprises from about 5% to about 90% of the total lipid present in said particle, preferably from about 20% to about 85% of the total lipid present in said particle. The PEG-DAA conjugate typically comprises from 1% to about 20% of the total lipid present in said particle, preferably from 2% to about 15% of the total lipid present in said particle, and more preferably from about 4% to about 10% of the total lipid present in said particle. The nucleic acid-lipid particles of the present invention may further comprise cholesterol. If present, the cholesterol typically comprises from about 10% to about 60% of the total lipid present in said particle, preferably the cholesterol comprises from about 20% to about 45% of the total lipid present in said particle. It will be readily apparent to one of skill in the art that the proportions of the components of the nucleic acid-lipid particles may be varied, e.g., using the ERP assay described in the Example section. For example for systemic delivery, the cationic lipid may comprise from about 5% to about 15% of the total lipid present in said particle and for local or regional delivery, the cationic lipid comprises from about 40% to about 50% of the total lipid present in said particle.

The SPLPs and SNALPs of the present invention typically have a mean diameter of less than about 150 nm and are substantially nontoxic. In addition, the nucleic acids when present in the SPLPs and SNALPs of the present invention are resistant to aqueous solution to degradation with a nuclease. SPLPs and SNALPs and their method of preparation are disclosed in U.S. Pat. No. 5,976,567, U.S. Pat. No. 5,981,501 and PCT Patent Publication No. WO 96/40964, the teachings of all of which are incorporated herein by reference.

Various suitable cationic lipids may be used in the present invention, either alone or in combination with one or more other cationic lipid species or non-cationic lipid species.

Cationic lipids that are useful in the present invention can be any of a number of lipid species which carry a net positive charge at a selected pH, such as physiological pH. Suitable cationic lipids include, but are not limited to, DODAC, DOTMA, DDAB, DOTAP, DOSPA, DOGS, DC-Chol and DMRIE, or combinations thereof. A number of these cationic lipids and related analogs, which are also useful in the present invention, have been described in co-pending U.S. Ser. No. 08/316,399; U.S. Pat. Nos. 5,208,036, 5,264,618, 5,279,833 and 5,283,185, the disclosures of which are incorporated herein by reference. Additionally, a number of commercial preparations of cationic lipids are available and can be used in the present invention. These include, for example, LIPOFEC-TIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic liposomes comprising DOGS from Promega Corp., Madison, Wis., USA).

The noncationic lipids used in the present invention can be any of a variety of neutral uncharged, zwitterionic or anionic lipids capable of producing a stable complex. They are preferably neutral, although they can alternatively be positively or negatively charged. Examples of noncationic lipids useful in the present invention include: phospholipid-related materials, such as lecithin, phosphatidylethanolamine, lysolecithin, lysophosphatidylethanolamine, phosphatidylserine, phosphatidylinositol, sphingomyelin, cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal). Noncationic lipids or sterols such as cholesterol may be present. Additional nonphosphorous containing lipids are, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide and the like, diacylphosphatidylcholine, diacylphosphatidylethanolamine, ceramide, sphingomyelin, cephalin, and cerebrosides. Other lipids such as lysophosphatidylcholine and lysophosphatidylethanolamine may be present. Noncationic lipids also include polyethylene glycol-based polymers such as PEG 2000, PEG 5000 and polyethylene glycol conjugated to phospholipids or to ceramides (referred to as PEG-Cer), as described in co-pending U.S. Ser. No. 08/316,429, incorporated herein by reference.

In preferred embodiments, the noncationic lipids are diacylphosphatidylcholine (e.g., distearoylphosphatidylcholine, dioleoylphosphatidylcholine, dipalmitoylphosphatidylcholine and dilinoleoylphosphatidylcholine), diacylphosphatidylethanolamine (e.g., dioleoylphosphatidylethanolamine and palmitoyloleoylphosphatidylethanolamine), ceramide or sphingomyelin. The acyl groups in these lipids are preferably acyl groups derived from fatty acids having $C_{10}$-$C_{24}$ carbon chains. More preferably the acyl groups are lauroyl, myristoyl, palmitoyl, stearoyl or oleoyl. In particularly preferred embodiments, the noncationic lipid will be cholesterol, 1,2-sn-dioleoylphosphatidylethanolamine, or egg sphingomyelin (ESM).

In addition to cationic and non-cationic lipids, the SPLPs of the present invention comprise a polyethyleneglycol-dialkyloxypropyl conjugate, i.e., a PEG-DAA conjugate. The term "dialkyloxypropyl" refers to a compound having 2-alkyl chains, $R^1$ and $R^2$, both of which have independently between 2 and 30 carbons. The alkyl groups can be saturated or have varying degrees of unsaturation. Dialkyloxypropyls have the following general formula:

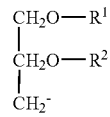

In a presently preferred embodiment, the PEG-DAA conjugate is a dilauryloxypropyl (C12)-PEG conjugate, dimyristyloxypropyl (C14)-PEG conjugate, a dipalmitoyloxypropyl (C16)-PEG conjugate or a disteryloxypropyl (C18)-PEG conjugate. Those of skill in the art will readily appreciate that other dialkyloxypropyls can be used in the PEG-DAA conjugates of the present invention.

In one preferred embodiment, the PEG-DAA conjugate has the following formula:

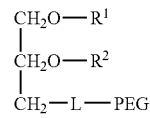

I

In Formula I, $R^1$ and $R^2$ are independently selected and are long-chain alkyl groups having from about 10 to about 22 carbon atoms. The long-chain alkyl groups can be saturated or unsaturated. Suitable alkyl groups include, but are not limited to, lauryl (C12), myristyl (C14), palmityl (C16), stearyl (C18) and icosyl (C20). In preferred embodiments, $R^1$ and $R^2$ are the same, i.e., $R^1$ and $R^2$ are both myristyl (i.e., dimyristyl), $R^1$ and $R^2$ are both stearyl (i.e., distearyl), etc. In Formula I, PEG is a polyethylene glycol having an average molecular weight of from about 550 to about 8,500 daltons. In a preferred embodiment, the PEG has an average molecular weight of from about 1,000 to about 5,000 daltons, more preferably, from about 1,000 to about 3,000 daltons and, even more preferably, of about 2,000 daltons or of about 750 daltons. The PEG can be optionally substituted by an alkyl, alkoxy, acyl or aryl group.

In Formula I, L is a linker moiety (e.g., a non-ester containing linker moiety or an ester containing linker moiety). Any linker moiety suitable for coupling the PEG to the dialkyloxypropyl backbone can be used. In a preferred embodiment, L is a non-ester containing linker moiety, i.e., a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), succinyl (—(O)CCH$_2$CH$_2$(O)—), a succinamidyl, ether, disulphide, and combinations thereof. In a preferred embodiment, the non-ester containing linker moiety is a carbamate linker moiety (i.e., a PEG-C-DAA conjugate). In another preferred embodiment, the non-ester containing linker moiety is an amido linker moiety (i.e., a PEG-A-DAA conjugate). In a preferred embodiment, the non-ester containing linker moiety is a succinamidyl linker moiety (i.e., a PEG-S-DAA conjugate).

In other embodiments, L is an ester containing linker moiety. Suitable ester containing linker moieties include, e.g., carbonate (—OC(O)O—), succinoyl, phosphate esters (—O—(O)POH—O—), sulfonate esters, and combinations thereof.

It has surprisingly been found that PEG-DAA conjugates are particularly useful for the nucleic acid-lipid particles (e.g., SNALPS and SPLP's) of the present invention. PEG-DAA conjugates have multiple advantages over PEG-phospholipid derivatives. For example, PEG-phospholipid derivatives have a negative charge on their phosphate group, which leads to multiple disadvantages. First, the negative charge may cause interaction with the cationic lipid in the formulation and, consequently, electrostatic forces that hinder that exchange of the PEG-phospholipid out of the bilayer. Second, the negative charge of the phosphate group neutralizes the cationic charge which is a necessary part of the encapsulation process. To offset the neutralizing effect of the phosphate group, a higher molar percentage of the cationic lipid must be used, thus increasing the toxicity of the formulation. In addition, in contrast to PEG-ceramides, PEG-DAA conjugates are easier to produce and manufacture.

In addition to the foregoing components, the SPLPs of the present invention can further comprise cationic poly(ethylene glycol) (PEG) lipids, or CPLs, that have been designed for insertion into lipid bilayers to impart a positive charge (see, Chen, et al., *Bioconj. Chem.* 11:433-437 (2000)). Suitable SPLPs and SPLP-CPLs for use in the present invention, and methods of making and using SPLPs and SPLP-CPLs, are disclosed, e.g., in U.S. application Ser. No. 09/553,639, which was filed Apr. 20, 2000, and PCT Patent Application No. CA 00/00451, which was filed Apr. 20, 2000 and which published as WO 00/62813 on Oct. 26, 2000, the teachings of each of which is incorporated herein in its entirety by reference.

A. Products of Interest

In addition to the above components, the SPLPs and SNALPs of the present invention comprise a nucleic acid (e.g., single stranded or double stranded DNA, single stranded or double stranded RNA, RNAi, siRNA, and the like). Suitable nucleic acids include, but are not limited to, plasmids, antisense oligonucleotides, ribozymes as well as other poly- and oligonucleotides. In preferred embodiments, the nucleic acid encodes a product, e.g., a therapeutic product, of interest.

The product of interest can be useful for commercial purposes, including for therapeutic purposes as a pharmaceutical or diagnostic. Examples of therapeutic products include a protein, a nucleic acid, an antisense nucleic acid, ribozymes, tRNA, snRNA, siRNA, an antigen, Factor VIII, and Apoptin (Zhuang et al. (1995) *Cancer Res.* 55(3): 486-489). Suitable classes of gene products include, but are not limited to, cytotoxic/suicide genes, immunomodulators, cell receptor ligands, tumor suppressors, and anti-angiogenic genes. The particular gene selected will depend on the intended purpose or treatment. Examples of such genes of interest are described below and throughout the specification.

1. siRNA

The nucleic acid component of the SNALPs and SPLPs typically comprise an interfering RNA (i.e., siRNA), which can be provided in several forms including, e.g. as one or more isolated small-interfering RNA (siRNA) duplexes, longer double-stranded RNA (dsRNA) or as siRNA or dsRNA transcribed from a transcriptional cassette in a DNA plasmid.

An RNA population can be used to provide long precursor RNAs, or long precursor RNAs that have substantial or complete identity to a selected target sequence can be used to make the siRNA. The RNAs can be isolated from cells or tissue, synthesized, and/or cloned according to methods well known to those of skill in the art. The RNA can be a mixed population (obtained from cells or tissue, transcribed from cDNA, subtrated, selected etc.), or can represent a single target sequence. RNA can be naturally occurring, e.g., isolated from tissue or cell samples, synthesized in vitro, e.g., using T7 or SP6 polymerase and PCR products or a cloned cDNA; or chemically synthesized.

To form a long dsRNA, for synthetic RNAs, the complement is also transcribed in vitro and hybridized to form a dsRNA. If a naturally occurring RNA population is used, the RNA complements are also provided (e.g., to form dsRNA for digestion by *E. coli* RNAse III or Dicer), e.g., by transcribing cDNAs corresponding to the RNA population, or by using RNA polymerases. The precursor RNAs are then hybridized to form double stranded RNAs for digestion. The dsRNAs can be directly encapsulated in the SNALPs or can be digested in vitro prior to encapsulation.

Alternatively, one or more DNA plasmids encoding one or more siRNA templates are encapsulated in a nucleic acid-lipid particle. siRNA can be transcribed as sequences that automatically fold into duplexes with hairpin loops from DNA templates in plasmids having RNA polymerase III transcriptional units, for example, based on the naturally occurring transcription units for small nuclear RNA U6 or human RNase P RNA H1 (see, Brummelkamp, et al., *Science* 296: 550 (2002); Donzé, et al., *Nucleic Acids Res.* 30:e46 (2002); Paddison, et al., *Genes Dev.* 16:948 (2002); Yu, et al., *Proc. Natl. Acad. Sci.* 99:6047 (2002); Lee, et al., *Nat. Biotech.* 20:500 (2002); Miyagishi, et al., *Nat. Biotech.* 20:497 (2002); Paul, et al., *Nat. Biotech.* 20:505 (2002); and Sui, et al., *Proc. Natl. Acad. Sci.* 99:5515 (2002)). Typically, a transcriptional unit or cassette will contain an RNA transcript promoter sequence, such as an H1-RNA or a U6 promoter, operably linked to a template for transcription of a desired siRNA sequence and a termination sequence, comprised of 2-3 uridine residues and a polythymidine (T5) sequence (polyadenylation signal) (Brummelkamp, Science, supra). The selected promoter can provide for constitutive or inducible transcription. Compositions and methods for DNA-directed transcription of RNA interference molecules is described in detail in U.S. Pat. No. 6,573,099, incorporated herein by reference. Preferably, the synthesized or transcribed siRNA have 3' overhangs of about 1-4 nucleotides, preferably of about 2-3 nucleotides and 5' phosphate termini (Elbashir, et al., *Genes Dev.* 15:188 (2001); Nykänen, et al., *Cell* 107:309 (2001)). The transcriptional unit is incorporated into a plasmid or DNA vector from which the interfering RNA is transcribed. Plasmids suitable for in vivo delivery of genetic material for therapeutic purposes are described in detail in U.S. Pat. Nos. 5,962,428 and 5,910,488, both of which are incorporated herein by reference. The selected plasmid can provide for transient or stable delivery of a target cell. It will be apparent to those of skill in the art that plasmids originally designed to express desired gene sequences can be modified to contain a transcriptional unit cassette for transcription of siRNA.

Methods for isolating RNA, synthesizing RNA, hybridizing nucleic acids, making and screening cDNA libraries, and performing PCR are well known in the art (see, e.g., Gubler & Hoffman, *Gene* 25:263-269 (1983); Sambrook et al., supra; Ausubel et al., supra), as are PCR methods (see U.S. Pat. Nos. 4,683,195 and 4,683,202; *PCR Protocols: A Guide to Methods and Applications* (Innis et al., eds, 1990)). Expression libraries are also well known to those of skill in the art. Additional basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

A suitable plasmid is engineered to contain, in expressible form, a template sequence that encodes a partial length sequence or an entire length sequence of a gene product of interest. Template sequences can also be used for providing isolated or synthesized siRNA and dsRNA. Generally, it is desired to downregulate or silence the transcription and translation of a gene product of interest. Suitable classes of gene products include, but are not limited to, genes associated with tumorigenesis and cell transformation, angiogenic genes, immunomodulator genes, such as those associated with inflammatory and autoimmune responses, ligand receptor genes, genes associated with neurodegenerative disorders, and genes associated with viral infection and survival.

Examples of gene sequences associated with tumorigenesis and cell transformation include translocation sequences such as MLL fusion genes, BCR-ABL (Wilda, et al., *Oncogene*, 21:5716 (2002); Scherr, et al., *Blood* 101:1566), TEL-AML1, EWS-FLI1, TLS-FUS, PAX3-FKHR, BCL-2, AML1-ETO and AML1-MTG8 (Heidenreich, et al., *Blood* 101:3157 (2003)); overexpressed sequences such as multidrug resistance genes (Nieth, et al., *FEBS Lett.* 545:144 (2003); Wu, et al, *Cancer Res.* 63:1515 (2003)), cyclins (Li, et al., *Cancer Res.* 63:3593 (2003); Zou, et al., *Genes Dev.* 16:2923 (2002)), beta-Catenin (Verma, et al., *Clin Cancer Res.* 9:1291 (2003)), telomerase genes (Kosciolek, et al., *Mol Cancer Ther.* 2:209 (2003)), c-MYC, N-MYC, BCL-2, ERBB1 and ERBB2 (Nagy, et al. *Exp. Cell Res.* 285:39 (2003)); and mutated sequences such as RAS (reviewed in Tuschl and Borkhardt, *Mol. Interventions*, 2:158 (2002)). Silencing of sequences that encode DNA repair enzymes find use in combination with the administration of chemotherapeutic agents (Collis, et al., *Cancer Res.* 63:1550 (2003)). Genes encoding proteins associated with tumor migration are also target sequences of interest, for example, integrins, selectins and metalloproteinases. The foregoing examples are not exclusive. Any whole or partial gene sequence that facilitates or promotes tumorigenesis or cell transformation, tumor growth or tumor migration can be included as a template sequence.

Angiogenic genes are able to promote the formation of new vessels. Of particular interest is Vascular Endothelial Growth Factor (VEGF) (Reich, et al., *Mol. Vis.* 9:210 (2003)).

Immunomodulator genes are genes that modulate one or more immune responses. Examples of immunomodulator genes include cytokines such as growth factors (e.g., TGF-α, TGF-β, EGF, FGF, IGF, NGF, PDGF, CGF, GM-CSF, SCF, etc.), interleukins (e.g., IL-2, IL-4, IL-12 (Hill, et al., *J. Immunol.* 171:691 (2003)), IL-15, IL-18, IL-20, etc.), interferons (e.g., IFN-α, IFN-β, IFN-γ, etc.) and TNF. Fas and Fas Ligand genes are also immunomodulator target sequences of interest (Song, et al., *Nat. Med.* 9:347 (2003)). Genes encoding secondary signaling molecules in hematopoietic and lymphoid cells are also included in the present invention, for example, Tec family kinases, such as Bruton's tyrosine kinase (Btk) (Heinonen, et al., *FEBS Lett.* 527:274 (2002)).

Cell receptor ligands include ligands that are able to bind to cell surface receptors (e.g., insulin receptor, EPO receptor, G-protein coupled receptors, receptors with tyrosine kinase activity, cytokine receptors, growth factor receptors, etc.), to modulate (e.g,. inhibit, activate, etc.) the physiological pathway that the receptor is involved in (e.g., glucose level modulation, blood cell development, mitogenesis, etc.). Examples of cell receptor ligands include cytokines, growth factors, interleukins, interferons, erythropoietin (EPO), insulin, glucagon, G-protein coupled receptor ligands, etc.). Templates coding for an expansion of trinucleotide repeats (e.g., CAG repeats), find use in silencing pathogenic sequences in neurodegenerative disorders caused by the expansion of trinucleotide repeats, such as spinobulbular muscular atrophy and Huntington's Disease (Caplen, et al., *Hum. Mol. Genet.* 11:175 (2002)).

Genes associated with viral infection and survival include those expressed by a virus in order to bind, enter and replicate in a cell. Of particular interest are viral sequences associated with chronic viral diseases. Viral sequences of particular interest include sequences of Human Immunodeficiency Virus (HIV) (Banerjea, et al., *Mol. Ther.* 8:62 (2003); Song, et al., *J. Virol.* 77:7174 (2003); Stephenson *JAMA* 289:1494 (2003); Qin, et al., *Proc. Natl. Acad. Sci.* 100:183 (2003)), Hepatitis viruses (Hamasaki, et al., *FEBS Lett.* 543:51 (2003); Yokota, et al., *EMBO Rep.* 4:602 (2003); Schlomai, et al., *Hepatology* 37:764 (2003); Wilson, et al., *Proc. Natl. Acad. Sci.* 100:2783 (2003); Kapadia, et al., *Proc. Natl. Acad. Sci.* 100:2014 (2003)), Herpes viruses (Jia, et al., *J. Virol.* 77:3301 (2003)), and Human Papilloma Viruses (HPV) (Hall, et al., *J. Virol.* 77:6066 (2003); Jiang, et al., *Oncogene* 21:6041 (2002)).

2. Additional Therapeutic Products

As explained above, in some embodiments of the present invention, the SPLPs and SNALPs encapsulate a nucleic acid encoding a therapeutic product such as, for example, tumor suppressor genes, immunomodulator genes, cell receptor ligand genes, anti-antigogenic genes, and cytotoxic/suicide genes.

a) Tumor Suppressors

Tumor suppressor genes are genes that are able to inhibit the growth of a cell, particularly tumor cells. Thus, delivery of these genes to tumor cells is useful in the treatment of cancers. Tumor suppressor genes include, but are not limited to, p53 (Lamb et al., *Mol. Cell. Biol.* 6:1379-1385 (1986), Ewen et al., *Science* 255:85-87 (1992), Ewen et al. (1991) *Cell* 66:1155-1164, and Hu et al., *EMBO J.* 9:1147-1155 (1990)), RB1 (Toguchida et al. (1993) *Genomics* 17:535-543), WT1 (Hastie, N. D., *Curr. Opin. Genet. Dev.* 3:408-413 (1993)), NF1 (Trofatter et al., *Cell* 72:791-800 (1993), Cawthon et al., *Cell* 62:193-201 (1990)), VHL (Latif et al., *Science* 260:1317-1320 (1993)), APC (Gorden et al., *Cell* 66:589-600 (1991)), DAP kinase (see e.g., Diess et al. (1995) *Genes Dev.* 9:15-30), p16 (see e.g., Marx (1994) *Science* 264(5167): 1846), ARF (see e.g., Quelle et al. (1995) *Cell* 83(6): 993-1000), Neurofibromin (see e.g., Huynh et al. (1992) *Neurosci. Lett.* 143(1-2): 233-236), and PTEN (see e.g., Li et al. (1997) *Science* 275(5308): 1943-1947).

b) Immunomodulator Genes:

Immunomodulator genes are genes that modulate one or more immune responses. Examples of immunomodulator genes include cytokines such as growth factors (e.g., TGF-α, TGF-β, EGF, FGF, IGF, NGF, PDGF, CGF, GM-CSF, G-CSF, SCF, etc.), interleukins (e.g., IL-2, IL-3, IL-4, IL-6, IL-7, IL-10, IL-12, IL-15, IL-20, etc.), interferons (e.g., IFN-α, IFN-β, IFN-γ, etc.), TNF (e.g., TNF-α), and Flt3-Ligand.

c) Cell Receptor Ligands

Cell receptor ligands include ligands that are able to bind to cell surface receptors (e.g., insulin receptor, EPO receptor, G-protein coupled receptors, receptors with tyrosine kinase activity, cytokine receptors, growth factor receptors, etc.), to modulate (e.g,. inhibit, activate, etc.) the physiological pathway that the receptor is involved in (e.g., glucose level modulation, blood cell development, mitogenesis, etc.). Examples of cell receptor ligands include, but are not limited to, cytokines, growth factors, interleukins, interferons, erythropoietin (EPO), insulin, single-chain insulin (Lee et al. (2000) *Nature* 408: 483-488), glucagon, G-protein coupled receptor ligands, etc.). These cell surface ligands can be useful in the treatment of patients suffering from a disease. For example, a single-chain insulin when expressed under the control of the glucose-responsive hepatocyte-specific L-type pyruvate kinase (LPK) promoter was able to cause the remission of diabetes in streptocozin-induced diabetic rats and autoimmune diabetic mice without side effects (Lee et al. (2000) *Nature* 408:483-488). This single-chain insulin was created by replacing the 35 amino acid resides of the C-peptide of insulin with a short turn-forming heptapeptide (Gly-Gly-Gly-Pro-Gly-Lys-Arg).

d) Anti-Angiogenic Genes

Anti-angiogenic genes are able to inhibit neovascularization. These genes are particularly useful for treating those cancers in which angiogenesis plays a role in the pathological development of the disease. Examples of anti-angiogenic genes include, but are not limited to, endostatin (see e.g., U.S. Pat. No. 6,174,861), angiostatin (see, e.g., U.S. Pat. No. 5,639,725), and VEGF-R2 (see e.g., Decaussin et al. (1999) *J. Pathol.* 188(4): 369-737).

e) Cytotoxic/Suicide Genes

Cytotoxic/suicide genes are those genes that are capable of directly or indirectly killing cells, causing apoptosis, or arresting cells in the cell cycle. Such genes include, but are not limited to, genes for immunotoxins, a herpes simplex virus thymidine kinase (HSV-TK), a cytosine deaminase, a xanthine-guaninephosphoribosyl transferase, a p53, a purine nucleoside phosphorylase, a carboxylesterase, a deoxycytidine kinase, a nitroreductase, a thymidine phosphorylase, and a cytochrome P450 2B1.

In a gene therapy technique known as gene-delivered enzyme prodrug therapy ("GDEPT") or, alternatively, the "suicide gene/prodrug" system, agents such as acyclovir and ganciclovir (for thymidine kinase), cyclophosphoamide (for cytochrome P450 2B1), 5-fluorocytosine (for cytosine deaminase), are typically administered systemically in conjunction (e.g., simultaneously or nonsimultaneously, e.g., sequentially) with a expression cassette encoding a suicide gene compositions of the present invention to achieve the desired cytotoxic or cytostatic effect (see, e.g., Moolten, F. L., *Cancer Res.*, 46:5276-5281 (1986)). For a review of the GDEPT system, see, Moolten, F. L., *The Internet Book of Gene Therapy, Cancer Therapeutics*, Chapter 11 (Sobol, R. E., Scanlon, N.J. (Eds) Appelton & Lange (1995)). In this method, a heterologous gene is delivered to a cell in an expression cassette containing a RNAP promoter, the heterologous gene encoding an enzyme that promotes the metabolism of a first compound to which the cell is less sensitive (i.e., the "prodrug") into a second compound to which is cell is more sensitive. The prodrug is delivered to the cell either with the gene or after delivery of the gene. The enzyme will process the prodrug into the second compound and respond accordingly. A suitable system proposed by Moolten is the herpes simplex virus-thymidine kinase (HSV-TK) gene and the prodrug ganciclovir. This method has recently been employed using cationic lipid-nucleic aggregates for local delivery (i.e., direct intra-tumoral injection), or regional delivery (i.e., intra-peritoneal) of the TK gene to mouse tumors by Zerrouqui, et al., *Can. Gen. Therapy*, 3(6):385-392 (1996); Sugaya, et al., *Hum. Gen. Ther.*, 7:223-230 (1996) and Aoki, et al., *Hum. Gen. Ther.*, 8:1105-1113 (1997). Human clinical trials using a GDEPT system employing viral vectors have been proposed (see, *Hum. Gene Ther.*, 8:597-613 (1997), and *Hum. Gene Ther.*, 7:255-267 (1996)) and are underway.

For use with the instant invention, the most preferred therapeutic products are those which are useful in gene-delivered enzyme prodrug therapy ("GDEPT"). Any suicide gene/prodrug combination can be used in accordance with the present invention. Several suicide gene/prodrug combinations suitable for use in the present invention are cited in Sikora, K. in OECD Documents, Gene Delivery Systems at pp. 59-71 (1996), incorporated herein by reference, include, but are not limited to, the following:

| Suicide Gene Product | Less Active ProDrug | Activated Drug |
| --- | --- | --- |
| Herpes simplex virus type 1 thymidine kinase (HSV-TK) | ganciclovir(GCV), acyclovir, bromovinyl-deoxyuridine, or other substrates | phosphorylated dGTP analogs |
| Cytosine Deaminase (CD) | 5-fluorocytosine | 5-fluorouracil |
| Xanthine-guanine-phosphoribosyl transferase (XGPRT) | 6-thioxanthine (6TX) | 6-thioguano-sinemonophosphate |
| Purine nucleoside phosphorylase | MeP-dr | 6-methylpurine |
| Cytochrome P450 2B1 | cyclophosphamide | [cytotoxic metabolites] |
| Linamarase | amygdalin | cyanide |
| Nitroreductase | CB 1954 | nitrobenzamidine |
| Beta-lactamase | PD | PD mustard |
| Beta-glucuronidase | adria-glu | adriamycin |
| Carboxypeptidase | MTX-alanine | MTX |
| Glucose oxidase | glucose | peroxide |
| Penicillin amidase | adria-PA | adriamycin |
| Superoxide dismutase | XRT | DNA damaging agent |
| Ribonuclease | RNA | cleavage products |

Any prodrug can be used if it is metabolized by the heterologous gene product into a compound to which the cell is more sensitive. Preferably, cells are at least 10-fold more sensitive to the metabolite than the prodrug.

Modifications of the GDEPT system that may be useful with the invention include, for example, the use of a modified TK enzyme construct, wherein the TK gene has been mutated to cause more rapid conversion of prodrug to drug (see, for example, Black, et al., *Proc. Natl. Acad. Sci, U.S.A.*, 93: 3525-3529 (1996)). Alternatively, the TK gene can be delivered in a bicistronic construct with another gene that enhances its effect. For example, to enhance the "bystander effect" also known as the "neighbor effect" (wherein cells in the vicinity of the transfected cell are also killed), the TK gene can be delivered with a gene for a gap junction protein, such as connexin 43. The connexin protein allows diffusion of toxic products of the TK enzyme from one cell into another. The TK/Connexin 43 construct has a CMV promoter operably linked to a TK gene by an internal ribosome entry sequence and a Connexin 43-encoding nucleic acid.

B. SPLP and SNALP Preparation and Uses Thereof

The SPLPs and SNALPs of the present invention, i.e., those SPLPs and SNALPs containing PEG-DAA conjugates, can be made using any of a number of different methods. In one embodiment, the present invention provides lipid-nucleic acid particles produced via hydrophobic nucleic acid-lipid intermediate complexes. The complexes are preferably charge-neutralized. Manipulation of these complexes in either detergent-based or organic solvent-based systems can lead to particle formation in which the nucleic acid is protected.

The present invention provides a method of preparing serum-stable nucleic acid-lipid particles in which a nucleic acid is encapsulated in a lipid bilayer and is protected from degradation. Additionally, the particles formed in the present invention are preferably neutral or negatively-charged at physiological pH. For in vivo applications, neutral particles are advantageous, while for in vitro applications the particles are more preferably negatively charged. This provides the further advantage of reduced aggregation over the positively-charged liposome formulations in which a nucleic acid can be encapsulated in cationic lipids.

The particles made by the methods of this invention have a size of about 50 to about 150 nm, with a majority of the particles being about 65 to 85 nm. The particles can be formed by either a detergent dialysis method or by a modification of a reverse-phase method which utilizes organic solvents to provide a single phase during mixing of the components. Without intending to be bound by any particular mechanism of formation, a plasmid or other nucleic acid is contacted with a detergent solution of cationic lipids to form a coated plasmid complex. These coated plasmids can aggregate and precipitate. However, the presence of a detergent reduces this aggregation and allows the coated plasmids to react with excess lipids (typically, noncationic lipids) to form particles in which the plasmid or other nucleic acid is encapsulated in a lipid bilayer. The methods described below for the formation of plasmid-lipid particles using organic solvents follow a similar scheme.

In some embodiments, the particles are formed using detergent dialysis. Thus, the present invention provides a method for the preparation of serum-stable nucleic acid-lipid particles, comprising:

(a) combining a nucleic acid with cationic lipids in a detergent solution to form a coated plasmid-lipid complex;
(b) contacting noncationic lipids with the coated nucleic acid-lipid complex to form a detergent solution comprising a plasmid-lipid complex and noncationic lipids; and
(c) dialyzing the detergent solution of step (b) to provide a solution of serum-stable nucleic acid-lipid particles, wherein the nucleic acid is encapsulated in a lipid bilayer and the particles are serum-stable and have a size of from about 50 to about 150 nm.

An initial solution of coated nucleic acid-lipid complexes is formed by combining the plasmid with the cationic lipids in a detergent solution.

In these embodiments, the detergent solution is preferably an aqueous solution of a neutral detergent having a critical micelle concentration of 15-300 mM, more preferably 20-50 mM. Examples of suitable detergents include, for example, N,N'-((octanoylimino)-bis-(trimethylene))-bis-(D-gluconamide) (BIGCHAP); BRIJ 35; Deoxy-BIGCHAP; dodecylpoly(ethylene glycol)ether; Tween 20; Tween 40; Tween 60; Tween 80; Tween 85; Mega 8; Mega 9; Zwittergent® 3-08; Zwittergent® 3-10; Triton X-405; hexyl-, heptyl-, octyl- and nonyl-β-D-glucopyranoside; and heptylthioglucopyranoside; with octyl β-D-glucopyranoside and Tween-20 being the most preferred. The concentration of detergent in the detergent solution is typically about 100 mM to about 2 M, preferably from about 200 mM to about 1.5 M.

The cationic lipids and nucleic acids will typically be combined to produce a charge ratio (+/−) of about 1:1 to about 20:1, preferably in a ratio of about 1:1 to about 12:1, and more preferably in a ratio of about 2:1 to about 6:1. Additionally, the overall concentration of plasmid in solution will typically be from about 25 µg/mL to about 1 mg/mL, preferably from about 25 µg/mL to about 500 µg/mL, and more preferably from about 100 µg/mL to about 250 µg/mL. The combination of nucleic acids and cationic lipids in detergent solution is kept, typically at room temperature, for a period of time which is sufficient for the coated complexes to form. Alternatively, the nucleic acids and cationic lipids can be combined in the detergent solution and warmed to temperatures of up to about 37° C. For nucleic acids which are particularly sensitive to temperature, the coated complexes can be formed at lower temperatures, typically down to about 4° C.

In a preferred embodiment, the nucleic acid to lipid ratios (mass/mass ratios) in a formed SPLP or SNALP will range from about 0.01 to about 0.08. The ratio of the starting materials also falls within this range because the purification step typically removes the unencapsulated nucleic acid as well as the empty liposomes. In another preferred embodiment, the SPLP or SNALP preparation uses about 400 µg nucleic acid per 10 mg total lipid or a nucleic acid to lipid ratio of about 0.01 to about 0.08 and, more preferably, about 0.04, which corresponds to 1.25 mg of total lipid per 50 µg of nucleic acid.

The detergent solution of the coated nucleic acid-lipid complexes is then contacted with non-cationic lipids to provide a detergent solution of nucleic acid-lipid complexes and non-cationic lipids. The non-cationic lipids which are useful in this step include, diacylphosphatidylcholine, diacylphosphatidylethanolamine, ceramide, sphingomyelin, cephalin, cardiolipin, and cerebrosides. In preferred embodiments, the non-cationic lipids are diacylphosphatidylcholine, diacylphosphatidylethanolamine, ceramide or sphingomyelin. The acyl groups in these lipids are preferably acyl groups derived from fatty acids having $C_{10}$-$C_{24}$ carbon chains. More preferably the acyl groups are lauroyl, myristoyl, palmitoyl, stearoyl or oleoyl. In particularly preferred embodiments, the non-cationic lipid will be 1,2-sn-dioleoylphosphatidylethanolamine (DOPE), palmitoyl oleoyl phosphatidylcholine (POPC), egg phosphatidylcholine (EPC), distearoylphosphatidylcholine (DSPC), cholesterol, or a mixture thereof. In the most preferred embodiments, the nucleic acid-lipid particles will be fusogenic particles with enhanced properties in vivo and the non-cationic lipid will be DSPC or DOPE. As explained above, the nucleic acid-lipid particles of the present invention will further comprise PEG-DAA conjugates. In addition, the nucleic acid-lipid particles of the present invention will further comprise cholesterol.

The amount of non-cationic lipid which is used in the present methods is typically about 0.5 to about 10 mg of total lipids to 50 µg of nucleic acid. Preferably the amount of total lipid is from about 1 to about 5 mg per 50 µg of nucleic acid.

Following formation of the detergent solution of nucleic acid-lipid complexes and non-cationic lipids, the detergent is removed, preferably by dialysis. The removal of the detergent results in the formation of a lipid-bilayer which surrounds the nucleic acid providing serum-stable nucleic acid-lipid particles which have a size of from about 50 nm to about 150 nm.

The particles thus formed do not aggregate and are optionally sized to achieve a uniform particle size.

The serum-stable nucleic acid-lipid particles can be sized by any of the methods available for sizing liposomes. The sizing may be conducted in order to achieve a desired size range and relatively narrow distribution of particle sizes.

Several techniques are available for sizing the particles to a desired size. One sizing method, used for liposomes and equally applicable to the present particles is described in U.S. Pat. No. 4,737,323, incorporated herein by reference. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles may be extruded through successively smaller-pore membranes, to achieve a gradual reduction in size.

In another group of embodiments, the present invention provides a method for the preparation of serum-stable nucleic acid-lipid particles, comprising:
(a) preparing a mixture comprising cationic lipids and non-cationic lipids in an organic solvent;
(b) contacting an aqueous solution of nucleic acid with said mixture in step (a) to provide a clear single phase; and
(c) removing said organic solvent to provide a suspension of nucleic acid-lipid particles, wherein said nucleic acid is encapsulated in a lipid bilayer, and said particles are stable in serum and have a size of from about 50 to about 150 nm.

The nucleic acids (e.g., plasmids), cationic lipids and non-cationic lipids which are useful in this group of embodiments are as described for the detergent dialysis methods above.

The selection of an organic solvent will typically involve consideration of solvent polarity and the ease with which the solvent can be removed at the later stages of particle formation. The organic solvent, which is also used as a solubilizing agent, is in an amount sufficient to provide a clear single phase mixture of plasmid and lipids. Suitable solvents include, but are not limited to, chloroform, dichloromethane, diethylether, cyclohexane, cyclopentane, benzene, toluene, methanol, or other aliphatic alcohols such as propanol, isopropanol, butanol, tert-butanol, iso-butanol, pentanol and hexanol. Combinations of two or more solvents may also be used in the present invention.

Contacting the nucleic acid with the organic solution of cationic and non-cationic lipids is accomplished by mixing together a first solution of nucleic acids, which is typically an aqueous solution, and a second organic solution of the lipids. One of skill in the art will understand that this mixing can take place by any number of methods, for example by mechanical means such as by using vortex mixers.

After the nucleic acid has been contacted with the organic solution of lipids, the organic solvent is removed, thus forming an aqueous suspension of serum-stable nucleic acid-lipid particles. The methods used to remove the organic solvent will typically involve evaporation at reduced pressures or blowing a stream of inert gas (e.g., nitrogen or argon) across the mixture.

The serum-stable nucleic acid-lipid particles thus formed will typically be sized from about 50 nm to 150 nm. To achieve further size reduction or homogeneity of size in the particles, sizing can be conducted as described above.

In other embodiments, the methods will further comprise adding nonlipid polycations which are useful to effect the transformation of cells using the present compositions. Examples of suitable nonlipid polycations include, but are limited to, hexadimethrine bromide (sold under the brandname POLYBRENE®, from Aldrich Chemical Co., Milwaukee, Wis., USA) or other salts of heaxadimethrine. Other suitable polycations include, for example, salts of poly-L-ornithine, poly-L-arginine, poly-L-lysine, poly-D-lysine, polyallylamine and polyethyleneimine.

In some embodiments, the polycations can be used to condense nucleic acids prior to encapsulation of the nucleic acids in the SPLP or SNALP. For example, the polycation (e.g., polyethyleneimine) can be used as a condensing agent to form a PEI-condensed DNA complex as described in WO 00/03683.

In certain embodiments, the formation of the nucleic acid-lipid particles can be carried out either in a mono-phase system (e.g., a Bligh and Dyer monophase or similar mixture of aqueous and organic solvents) or in a two-phase system with suitable mixing.

When formation of the complexes is carried out in a mono-phase system, the cationic lipids and nucleic acids are each dissolved in a volume of the mono-phase mixture. Combination of the two solutions provides a single mixture in which the complexes form. Alternatively, the complexes can form in two-phase mixtures in which the cationic lipids bind to the nucleic acid (which is present in the aqueous phase), and "pull" it into the organic phase.

In another embodiment, the present invention provides a method for the preparation of nucleic acid-lipid particles, comprising:
(a) contacting nucleic acids with a solution comprising noncationic lipids and a detergent to form a nucleic acid-lipid mixture;
(b) contacting cationic lipids with the nucleic acid-lipid mixture to neutralize a portion of the negative charge of the nucleic acids and form a charge-neutralized mixture of nucleic acids and lipids; and
(c) removing the detergent from the charge-neutralized mixture to provide the lipid-nucleic acid particles in which the nucleic acids are protected from degradation.

In one group of embodiments, the solution of non-cationic lipids and detergent is an aqueous solution. Contacting the nucleic acids with the solution of non-cationic lipids and detergent is typically accomplished by mixing together a first solution of nucleic acids and a second solution of the lipids and detergent. One of skill in the art will understand that this mixing can take place by any number of methods, for example, by mechanical means such as by using vortex mixers. Preferably, the nucleic acid solution is also a detergent solution. The amount of non-cationic lipid which is used in the present method is typically determined based on the amount of cationic lipid used, and is typically of from about 0.2 to 5 times the amount of cationic lipid, preferably from about 0.5 to about 2 times the amount of cationic lipid used.

The nucleic acid-lipid mixture thus formed is contacted with cationic lipids to neutralize a portion of the negative charge which is associated with the nucleic acids (or other polyanionic materials) present. The amount of cationic lipids used will typically be sufficient to neutralize at least 50% of the negative charge of the nucleic acid. Preferably, the negative charge will be at least 70% neutralized, more preferably at least 90% neutralized. Cationic lipids which are useful in the present invention, include, for example, DODAC, DOTMA, DDAB, DOTAP, DC-Chol and DMRIE. These lipids and related analogs have been described in co-pending U.S. Ser. No. 08/316,399; U.S. Pat. Nos. 5,208,036, 5,264, 618, 5,279,833 and 5,283,185, the disclosures of which are incorporated herein by reference. Additionally, a number of commercial preparations of cationic lipids are available and can be used in the present invention. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic lipids comprising DOGS in ethanol from Promega Corp., Madison, Wis., USA).

Contacting the cationic lipids with the nucleic acid-lipid mixture can be accomplished by any of a number of techniques, preferably by mixing together a solution of the cationic lipid and a solution containing the nucleic acid-lipid mixture. Upon mixing the two solutions (or contacting in any other manner), a portion of the negative charge associated with the nucleic acid is neutralized. Nevertheless, the nucleic acid remains in an uncondensed state and acquires hydrophilic characteristics.

After the cationic lipids have been contacted with the nucleic acid-lipid mixture, the detergent (or combination of detergent and organic solvent) is removed, thus forming the lipid-nucleic acid particles. The methods used to remove the detergent will typically involve dialysis. When organic solvents are present, removal is typically accomplished by evaporation at reduced pressures or by blowing a stream of inert gas (e.g., nitrogen or argon) across the mixture.

The particles thus formed will typically be sized from about 100 nm to several microns. To achieve further size reduction or homogeneity of size in the particles, the lipid-nucleic acid particles can be sonicated, filtered or subjected to other sizing techniques which are used in liposomal formulations and are known to those of skill in the art.

In other embodiments, the methods will further comprise adding nonlipid polycations which are useful to effect the lipofection of cells using the present compositions. Examples of suitable nonlipid polycations include, hexadimethrine bromide (sold under the brandname POLYBRENE®, from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine and polyethylene-imine. Addition of these salts is preferably after the particles have been formed.

In another aspect, the present invention provides methods for the preparation of nucleic acid-lipid particles, comprising:
  (a) contacting an amount of cationic lipids with nucleic acids in a solution; the solution comprising from about 15-35% water and about 65-85% organic solvent and the amount of cationic lipids being sufficient to produce a +/−charge ratio of from about 0.85 to about 2.0, to provide a hydrophobic lipid-nucleic acid complex;
  (b) contacting the hydrophobic, lipid-nucleic acid complex in solution with non-cationic lipids, to provide a nucleic acid-lipid mixture; and
  (c) removing the organic solvents from the lipid-nucleic acid mixture to provide lipid-nucleic acid particles in which the nucleic acids are protected from degradation.

The nucleic acids, non-cationic lipids, cationic lipids and organic solvents which are useful in this aspect of the invention are the same as those described for the methods above which used detergents. In one group of embodiments, the solution of step (a) is a mono-phase. In another group of embodiments, the solution of step (a) is two-phase.

In preferred embodiments, the cationic lipids are DODAC, DDAB, DOTMA, DOSPA, DMRIE, DOGS or combinations thereof. In other preferred embodiments, the noncationic lipids are ESM, DOPE, DOPC, DSPC, polyethylene glycol-based polymers (e.g., PEG 2000, PEG 5000, PEG-modified diacylglycerols, or PEG-modified dialkyloxypropyls), distearoylphosphatidylcholine (DSPC), cholesterol, or combinations thereof. In still other preferred embodiments, the organic solvents are methanol, chloroform, methylene chloride, ethanol, diethyl ether or combinations thereof.

In a particularly preferred embodiment, the nucleic acid is a plasmid; the cationic lipid is DODAC, DDAB, DOTMA, DOSPA, DMRIE, DOGS or combinations thereof; the non-cationic lipid is ESM, DOPE, PEG-DAAs, distearoylphosphatidylcholine (DSPC), cholesterol, or combinations thereof (e.g. DSPC and PEG-DAAs); and the organic solvent is methanol, chloroform, methylene chloride, ethanol, diethyl ether or combinations thereof.

As above, contacting the nucleic acids with the cationic lipids is typically accomplished by mixing together a first solution of nucleic acids and a second solution of the lipids, preferably by mechanical means such as by using vortex mixers. The resulting mixture contains complexes as described above. These complexes are then converted to particles by the addition of non-cationic lipids and the removal of the organic solvent. The addition of the non-cationic lipids is typically accomplished by simply adding a solution of the non-cationic lipids to the mixture containing the complexes. A reverse addition can also be used. Subsequent removal of organic solvents can be accomplished by methods known to those of skill in the art and also described above.

The amount of non-cationic lipids which is used in this aspect of the invention is typically an amount of from about 0.2 to about 15 times the amount (on a mole basis) of cationic lipids which was used to provide the charge-neutralized lipid-nucleic acid complex. Preferably, the amount is from about 0.5 to about 9 times the amount of cationic lipids used.

In yet another aspect, the present invention provides lipid-nucleic acid particles which are prepared by the methods described above. In these embodiments, the lipid-nucleic acid particles are either net charge neutral or carry an overall charge which provides the particles with greater gene lipofection activity. Preferably, the nucleic acid component of the particles is a nucleic acid which encodes a desired protein or blocks the production of an undesired protein. In preferred embodiments, the nucleic acid is a plasmid, the noncationic lipid is egg sphingomyelin and the cationic lipid is DODAC. In particularly preferred embodiments, the nucleic acid is a plasmid, the noncationic lipid is a mixture of DSPC and cholesterol, and the cationic lipid is DOTMA. In other particularly preferred embodiments, the noncationic lipid may further comprise cholesterol.

A variety of general methods for making SPLP-CPLs (CPL-containing SPLPs) or SNALP-CPL's (CPL-containing SNALPs) are discussed herein. Two general techniques include "post-insertion" technique, that is, insertion of a CPL into for example, a pre-formed SPLP or SNALP, and the "standard" technique, wherein the CPL is included in the lipid mixture during for example, the SPLP or SNALP formation steps. The post-insertion technique results in SPLPs having CPLs mainly in the external face of the SPLP or SNALP bilayer membrane, whereas standard techniques provide SPLPs or SNALPs having CPLs on both internal and external faces.

In particular, "post-insertion" involves forming SPLPs or SNALPs (by any method), and incubating the pre-formed SPLPs or SNALPs in the presence of CPL under appropriate conditions (preferably 2-3 hours at 60° C.). Between 60-80% of the CPL can be inserted into the external leaflet of the recipient vesicle, giving final concentrations up to about 5 to 10 mol % (relative to total lipid). The method is especially useful for vesicles made from phospholipids (which can contain cholesterol) and also for vesicles containing PEG-lipids (such as PEG-DAAs).

In an example of a "standard" technique, the CPL-SPLPs and CPL-SNALPs of the present invention can be formed by extrusion. In this embodiment, all of the lipids including the CPL, are co-dissolved in chloroform, which is then removed under nitrogen followed by high vacuum. The lipid mixture is hydrated in an appropriate buffer, and extruded through two polycarbonate filters with a pore size of 100 nm. The resulting SPLPs or SNALPs contain CPL on both of the internal and external faces. In yet another standard technique, the formation of CPL-SPLPs or CPL-SNALPs can be accomplished using a detergent dialysis or ethanol dialysis method, for example, as discussed in U.S. Pat. Nos. 5,976,567 and 5,981,501, both of which are incorporated herein by reference.

The nucleic acid-lipid particles of the present invention can be administered either alone or in mixture with a physiologically-acceptable carrier (such as physiological saline or phosphate buffer) selected in accordance with the route of administration and standard pharmaceutical practice. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc.

The pharmaceutical carrier is generally added following particle formation. Thus, after the particle is formed, the particle can be diluted into pharmaceutically acceptable carriers such as normal saline.

The concentration of particles in the pharmaceutical formulations can vary widely, i.e., from less than about 0.05%, usually at or at least about 2-5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration.

As described above, the nucleic acid-lipid particles of the present invention comprise PEG-DAA conjugates. It is often desirable to include other components that act in a manner similar to the PEG-DAA conjugates and that serve to prevent particle aggregation and to provide a means for increasing circulation lifetime and increasing the delivery of the nucleic acid-lipid particles to the target tissues. Such components include, but are not limited to, PEG-lipid conjugates, such as PEG-ceramides or PEG-phospholipids (such as PEG-PE), ganglioside $G_{M1}$-modified lipids or ATTA-lipids to the particles. Typically, the concentration of the component in the particle will be about 1-20% and, more preferably from about 3-10%.

The pharmaceutical compositions of the present invention may be sterilized by conventional, well known sterilization techniques. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

In another example of their use, lipid-nucleic acid particles can be incorporated into a broad range of topical dosage forms including, but not limited to, gels, oils, emulsions and the like. For instance, the suspension containing the nucleic acid-lipid particles can be formulated and administered as topical creams, pastes, ointments, gels, lotions and the like.

Once formed, the serum-stable nucleic acid-lipid particles of the present invention are useful for the introduction of nucleic acids into cells. Accordingly, the present invention also provides methods for introducing a nucleic acids (e.g., a plasmid) into a cell. The methods are carried out in vitro or in vivo by first forming the particles as described above and then contacting the particles with the cells for a period of time sufficient for transfection to occur.

The nucleic acid-lipid particles of the present invention can be adsorbed to almost any cell type with which they are mixed or contacted. Once adsorbed, the particles can either be endocytosed by a portion of the cells, exchange lipids with cell membranes, or fuse with the cells. Transfer or incorporation of the nucleic acid portion of the particle can take place via any one of these pathways. In particular, when fusion takes place, the particle membrane is integrated into the cell membrane and the contents of the particle combine with the intracellular fluid.

Using the ERP assay of the present invention, the transfection efficiency of the SPLP or other lipid-based carrier system can be optimized. More particularly, the purpose of the ERP assay is to distinguish the effect of various cationic lipids and helper lipid components of SPLPs based on their relative effect on binding/uptake or fusion with/destabilization of the endosomal membrane. This assay allows one to determine quantitatively how each component of the SPLP or other lipid-based carrier system effects transfection efficacy, thereby optimizing the SPLPs or other lipid-based carrier systems. As explained herein, the Endosomal Release Parameter or, alternatively, ERP is defined as:

REPORTER GENE EXPRESSION/CELL

SPLP UPTAKE/CELL

It will be readily apparent to those of skill in the art that any reporter gene (e.g., luciferase, β-galactosidase, green fluorescent protein, etc.) can be used. In addition, the lipid component (or, alternatively, any component of the SPLP or lipid-based formulation) can be labeled with any detectable label provided the does inhibit or interfere with uptake into the cell. Using the ERP assay of the present invention, one of skill in the art can assess the impact of the various lipid components (e.g., cationic lipid, non-cationic lipid, PEG-lipid derivative, PEG-DAA conjugate, ATTA-lipid derivative, calcium, CPLs, cholesterol, etc.) on cell uptake and transfection efficiencies, thereby optimizing the SPLP or other lipid-based carrier system. By comparing the ERPs for each of the various SPLPs or other lipid-based formulations, one can readily determine the optimized system, e.g., the SPLP or other lipid-based formulation that has the greatest uptake in the cell coupled with the greatest transfection efficiency.

Suitable labels for carrying out the ERP assay of the present invention include, but are not limited to, spectral labels, such as fluorescent dyes (e.g., fluorescein and derivatives, such as fluorescein isothiocyanate (FITC) and Oregon Green®; rhodamine and derivatives, such Texas red, tetrarhodimine isothiocynate (TRITC), etc., digoxigenin, biotin, phycoerythrin, AMCA, CyDyes®, and the like; radiolabels, such as $^3H$, $^{125}I$, $^{35}S$, $^{14}C$, $^{32}P$, $^{33}P$, etc.; enzymes, such as horse radish peroxidase, alkaline phosphatase, etc.; spectral colorimetric labels, such as colloidal gold or colored glass or plastic beads, such as polystyrene, polypropylene, latex, etc. The label can be coupled directly or indirectly to a component of the SPLP or other lipid-based carrier system using methods well known in the art. As indicated above, a wide variety of labels can be used, with the choice of label depending on sensitivity required, ease of conjugation with the SPLP component, stability requirements, and available instrumentation and disposal provisions.

V. Liposomes Containing PEG-DAA Conjugates

In addition to the SPLP formulations described above, the PEG-DAA conjugates of the present invention can be used in the preparation of either empty liposomes or liposomes containing one or more bioactive agents as described herein including, e.g., the therapeutic products described herein. Liposomes also typically comprise a cationic lipid and a non-cationic lipid. In some embodiments, the liposomes further comprise a sterol (e.g., cholesterol).

A. Liposome Preparation

A variety of methods are available for preparing liposomes as described in, e.g., Szoka, et al., *Ann. Rev. Biophys. Bioeng.*, 9:467 (1980), U.S. Pat. Nos. 4,186,183, 4,217,344, 4,235,871, 4,261,975, 4,485,054, 4,501,728, 4,774,085, 4,837,028, 4,946,787, PCT Publication No. WO 91/17424, Deamer and Bangham, *Biochim. Biophys. Acta*, 443:629-634 (1976); Fraley, et al., *Proc. Natl. Acad. Sci. USA*, 76:3348-3352 (1979); Hope, et al., *Biochim. Biophys. Acta*, 812:55-65 (1985); Mayer, et al., *Biochim. Biophys. Acta*, 858:161-168 (1986); Williams, et al., *Proc. Natl. Acad. Sci.*, 85:242-246 (1988), the text Liposomes, Marc J. Ostro, ed., Marcel Dekker, Inc., New York, 1983, Chapter 1, and Hope, et al., *Chem. Phys. Lip.*, 40:89 (1986), all of which are incorporated herein by reference. Suitable methods include, but are not limited to, sonication, extrusion, high pressure/homogenization, microfluidization, detergent dialysis, calcium-induced fusion of small liposome vesicles, and ether-infusion methods, all of which are well known in the art.

One method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous buffered solution and allowed to hydrate, typically over a 15-60 minute period with agitation. The size distribution of the resulting multilamellar vesicles can be shifted toward smaller sizes by hydrating the lipids under more vigorous agitation conditions or by adding solubilizing detergents, such as deoxycholate.

Unilamellar vesicles can be prepared by sonication or extrusion. Sonication is generally performed with a tip sonifier, such as a Branson tip sonifier, in an ice bath. Typically, the suspension is subjected to severed sonication cycles. Extrusion may be carried out by biomembrane extruders, such as the Lipex Biomembrane Extruder. Defined pore size in the extrusion filters may generate unilamellar liposomal vesicles of specific sizes. The liposomes may also be formed by extrusion through an asymmetric ceramic filter, such as a Ceraflow Microfilter, commercially available from the Norton Company, Worcester Mass. Unilamellar vesicles can also be made by dissolving phospholipids in ethanol and then injecting the lipids into a buffer, causing the lipids to spontaneously form unilamellar vesicles. Also, phospholipids can be solubilized into a detergent, e.g., cholates, Triton X, or n-alkylglucosides. Following the addition of the drug to the solubilized lipid-detergent micelles, the detergent is removed by any of a number of possible methods including dialysis, gel filtration, affinity chromatography, centrifugation, and ultrafiltration.

Following liposome preparation, the liposomes which have not been sized during formation may be sized to achieve a desired size range and relatively narrow distribution of liposome sizes. A size range of about 0.2-0.4 microns allows the liposome suspension to be sterilized by filtration through a conventional filter. The filter sterilization method can be carried out on a high through-put basis if the liposomes have been sized down to about 0.2-0.4 microns.

Several techniques are available for sizing liposomes to a desired size. One sizing method is described in U.S. Pat. No. 4,737,323, incorporated herein by reference. Sonicating a liposome suspension either by bath or probe sonication produces a progressive size reduction down to small unilamellar vesicles less than about 0.05 microns in size. Homogenization is another method that relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. The size of the liposomal vesicles may be determined by quasi-electric light scattering (QELS) as described in Bloomfield, *Ann. Rev. Biophys. Bioeng.*, 10:421-450 (1981), incorporated herein by reference. Average liposome diameter may be reduced by sonication of formed liposomes. Intermittent sonication cycles may be alternated with QELS assessment to guide efficient liposome synthesis.

Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve gradual reduction in liposome size. For use in the present invention, liposomes having a size ranging from about 0.05 microns to about 0.40 microns are preferred. In particularly preferred embodiments, liposomes are between about 0.05 and about 0.2 microns.

In preferred embodiments, empty liposomes are prepared using conventional methods known to those of skill in the art.

B. Use of Liposomes as Delivery Vechicles

The drug delivery compositions of the present invention (e.g., liposomes, micelles, lipid-nucleic acid particles, virosomes, etc.) are useful for the systemic or local delivery of therapeutic agents or bioactive agents and are also useful in diagnostic assays.

The following discussion refers generally to liposomes; however, it will be readily apparent to those of skill in the art that this same discussion is fully applicable to the other drug delivery systems of the present invention (e.g., micelles, virosomes, nucleic acid-lipid particles (e.g., SNALP and SPLP), etc., all of which can be advantageous formed using the PEG-DAA conjugates of the present invention).

For the delivery of therapeutic or bioactive agents, the PEG-DAA-containing liposome compositions can be loaded with a therapeutic agent and administered to the subject requiring treatment. The therapeutic agents which are administered using the compositions and methods of the present invention can be any of a variety of drugs that are selected to be an appropriate treatment for the disease to be treated. Often the drug will be an antineoplastic agent, such as vincristine (as well as the other vinca alkaloids), doxorubicin, mitoxantrone, camptothecin, cisplatin, bleomycin, cyclophosphamide, methotrexate, streptozotocin, and the like. Especially preferred antitumor agents include, for example, actinomycin D, vincristine, vinblastine, cystine arabinoside, anthracyclines, alkylative agents, platinum compounds, antimetabolites, and nucleoside analogs, such as methotrexate and purine and pyrimidine analogs. It may also be desirable to deliver anti-infective agents to specific tissues using the compounds and methods of the present invention. The compositions of the present invention can also be used for the selective delivery of other drugs including, but not limited to, local anesthetics, e.g., dibucaine and chlorpromazine; beta-adrenergic blockers, e.g., propranolol, timolol and labetolol; antihypertensive agents, e.g., clonidine and hydralazine; antidepressants, e.g., imipramine, amitriptyline and doxepim; anti-conversants, e.g., phenytoin; antihistamines, e.g., diphenhydramine, chlorphenirimine and promethazine; antibiotic/antibacterial agents, e.g., gentamycin, ciprofloxacin, and cefoxitin; antifungal agents, e.g., miconazole, terconazole, econazole, isoconazole, butaconazole, clotrimazole, itraconazole, nystatin, naftifine and amphotericin B; antiparasitic agents, hormones, hormone antagonists, immunomodulators, neurotransmitter antagonists, antiglaucoma agents, vitamins, narcotics, and imaging agents.

As mentioned above, cationic lipids can be used in the delivery of therapeutic genes or oligonucleotides intended to induce or to block production of some protein within the cell. Nucleic acid is negatively charged and may be combined with a positively charged entity to form an SPLP suitable for formulation and cellular delivery of nucleic acid as described above.

Another clinical application of the PEG-DAA conjugates of this invention is as an adjuvant for immunization of both animals and humans. Protein antigens, such as diphtheria toxoid, cholera toxin, parasitic antigens, viral antigens, immunoglobulins, enzymes and histocompatibility antigens, can be incorporated into or attached onto the liposomes containing the PEG-DAA conjugates of the present invention for immunization purposes.

Liposomes containing the PEG-DAA conjugates of the present invention are also particularly useful as carriers for vaccines that will be targeted to the appropriate lymphoid organs to stimulate an immune response.

Liposomes containing the PEG-DAA conjugates of the present invention can also be used as a vector to deliver immunosuppressive or immunostimulatory agents selectively to macrophages. In particular, glucocorticoids useful to suppress macrophage activity and lymphokines that activate macrophages can be delivered using the liposomes of the present invention.

Liposomes containing the PEG-DAA conjugates of the present invention and containing targeting molecules can be used to stimulate or suppress a cell. For example, liposomes incorporating a particular antigen can be employed to stimulate the B cell population displaying surface antibody that specifically binds that antigen. Liposomes incorporating growth factors or lymphokines on the liposome surface can be directed to stimulate cells expressing the appropriate receptors for these factors. Using this approach, bone marrow cells can be stimulated to proliferate as part of the treatment of cancer patients.

Liposomes containing the PEG-DAA conjugates of the present invention can be used to deliver any product (e.g., therapeutic agents, diagnostic agents, labels or other compounds) including those currently formulated in PEG-derivatized liposomes.

In certain embodiments, it is desirable to target the liposomes of this invention using targeting moieties that are specific to a cell type or tissue. Targeting of liposomes using a variety of targeting moieties, such as ligands, cell surface receptors, glycoproteins, vitamins (e.g., riboflavin) and monoclonal antibodies, has been previously described (see, e.g., U.S. Pat. Nos. 4,957,773 and 4,603,044, the teachings of which are incorporated herein by reference). The targeting moieties can comprise the entire protein or fragments thereof.

Targeting mechanisms generally require that the targeting agents be positioned on the surface of the liposome in such a manner that the target moiety is available for interaction with the target, for example, a cell surface receptor. In one embodiment, the liposome is designed to incorporate a connector portion into the membrane at the time of liposome formation. The connector portion must have a lipophilic portion that is firmly embedded and anchored into the membrane. It must also have a hydrophilic portion that is chemically available on the aqueous surface of the liposome. The hydrophilic portion is selected so as to be chemically suitable with the targeting agent, such that the portion and agent form a stable chemical bond. Therefore, the connector portion usually extends out from the liposome's surface and is configured to correctly position the targeting agent. In some cases, it is possible to attach the target agent directly to the connector portion, but in many instances, it is more suitable to use a third molecule to act as a "molecular bridge." The bridge links the connector portion and the target agent off of the surface of the liposome, thereby making the target agent freely available for interaction with the cellular target.

Standard methods for coupling the target agents can be used. For example, phosphatidylethanolamine, which can be activated for attachment of target agents, or derivatized lipophilic compounds, such as lipid-derivatized bleomycin, can be used. Antibody-targeted liposomes can be constructed using, for instance, liposomes that incorporate protein A (see, Renneisen, et al., *J. Bio. Chem.*, 265:16337-16342 (1990) I:and Leonetti, et al., *Proc. Natl. Acad. Sci.* (USA), 87:2448-2451 (1990)). Examples of targeting moieties can also include other proteins, specific to cellular components, including antigens associated with neoplasms or tumors. Proteins used as targeting moieties can be attached to the liposomes via covalent bonds. See, Heath, Covalent Attachment of Proteins to Liposomes, 149 Methods in Enzymology 111-119 (Academic Press, Inc. 1987). Other targeting methods include the biotin-avidin system.

In some cases, the diagnostic targeting of the liposome can subsequently be used to treat the targeted cell or tissue. For example, when a toxin is coupled to a targeted liposome, the toxin can then be effective in destroying the targeted cell, such as a neoplasmic cell.

C. Use of the Liposomes as Diagnostic Agents

The drug delivery compositions, e.g., liposomes, prepared using the PEG-DAA conjugates of the present invention can be labeled with markers that will facilitate diagnostic imaging of various disease states including tumors, inflamed joints, lesions, etc. Typically, these labels will be radioactive markers, although fluorescent labels can also be used. The use of gamma-emitting radioisotopes is particularly advantageous as they can easily be counted in a scintillation well counter, do not require tissue homogenization prior to counting and can be imaged with gamma cameras.

Gamma- or positron-emitting radioisotopes are typically used, such as $^{99}$Tc, $^{24}$Na, $^{51}$Cr, $^{59}$Fe, $^{67}$Ga, $^{86}$Rb, $^{111}$In, $^{125}$I, and $^{195}$Pt as gamma-emitting; and such as $^{68}$Ga, $^{82}$Rb, $^{22}$Na, $^{75}$Br, $^{122}$I and $^{18}$F as positron-emitting. The liposomes can also be labelled with a paramagnetic isotope for purposes of in vivo diagnosis, as through the use of magnetic resonance imaging (MRI) or electron spin resonance (ESR). See, for example, U.S. Pat. No. 4,728,575, the teachings of which are incorporated herein by reference.

D. Loading the Liposomes

Methods of loading conventional drugs into liposomes include, for example, an encapsulation technique, loading into the bilayer and a transmembrane potential loading method.

In one encapsulation technique, the drug and liposome components are dissolved in an organic solvent in which all species are miscible and concentrated to a dry film. A buffer is then added to the dried film and liposomes are formed having the drug incorporated into the vesicle walls. Alternatively, the drug can be placed into a buffer and added to a dried film of only lipid components. In this manner, the drug will become encapsulated in the aqueous interior of the liposome. The buffer which is used in the formation of the liposomes can be any biologically compatible buffer solution of, for example, isotonic saline, phosphate buffered saline, or other low ionic strength buffers. Generally, the drug will be present in an amount of from about 0.01 ng/mL to about 50 mg/mL. The resulting liposomes with the drug incorporated in the aqueous interior or in the membrane are then optionally sized as described above.

Transmembrane potential loading has been described in detail in U.S. Pat. Nos. 4,885,172, 5,059,421, and 5,171,578, the contents of which are incorporated herein by reference. Briefly, the transmembrane potential loading method can be used with essentially any conventional drug which can exist in a charged state when dissolved in an appropriate aqueous medium. Preferably, the drug will be relatively lipophilic so that it will partition into the liposome membranes. A transmembrane potential is created across the bilayers of the liposomes or protein-liposome complexes and the drug is loaded into the liposome by means of the transmembrane potential. The transmembrane potential is generated by creating a concentration gradient for one or more charged species (e.g., $Na^+$, $K^+$ and/or $H^+$) across the membranes. This concentration gradient is generated by producing liposomes having different internal and external media and has an associated proton gradient. Drug accumulation can than occur in a manner predicted by the Henderson-Hasselbach equation.

The liposome compositions of the present invention can by administered to a subject according to standard techniques. Preferably, pharmaceutical compositions of the liposome compositions are administered parenterally, i.e., intraperitoneally, intravenously, subcutaneously or intramuscularly. More preferably, the pharmaceutical compositions are administered intravenously by a bolus injection. Suitable formulations for use in the present invention are found in Remington's Pharmaceutical Sciences, Mack Publishing Company, Philadelphia, Pa., 17th ed. (1985). The pharmaceutical compositions can be used, for example, to diagnose a variety of conditions, or treat a variety of disease states (such as inflammation, infection (both viral and bacterial infections), neoplasis, cancer, etc.).

Preferably, the pharmaceutical compositions are administered intravenously. Thus, this invention provides compositions for intravenous administration which comprise a solution of the liposomes suspended in an acceptable carrier, preferably an aqueous carrier. A variety of aqueous carriers can be used, e.g., water, buffered water, 0.9% isotonic saline, and the like. These compositions can be sterilized by conventional, well known sterilization techniques, or may be sterile filtered. The resulting aqueous solutions may be packaged for use as is or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of liposome compositions in the pharmaceutical formulations can vary widely, i.e., from less than about 0.05%, usually at or at least about 2-5% to as much as 10 to 30% by weight and will be selected primarily by fluid volumes, viscosities, etc., in accordance with the particular mode of administration selected. For diagnosis, the amount of composition administered will depend upon the particular label used (i.e., radiolabel, fluorescence label, and the like), the disease state being diagnosed and the judgment of the clinician, but will generally be between about 1 and about 5 mg per kilogram of body weight.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1

Synthesis of PEG-Dialkyloxypropyls (PEG-DAA's)

The following example illustrates the synthesis of three PEG-lipids, PEG-A-DMA (7), PEG-C-DMA (8), and PEG-S-DMA (9). They have a common precursor, the amine lipid 1,2-dimyristyloxypropylamine (5). This lipid has alkyl chains 14 carbon units ($C_{14}$) in length. Other PEG DAAs suitable for use in the present invention can be synthesized using similar protocols. For instance, PEG-A-DSA and PEG-C-DSA can be synthesized by using the $C_{18}$ analogue of (5). The $C_{18}$ analogue can be synthesized by simply substituting an equimolar amount of stearyl bromide for myristyl bromide in the very first step (synthesis of compound (1)).

1. Preparation of
1,2-Dimyristyloxy-3-allyloxypropane (1)

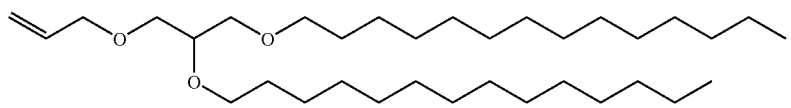

Benzene (250 ml) was added to 95% sodium hydride (11.4 g, 450.0 mmol), and the flask was flushed with nitrogen and sealed. A solution of 3-allyloxy-1,2-propanediol (6.6 g, 50.0 mmol) in benzene (75 ml) was added to the flask. Using a syringe, 97% 1-bromotetradecane (36.7 ml, 120.0 mmol) was added to the flask and the reaction was left to reflux overnight under a constant stream of nitrogen. Once cooled to room temperature, the excess sodium hydride was slowly quenched with ethanol until no further effervescence was observed. The solution was transferred to a separatory funnel with benzene (250 ml) and washed with distilled water (3×200 ml). The organic layer was dried with magnesium sulfate and the solvent removed on the rotary evaporator to yield a colourless oil. TLC (5% ether-hexane, developed in Molybdate) indicated that most of the starting material had reacted to form product. This resulting product was further purified by flash column chromatography (1-5% ether-hexane) to yield 15.0 g (57.3%) of 1,2-dimyristyloxy-3-allyloxypropane 1.

2. Preparation of 1,2-Dimyristyloxypropan-3-ol (2)

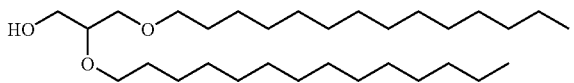

1,2-Dimyristyloxy-3-allyloxypropane 1 (15.0 g, 28.6 mmol) was dissolved in ethanol (250 ml). Trifluoroacetic acid (20 ml) was added, followed by tetrakis(triphenylphosphine)palladium(0) (4.5 g, 3.9 mmol). The flask was wrapped in tin foil and flushed with nitrogen to reduce exposure to light and air, then left to stir at 80° C. overnight. The ethanol was removed on the rotary evaporator. TLC (100% CHCl$_3$, developed in Molybdate) indicated that most of the starting material had reacted to form product. This resulting product was further purified by flash column chromatography (100% DCM) to yield 11.5 g (83.1%) 1,2-dimyristyloxypropan-3-ol 2.

3. Preparation of O-(2,3-Dimyristyloxypropyl)methanesulphonate (3)

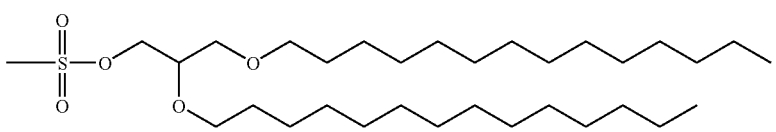

A flask containing 97% methanesulphonic anhydride (8.4 g, 48.0 mmol) was flushed with nitrogen and dissolved in anhydrous dichloromethane (50 ml). Anhydrous pyridine (3.9 ml, 48.0 mmol) was slowly added, forming a white precipitate. A solution of 1,2-dimyristyloxypropan-3-ol 15 (11.5 g, 24.0 mmol) in anhydrous dichloromethane (100 ml) was added and the reaction was left to stir overnight at room temperature. The solution was transferred to a separatory funnel with dichloromethane (100 ml) and was washed with distilled water (3×100 ml). The combined aqueous washes were then back-extracted with dichloromethane (100 ml). The combined organic layers were dried with magnesium sulfate and the dichloromethane was removed on the rotary evaporator to yield a colourless oil. TLC (100% CHCl$_3$, developed in Molybdate) indicated that the starting material had all reacted to form product. This reaction yielded 11.9 g of crude O-(2,3-dimyristyloxypropyl)methanesulphonate 3.

4. Preparation of N-(2,3-Dimyristyloxypropyl)phthalimide (4)

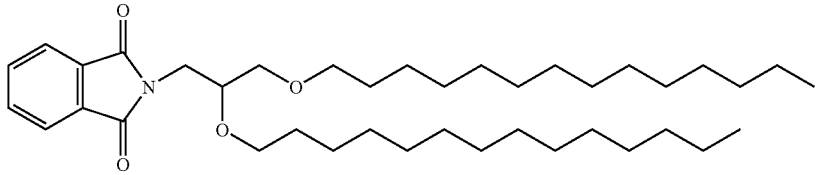

Crude O-(2,3-dimyristyloxypropyl) methanesulphonate 3 (14.2 g, 25.3 mmol) and potassium phthalimide (13.9 g, 75.0 mmol) were flushed with nitrogen and dissolved in anhydrous N,N-dimethylformamide (250 ml). The reaction was left to stir at 70° C. overnight under a constant stream of nitrogen. The N,N-dimethylformamide was removed on the rotary evaporator using a high vacuum pump instead of the usual aspirator. The residue was dissolved in chloroform (300 ml) and transferred to a separatory funnel with a chloroform rinse (50 ml), then washed with distilled water and ethanol (3×300 ml distilled water, 50 ml ethanol). The combined aqueous washes were back-extracted with chloroform (2×100 ml). The combined organic layers were dried with magnesium sulfate and the chloroform was removed on the rotary evaporator. TLC (30% ether-hexane, developed in Molybdate) indicated that the starting material had reacted to form product. This reaction yielded 13.5 g of crude N-(2,3-dimyristyloxypropyl)phthalimide 4.

5. Preparation of 1,2-Dimyristyloxypropylamine (5)

Crude N-(2,3-dimyristyloxypropyl) phthalimide 4 (20.0 g, 25.0 mmol) was dissolved in ethanol (300 ml). Hydrazine monohydrate (20 ml, 412.3 mmol) was added and the reaction was left to reflux overnight. The ethanol was removed on the rotary evaporator and the residue was redissolved in chloroform (200 ml). The precipitate was filtered off and the chloroform was removed on the rotary evaporator. TLC (10% MeOH—CHCl$_3$, developed in Molybdate) indicated that most of the starting material had reacted to form product. This resulting product was further purified by flash column chromatography (0-5% MeOH—CHCl$_3$) to yield 10.4 g (89.7% over three steps from 1,2-dimyristyloxypropan-3-ol 2) of 1,2-dimyristyloxypropylamine 5.

6. Preparation of Methoxy PEG$_{2000}$ Acetic Acid (6)

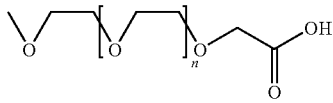

A 10% solution of concentrated sulfuric acid (20 ml) in water (180 ml) was added to sodium dichromate (3.0 g, 10 mmol). PEG$_{2000}$ methyl ether (20.0 g, 10 mmol) was dissolved in this bright orange solution and the reaction was left to stir at room temperature overnight. The product was then extracted with chloroform (3×250 ml) leaving the dark blue colour in the aqueous layer. The chloroform solvent was removed on the rotary evaporator, resulting in a pale blue wax. TLC (13% MeOH—CHCl$_3$, developed in iodine) indicated that most of the starting material had reacted to form product. This crude material was then further purified by flash column chromatography (0-15% MeOH—CHCl$_3$). The resulting product was then crystallized in ether to yield 5.6 g (27.1%) of methoxy PEG$_{2000}$ acetic acid 6 as a white solid.

7. Preparation of N-(2,3-dimyristyloxypropyl)amide PEG$_{2000}$Methyl Ether (7)

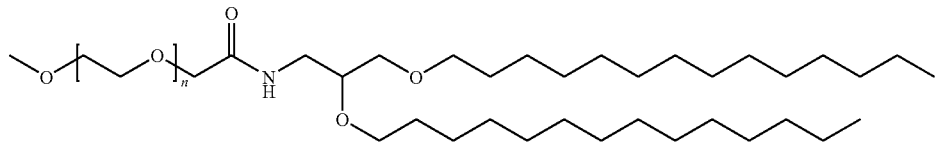

For preparation of N-(2,3-dimyristyloxypropyl)amide PEG$_{2000}$ methyl ether (i.e., PEG-A-DMA), methoxy PEG$_{2000}$ acetic acid 6 (3.4 g, 1.7 mmol) was dissolved in benzene (40 ml) and flushed with nitrogen. Oxalyl chloride (1.7 ml, 2.5 g, 20 mmol) was slowly added by a syringe and needle through the subaseal. This reaction was left to stir for 2 hours then the benzene solvent was removed on the rotary evaporator. 2,3-myristylyloxypropylamine 5 (0.87 g, 1.8 mmol) was added to the flask, followed by anhydrous dichloromethane (40 ml) and triethylamine (1.5 ml, 10 mmol). The reaction was left to stir for 48 hours. Distilled water (250 ml) was added, the solution was acidified with hydrochloric acid (1.5 ml) and shaken, and the organic layer was collected. The product was extracted from the aqueous layer with chloroform (2×65 ml). The combined organic layers were dried with magnesium sulfate. The chloroform was removed on the rotary evaporator to yield a yellow solid. TLC (10% MeOH—CHCl$_3$, developed in copper sulphate and iodine) indicated that most of the starting material had reacted to form product. This crude material was further purified by flash column chromatography (0-7% MeOH—CHCl$_3$). It was then decolourized by adding activated charcoal (2 g) and ethanol (100 ml) and allowing the mixture to rotate at 55° C. on the rotary evaporator for 30 minutes. The charcoal was filtered off and the ethanol was removed on the rotary evaporator. The product was lyophilized to yield 1.7 g (38.1%) of N-(2,3-dimyristyloxypropyl)amide PEG$_{2000}$ methyl ether 7 as a fluffy white powder.

8. Preparation of N-(2,3-dimyristyloxypropyl) carbamate PEG$_{2000}$ methyl ether (8)

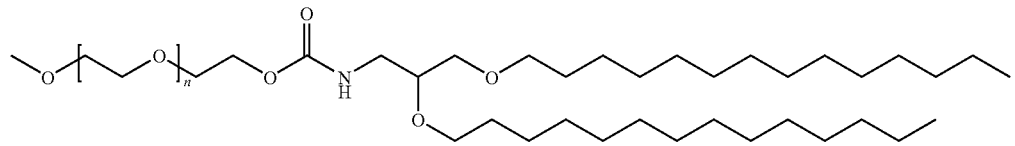

For preparation of N-(2,3-dimyristyloxypropyl) carbamate PEG$_{2000}$ methyl ether (i.e., PEG-C-DMA), steps 1-5 described above were followed. Then PEG$_{2000}$ methyl ether (2.0 g, 1.0 mmol) was flushed with nitrogen and dissolved in anhydrous dichloromethane (15 ml). Diphosgene (300 µl, 2.5 mmol) was added and the reaction was left to stir at room temperature for 3 hours. The dichloromethane was removed on the rotary evaporator and any remaining diphosgene was removed using the high vacuum pump. The flask was flushed with nitrogen and 2,3-dimyristyloxypropylamine 5 (0.7 g, 1.5 mmol) was added. This was dissolved in anhydrous dichloromethane (15 ml), triethylamine was added (280 ul), and the reaction was left to stir at room temperature overnight. The solution was transferred to a separatory funnel with dichloromethane (5 ml) and washed with distilled water (2×20 ml). The organic layer was dried with magnesium sulfate and the dichloromethane was removed on the rotary evaporator. TLC (3% MeOH-CHCl$_3$, developed in Molybdate and iodine) showed that most of the starting material had reacted to form product. This resulting product was further purified by flash column chromatography (1.5-10% MeOH-CHCl$_3$) to yield 1.2 g (46.5%) of N-(2,3-dimyristyloxypropyl) carbamate PEG$_{2000}$ methyl ether 8.

9. Preparation of N-(2,3-dimyristyloxypropyl)succinamide PEG$_{2000}$ Methyl Ether (13)

For preparation of N-(2,3-dimyristyloxypropyl) succinamide PEG$_{2000}$ methyl ether (13), steps 1-5 described above were followed. The remaining procedure follows"

a. Preparation of PEG$_{2000}$ Mesylate (9)

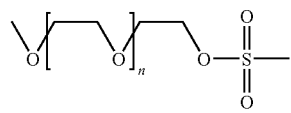

Mesyl anhydride (8.2 g, 47.1 mmol) was dissolved in anhydrous chloroform (80 ml). Pyridine (3.8 ml, 47.0 mmol) was added to the solution and fuming was observed while a white precipitate formed. A solution of PEG$_{2000}$ methyl ether (31.5 g, 15.5 mmol) in anhydrous chloroform (70 ml) was added and the reaction was left to stir for 3 hours. The white precipitate that had formed was filtered off and the chloroform solvent of the filtrate was removed on the rotary evaporator. TLC (5% MeOH—CHCl$_3$, developed in iodine) indicated that most of the starting material had reacted to form product. This product was further purified by flash column chromatography (0-10% MeOH—CHCl$_3$) to yield 30.1 g (92.8%) of PEG$_{2000}$ mesylate 9 as a white solid.

b. Preparation of PEG$_{2000}$ Phthalimide (10)

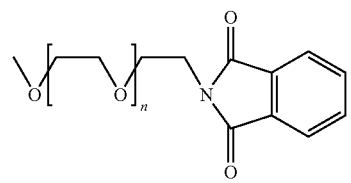

Potassium phthalimide (11.1 g, 59.7 mmol) was dissolved in anhydrous N,N-Dimethylformamide (400 ml). A solution of PEG$_{2000}$ mesylate 9 (35.0 g, 16.7 mmol) in anhydrous N,N-Dimethylformamide (100 ml) was added to the flask and the reaction was left to stir at 75° C. overnight. The N,N-Dimethylformamide solvent was removed on the rotary evaporator using a high vacuum pump instead of the usual aspirator. The resulting product was dissolved in dichloromethane (250 ml) and washed with distilled water (2×250 ml) and brine (250 ml). The dichloromethane solvent of the combined organic layers was removed on the rotary evaporator. TLC (7% MeOH—CHCl$_3$, visualized with UV light and Mary's Reagent) indicated that most of the starting material had reacted to form product. This resulting product was further purified by flash column chromatography (0-10% MeOH—CH$_2$Cl$_2$). The product was crystallized from ether to yield 19.4 g (54.1%) of the PEG$_{2000}$ phthalimide 10.

c. Preparation of PEG$_{2000}$ Amine (11)

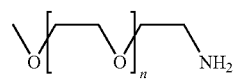

PEG$_{2000}$ phthalimide 10 (10.3 g, 4.8 mmol) was dissolved in ethanol (200 ml). Hydrazine monohydrate (6.0 ml, 123.7 mmol) was slowly added and the reaction was left to reflux at 100° C. overnight. The white precipitate was filtered off and the ethanol solvent was removed on the rotary evaporator. The resulting product was dissolved in chloroform and the remaining white solid that was insoluble in the chloroform was filtered off and again the chloroform was removed on the rotary evaporator. TLC (10% MeOH—CHCl$_3$, developed in iodine, Molybdate and Mary's Reagent) indicated that all the starting material had reacted to form product. This product was then crystallized from ether to yield 9.0 g (93.0%) of PEG$_{2000}$ amine 11 as a white powder.

d. Preparation of PEG$_{2000}$ Succinamide (12)

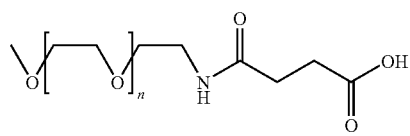

PEG$_{2000}$ amine 11 (9.0 g, 4.4 mmol) and succinic anhydride (3.8 g, 38.1 mmol) were dissolved in pyridine (100 ml) and the reaction was left to stir overnight. The pyridine solvent was removed on the rotary evaporator at 60° C. The residue was dissolved in distilled water (100 ml), acidified with hydrochloric acid, extracted with dichloromethane (100 ml, 2×70 ml), and dried with magnesium sulfate. TLC (10% MeOH—CHCl$_3$, developed in iodine) indicated that most of the starting material had reacted to form product. This product was further purified by flash column chromatography (0-10% MeOH—CHCl$_3$) to yield 5.2 g (55.9%) of PEG$_{2000}$ succinamide 12.

e. Preparation of N-(2,3-dimyristyloxypropyl)succinamide PEG$_{2000}$ Methyl Ether (13)

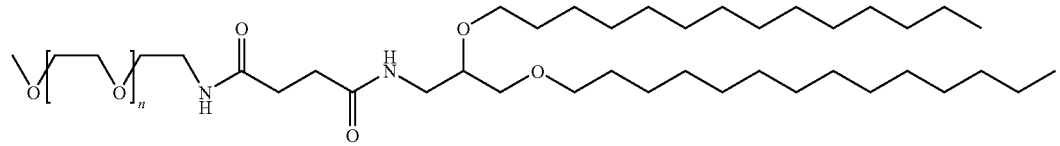

PEG$_{2000}$ succinamide (2.0 g, 0.9 mmol) and N-hydroxysuccinamide (0.2 g, 2.0 mmol) were dissolved in anhydrous chloroform (10 ml). Then, a solution of 1,3-Dicyclohexylcarbodiimide (0.3 g, 1.5 mmol) in anhydrous chloroform (5 ml) was added, and the reaction was left to stir for an hour. A solution of 1,2-dimyristyloxypropylamine 5 (0.48 g, 1.0 mmol) in anhydrous chloroform (5 ml) and triethylamine (0.6 ml, 4 mmol) was added and the reaction was left to stir for an hour. TLC (12% MeOH—CHCl$_3$, developed in Molybdate) indicated that most of the starting material had reacted to form product. The solution was filtered through Celite with dichloromethane, acidified with hydrochloric acid, and washed with distilled water (2×50 ml) and brine (50 ml). The aqueous layers were back extracted with dichloromethane (50 ml) and the combined organic layers were dried over magnesium sulfate. The product was further purified my flash column chromatography (0-7% MeOH—CHCl$_3$) to yield 1.8 g (69.0%) of N-(2,3-dimyristyloxypropyl) succinamide PEG$_{2000}$ methyl ether 13.

Figure 2:
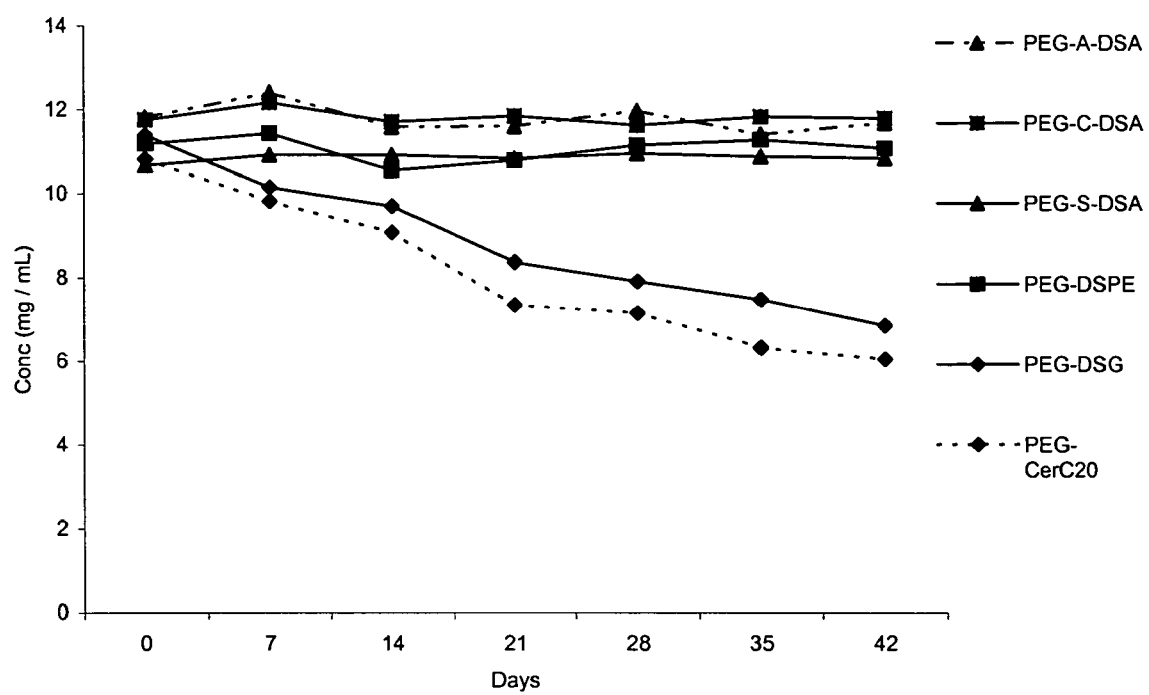
FIG. 2 illustrates data showing the stability of liposomes comprising PEG-DAA conjugates, PEG-DAG conjugates, PEG-ceramide conjugates, and PEG-DSPE conjugates.

To test their stability, each of the C$_{18}$ PEG-lipids were formulated into empty liposomes and stored in a 37° C. incubator for 42 days. The liposomes contained the following lipids with relevant molar ratios in brackets: Cholesterol (55%), 1,2-Dioleyloxy-N,N-dimethyl-3-aminopropane (15%), 1,2-distearoyl-sn-glycero-3-phosphocholine (20%), PEG-Lipid (10%). Also, PEG-CerC$_{20}$ and commercially made PEG-DSPE were formulated, while PEG-DSG was formulated as a control. At different time points, aliquots of each sample were removed from the incubator, diluted with ethanol and analyzed by HPLC to determine the concentration of the specific PEG$_{2000}$ lipid present. An Evaporative Light-Scattering Detector was used as the method of detection. The results are shown in FIG. 2.

Example 2

Expression of Nucleic Acids Encapsulated in SPLP Comprising PEG-dialkyloxypropyl Conjugates This example describes experiments comparing expression of nucleic acids encapsulated in SPLP comprising PEG-diacylglycerol conjugates versus SPLP comprising PEG-dialkyloxypropyl conjugates. All SPLP formulations comprise a plasmid encoding luiferase under the control of the CMV promoter (pLO55).

| Group | # Mice | Cell | Route | Treatment | Route | # Doses | Time after final injection | Assay* |
|---|---|---|---|---|---|---|---|---|
| A | 6 | Neuro-2a | SC | PBS | IV | 1 | 48 hrs | Body weights, |
| B | 6 | Neuro-2a | SC | SPLP PEG-DSG | IV | 1 | 48 hrs | Blood analyses, Luciferase |
| C | 6 | Neuro-2a | SC | SPLP PEG-DSPE | IV | 1 | 48 hrs | activity |
| D | 6 | Neuro-2a | SC | SPLP PEG-CeramideC20 | IV | 1 | 48 hrs | |
| E | 6 | Neuro-2a | SC | SPLP PEG-A-DSA | IV | 1 | 48 hrs | |
| F | 6 | Neuro-2a | SC | SPLP PEG-C-DSA | IV | 1 | 48 hrs | |
| G | 6 | Neuro-2a | SC | SPLP PEG-S-DSA | IV | 1 | 48 hrs | |

All SPLP formulations contained pL055 and DSPC:Chol:DODMA:PEG-Lipid (20:55:15:10). The following formulations were made:

| Group | No. Mice | Seeding date | Treatment | Injection date | Collection date |
|---|---|---|---|---|---|
| A | 6 | Day 0 | PBS | Day 13 | Day 15 |
| B | 6 | Day 0 | SPLP PEG-DSG | Day 13 | Day 15 |
| C | 6 | Day 0 | SPLP PEG-DSPE | Day 13 | Day 15 |

-continued

| Group | No. Mice | Seeding date | Treatment | Injection date | Collection date |
|---|---|---|---|---|---|
| D | 6 | Day 0 | SPLP PEG-CeramideC20 | Day 13 | Day 15 |
| E | 6 | Day 0 | SPLP PEG-A-DSA | Day 13 | Day 15 |
| F | 6 | Day 0 | SPLP PEG-C-DSA | Day 13 | Day 15 |
| G | 6 | Day 0 | SPLP PEG-S-DSA | Day 13 | Day 15 |

A: PBS (pH 7.4).
B: L055 PEG-DSG SPLP, 0.50 mg/ml.
C: L055 PEG-DSPE SPLP, 0.50 mg/ml.
D: L055 PEG-CeramideC20 SPLP, 0.50 mg/ml.
E: L055 PEG-A-DSA SPLP, 0.50 mg/ml.
F: L055 PEG-C-DSA SPLP, 0.50 mg/ml.
G: L055 PEG-S-DSA SPLP, 0.50 mg/ml.

$1.5 \times 10^6$ Neuro2A cells in 50 µl PBS were subcutaneously administered to each mouse on day 0. On day 13, mice were randomized and treated with one dose of an SPLP formulation or PBS by intravenous (IV) injection. Dose amounts are based on body weight measurements taken on the day of dosing. 48 hours after SPLP administration, the mice were weighed and sacrificed, their blood was collected, and the following tissues were collected, weighed, immediately frozen and stored at −80° C. until further analysis: tumor, liver (cut in 2 halves), lungs, spleen and heart.

Figure 3:
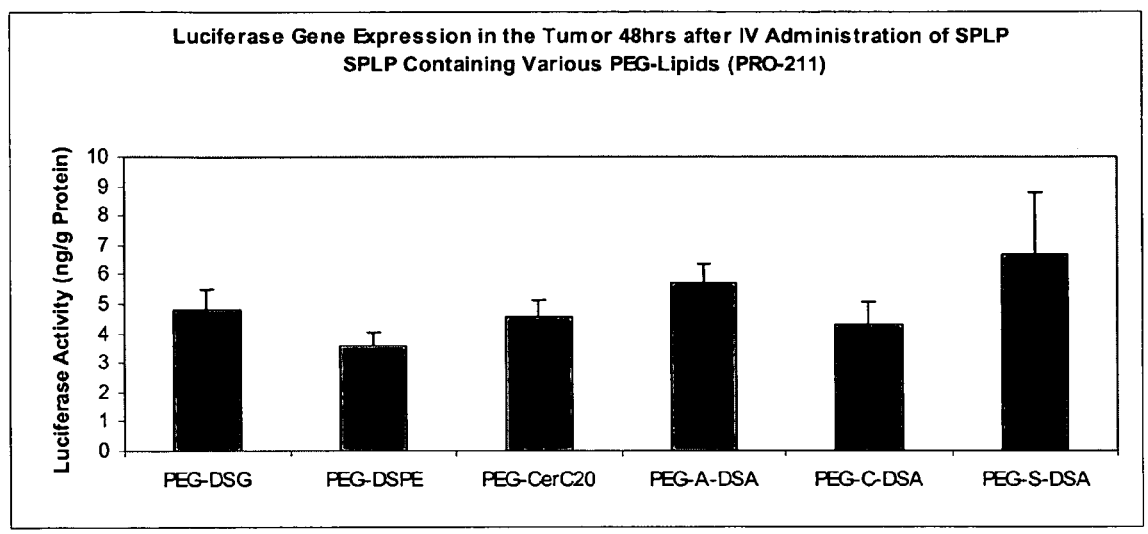
FIG. 3 illustrates data showing luciferase gene expression in tumors following IV administration of SPLP comprising PEG-DAA conjugates, PEG-DAG conjugates, and PEG-ceramide conjugates.
Figure 4:
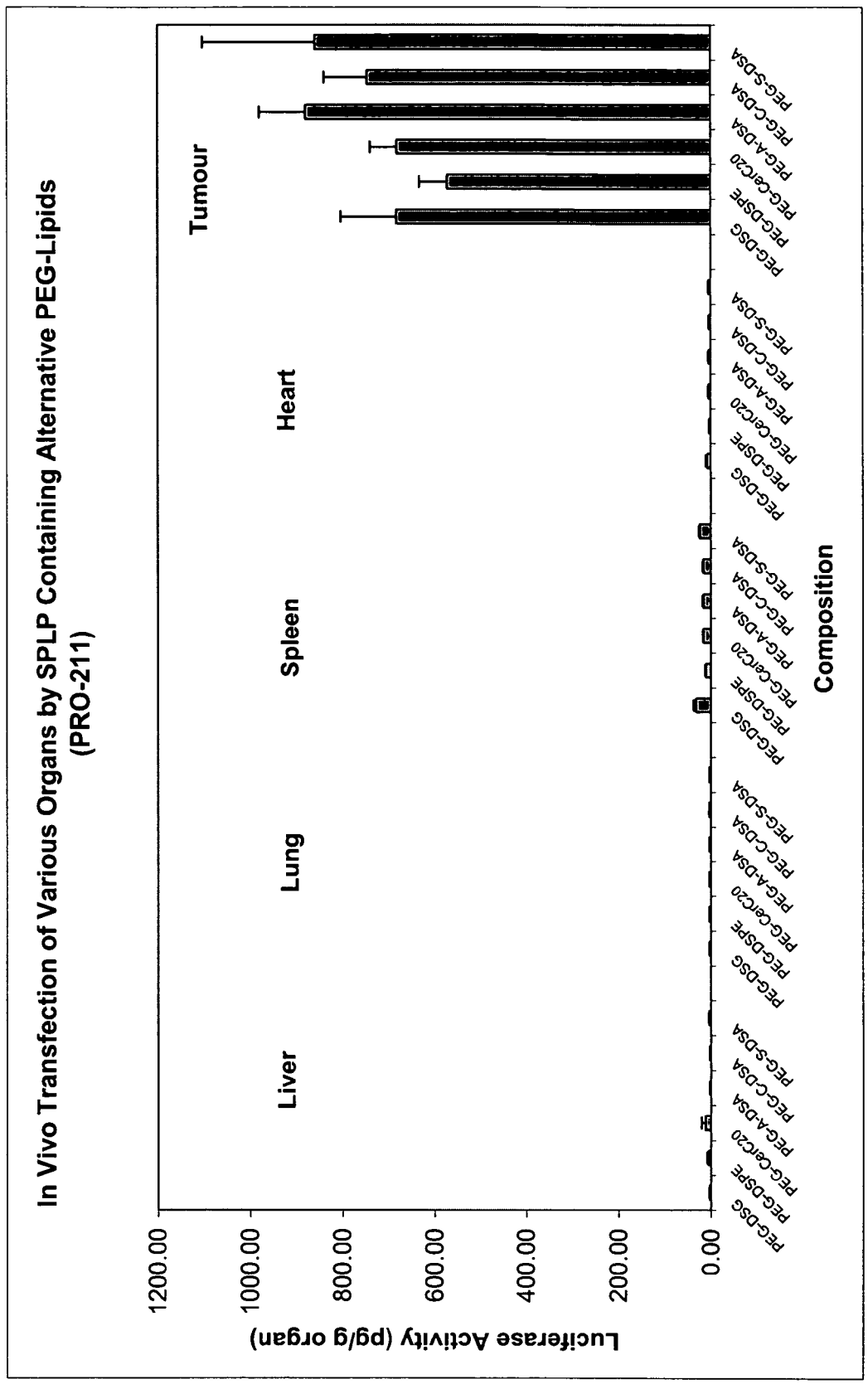
FIG. 4 illustrates data showing in vivo transfection by SPLP comprising PEG-DAA conjugates, PEG-DAG conjugates, PEG-ceramide conjugates, and PEG-DSPE conjugates.

Gene expression in collected tissues was determined by assaying for enzymatic activity of expressed luciferase reporter protein. The results are shown in FIGS. 3 and 4.

The results demonstrate that 48 hours following i.v. injection of the SPLP, the transfection levels in the tumor by the SPLP comprising PEG-dialkyloxypropyl conjugates are substantially similar to those by SPLP comprising PEG-diacylglycerol conjugates. The amount of gene expression in the organs (liver, lung, spleen, and heart) of the mice injected with the SPLP comprising PEG-dialkyloxypropyl conjugates is also substantially similar to that of SPLP comprising PEG-diacylglycerol conjugates.

Example 3

Expression of Nucleic Acids Encapsulated in SPLP Comprising PEG-dialkyloxypropyl Conjugates This examples describes experiments comparing expression of nucleic acids encapsulated in SPLP comprising PEG-dialkyloxypropyl conjugates. All SPLP formulations comprise a plasmid encoding luiferase under the control of the CMV promoter (pLO55)

| Group | # Mice | Tumor | Route | Treatment | Route | # Doses | Timepoint | ASSAY*** |
|---|---|---|---|---|---|---|---|---|
| A | 4 | Neuro-2a | SC | PBS | IV | 1 | 48 hrs | Body weights, Blood analyses, Luciferase activity |
| B | 5 | Neuro-2a | SC | SPLP PEG-DSG | IV | 1 | 48 hrs | |
| C | 5 | Neuro-2a | SC | SPLP PEG-A-DSA | IV | 1 | 48 hrs | |
| D | 5 | Neuro-2a | SC | SPLP PEG-A-DPA | IV | 1 | 48 hrs | |
| E | 5 | Neuro-2a | SC | SPLP PEG-A-DMA | IV | 1 | 48 hrs | |

The lipids (DSPC:CHOL:DODMA:PEG-Lipid) were present in the SPLP in the following molar ratios (20:55:15:10). The following formulations were made:

| Group | # Mice | Seeding date | Treatment | Injection date | Collection date |
|---|---|---|---|---|---|
| A | 4 | Day 0 | PBS | Day 12 | Day 14 |
| B | 5 | Day 0 | SPLP PEG-DSG | Day 12 | Day 14 |
| C | 5 | Day 0 | SPLP PEG-A-DSA | Day 12 | Day 14 |
| D | 5 | Day 0 | SPLP PEG-A-DPA | Day 12 | Day 14 |
| E | 5 | Day 0 | SPLP PEG-A-DMA | Day 12 | Day 14 |

A: PBS sterile filtered, 5 mL.
B: pL055-SPLP with PEG-DSG, 2 mL at 0.50 mg/mL.
C: pL055-SPLP with PEG-A-DSA, 2 mL at 0.50 mg/mL.
D: pL055-SPLP with PEG-A-DPA, 2 mL at 0.50 mg/mL.
E: pL055-SPLP with PEG-A-DMA, 2 mL at 0.50 mg/mL.

$1.5 \times 10^6$ Neuro2A cells were administered to each mouse on day 0. When the tumors were of a suitable size (200-400 mm$^3$), mice were randomized and treated with one dose of an SPLP formulation or PBS by intravenous (IV) injection. Dose amounts are based on body weight measurements taken on the day of dosing. 48 hours after SPLP administration, the mice were sacrificed, their blood was collected, and the following tissues will be collected weighed, immediately frozen and stored at −80° C. until further analysis: tumor, liver (cut in 2 halves), lungs, spleen & heart.

Figure 5:
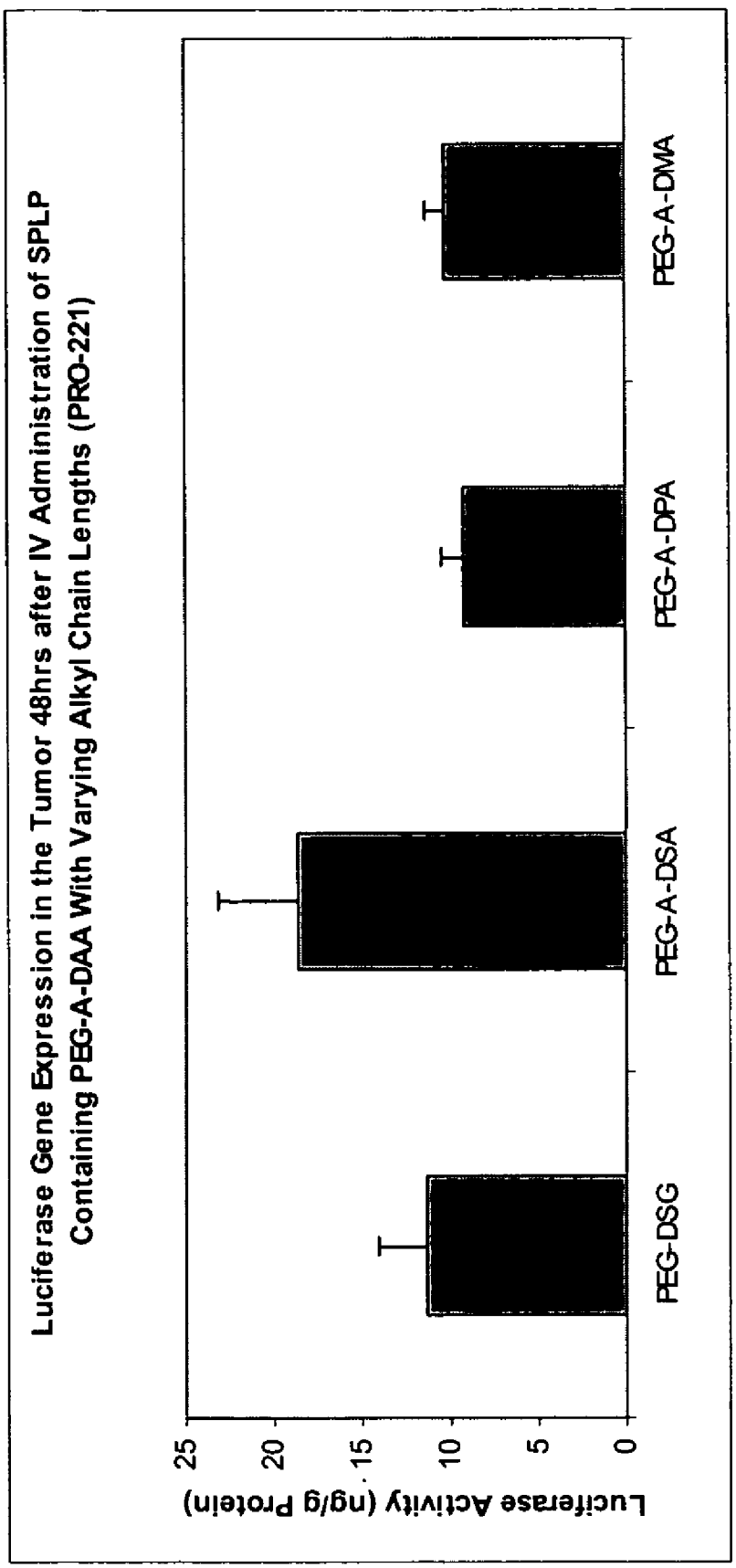
FIG. 5 illustrates data showing luciferase gene expression in tumors 48 hours after intravenous administration of SPLP comprising PEG-DAA conjugates and PEG-DAG conjugates.
Figure 6:
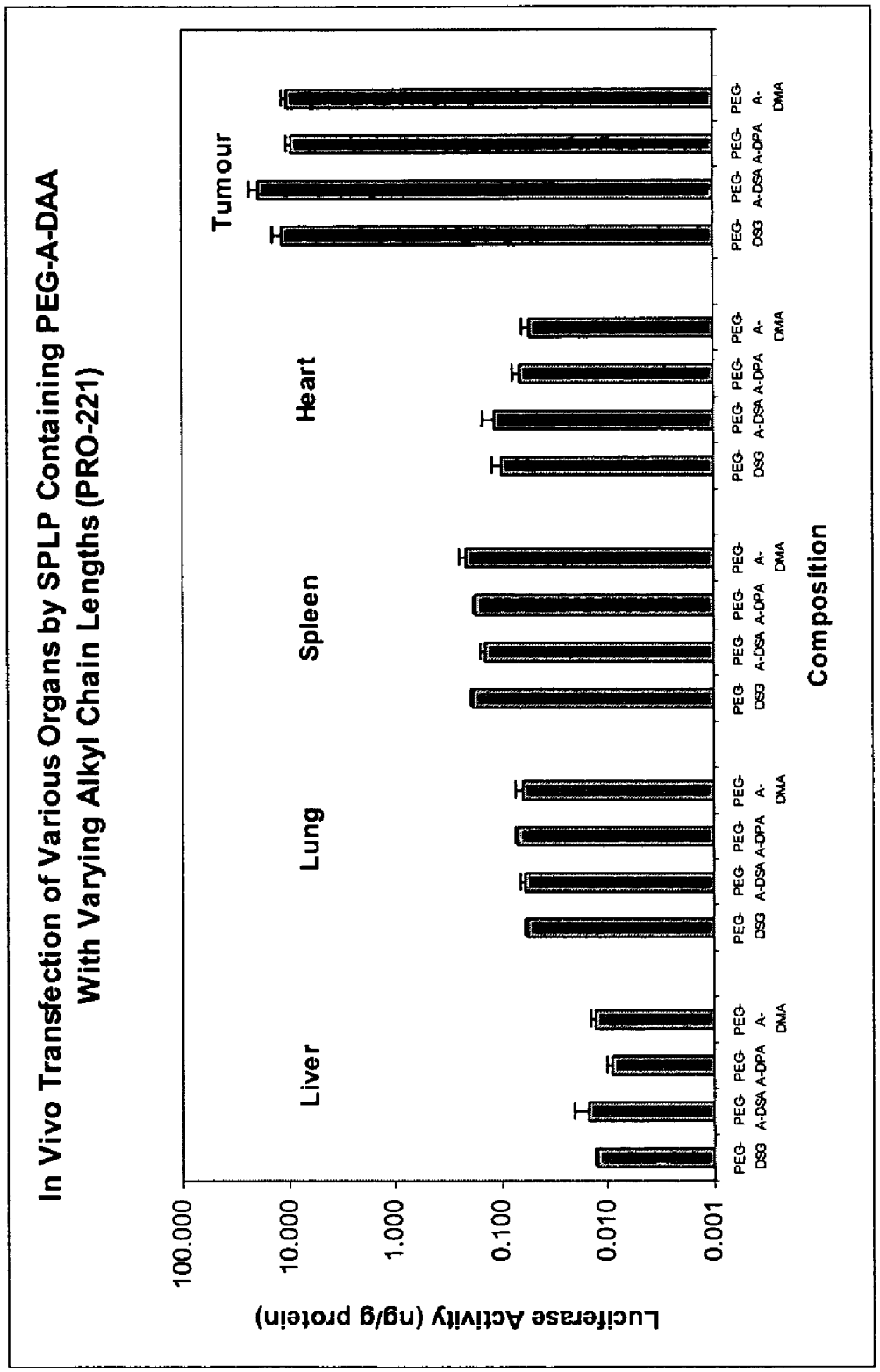
FIG. 6 illustrates data showing luciferase gene expression in liver, lung, spleen, heart, and tumor following intravenous administration of SPLP comprising PEG-DAA conjugates and PEG-DAG conjugates.

Gene expression in collected tissues was determined by assaying for enzymatic activity of expressed luciferase reporter protein. The results are shown in FIGS. 5 and 6.

The results indicate that SPLP comprising PEG-dialkyloxypropyls (i.e., PEG-DAA) can conveniently be used to transfect distal tumor to substantially the same extent as SPLP comprising PEG-diacylglycerols. Moreover, the transfection levels seen with SPLP containing PEG-dialkyglycerols are similar to those seen with SPLP containing PEG-diacylglycerols (e.g. PEG-DSG). The results also demonstrate that very little transfection occurred in non-tumor tissues. Moreover, the SPLP comprising PEG-dialkyloxypropyls exhibit reduced toxicity compared to other SPLP formulations.

Example 4

Expression of Nucleic Acids Encapsulated in SPLP and pSPLP Comprising PEG-dialkyloxypropyl Conjugates This example describes experiments comparing expression of nucleic acids encapsulated in SPLP comprising PEG-dialkyloxypropyls versus PEI condensed DNA (pSPLP) in comparison to the SPLP.

| Group | # Mice | Cell | Treatment | Route | Timepoint after final injection | Assay* |
|---|---|---|---|---|---|---|
| A | 4 | SC Neuro-2a | 1 dose PBS | IV | 48 hrs | Luciferase activity |
| B | 4 | SC Neuro-2a | 1 dose L055-pSPLP PEG-DSG | IV | 48 hrs | |
| C | 4 | SC Neuro-2a | 1 dose L055-pSPLP PEG-DPG | IV | 48 hrs | |
| D | 4 | SC Neuro-2a | 1 dose L055-pSPLP PEG-DMG | IV | 48 hrs | |
| E | 4 | SC Neuro-2a | 1 dose L055-pSPLP PEG-A-DSA | IV | 48 hrs | |
| F | 4 | SC Neuro-2a | 1 dose L055-pSPLP PEG-A-DPA | IV | 48 hrs | |
| G | 4 | SC Neuro-2a | 1 dose L055-pSPLP PEG-A-DMA | IV | 48 hrs | |
| H | 4 | SC Neuro-2a | 1 dose L055-SPLP PEG-A-DSA | IV | 48 hrs | |
| I | 4 | SC Neuro-2a | 1 dose L055-SPLP PEG-A-DPA | IV | 48 hrs | |
| J | 4 | SC Neuro-2a | 1 dose L055-SPLP PEG-A-DMA | IV | 48 hrs | |
| K | 4 | SC Neuro-2a | 1 dose L055-SPLP PEG-A-DMA at 20 mg pDNA/Kg | IV | 48 hrs | |

All formulations contained DSPC:Chol:DODMA:PEG-DAG (20:55:15:10). The following formulations were made:
A: PBS (pH 7.4).
B: L055 PEG-DSG pSPLP, 0.5 mg/ml.
C: L055 PEG-DPG pSPLP, 0.43 mg/ml.
D: L055 PEG-DMG pSPLP, 0.5 mg/ml.
E: L055 PEG-A-DSA pSPLP, 0.5 mg/ml.
F: L055 PEG-A-DPA pSPLP, 0.5 mg/ml.
G: L055 PEG-A-DMA pSPLP, 0.5 mg/ml.
H: L055 PEG-A-DSA SPLP, 0.5 mg/ml.
I: L055 PEG-A-DPA SPLP, 0.5 mg/ml.
J: L055 PEG-A-DMA SPLP, 0.5 mg/ml.
K: L055 PEG-A-DMA SPLP, 2.1 mg/ml.

$1.5 \times 10^6$ Neuro2A cells in 50 µl PBS were subcutaneously administered to each mouse on day 0. On day 13, mice were randomized and treated with one dose of an SPLP formulation or PBS by intravenous (IV) injection. Dose amounts are based on body weight measurements taken on the day of dosing. 48 hours after SPLP administration, the mice were weighed and sacrificed, their blood was collected, and the following tissues were collected, weighed, immediately frozen and stored at −80° C. until further analysis: tumor, liver (cut in 2 halves), lungs, spleen and heart.

Figure 7:
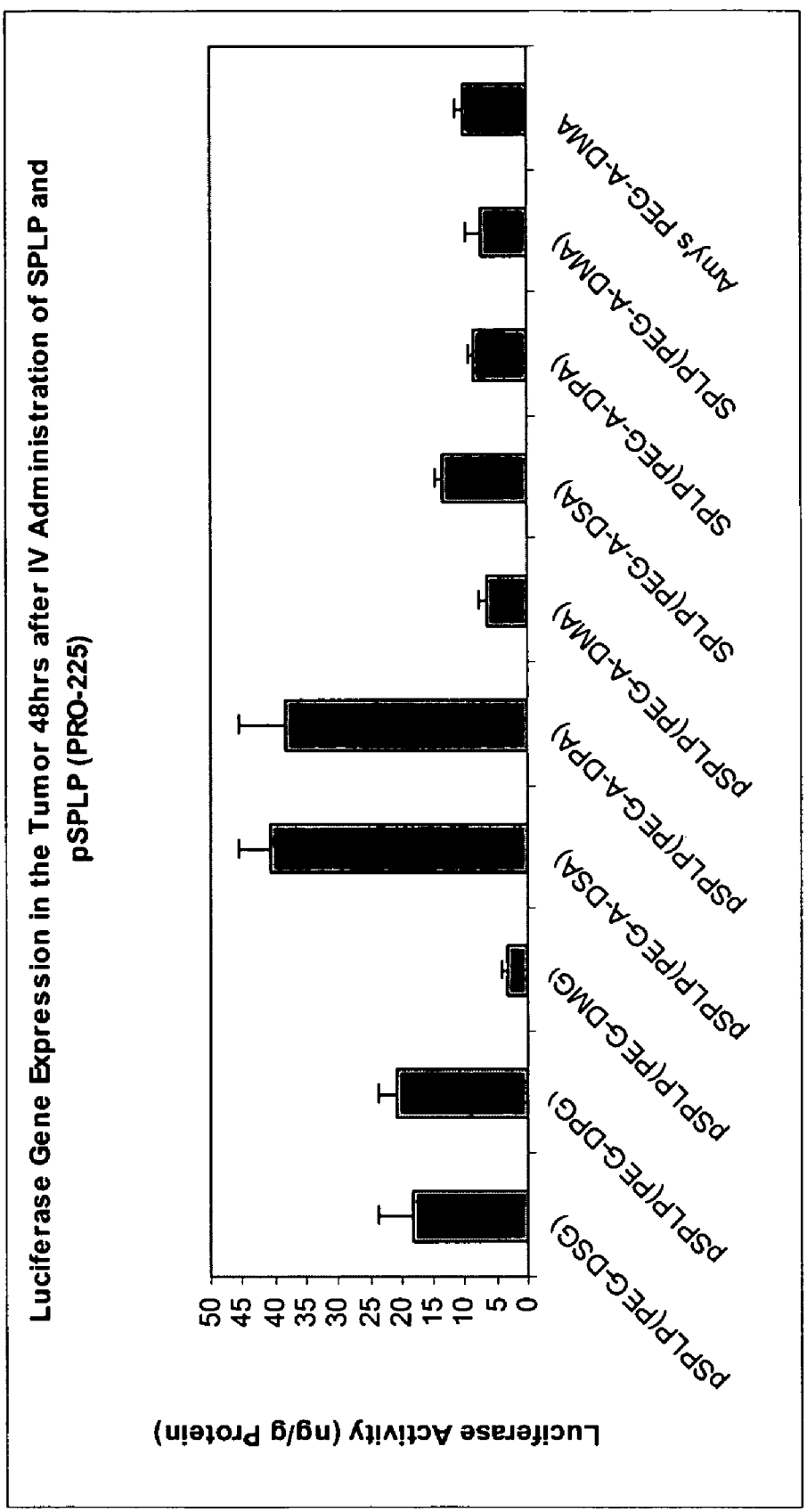
FIG. 7 illustrates data showing luciferase gene expression in tumors 48 hours after intravenous administration of SPLP or pSPLP comprising PEG-DAA conjugates and PEG-DAG conjugates.
Figure 8:
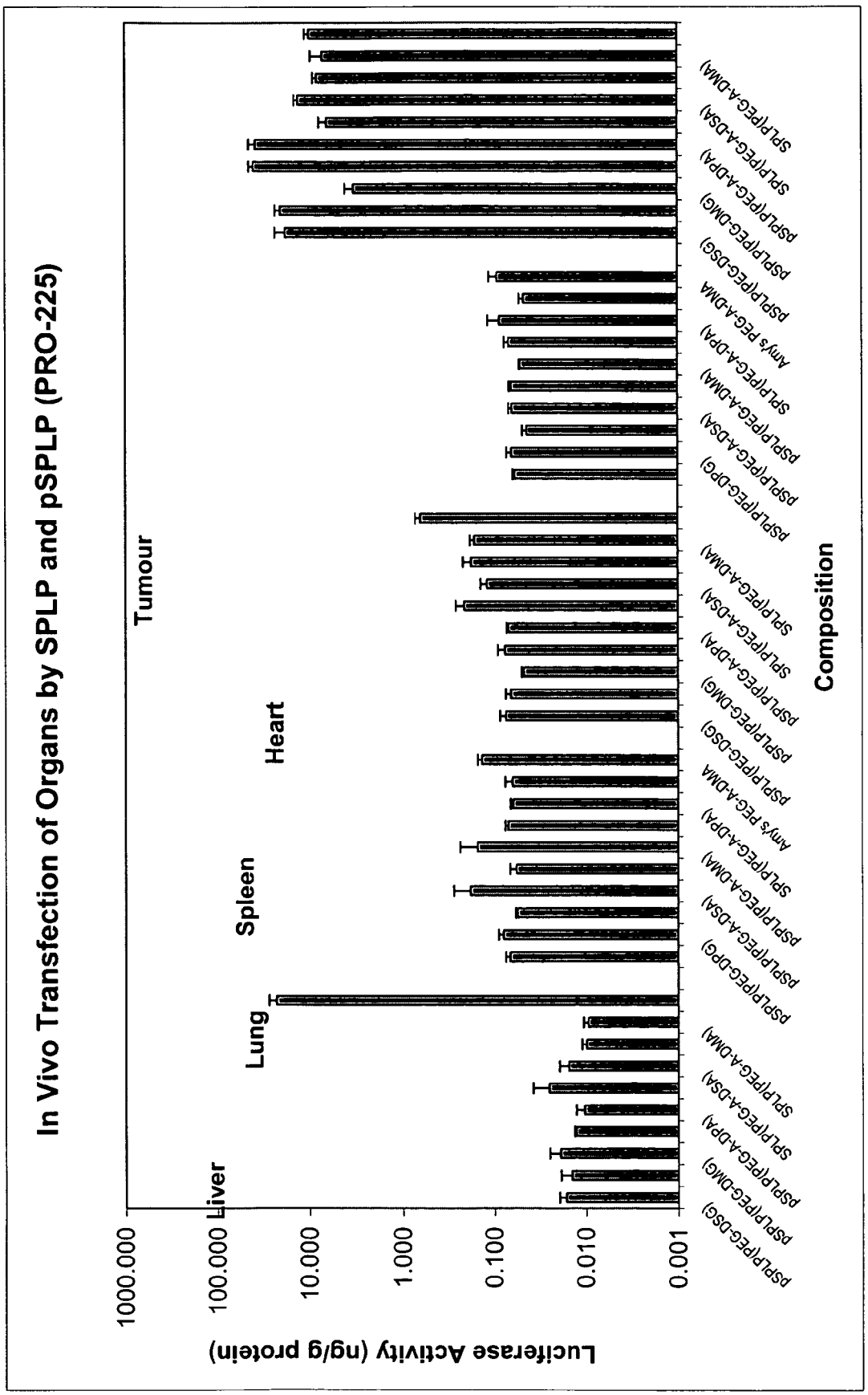
FIG. 8 illustrates data showing in vivo transfection by SPLP comprising PEG-DAA conjugates and PEG-DAG conjugates.
Figure 9:
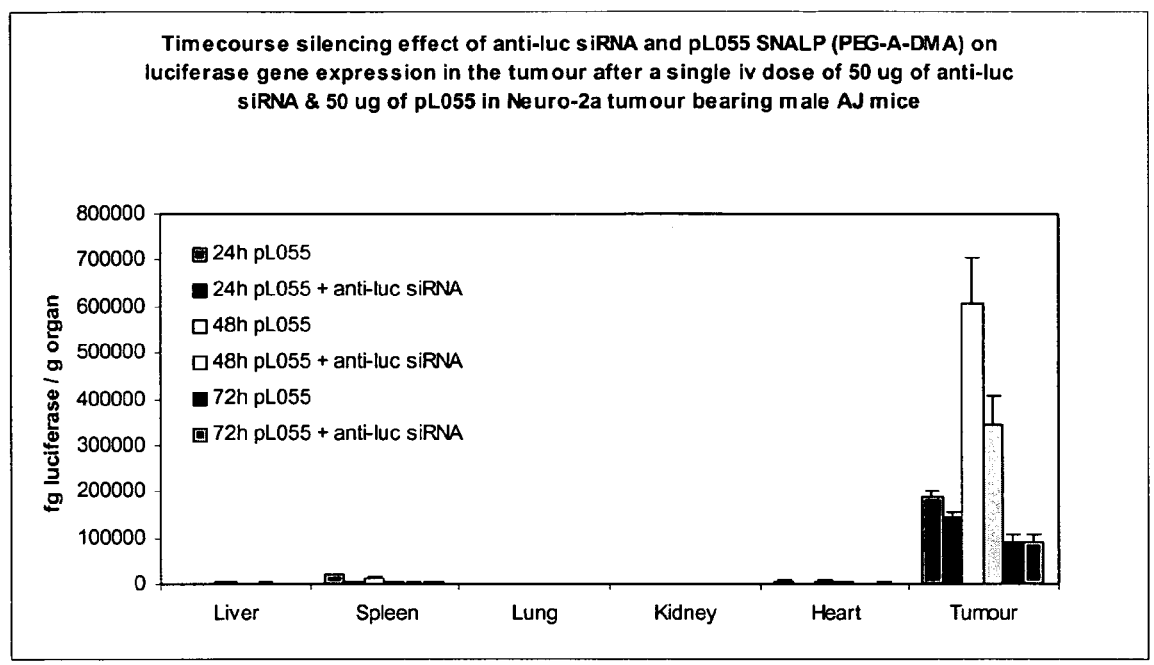
FIG. 9 illustrates in vivo data demonstrating silencing of luciferase expression in Neuro-2a tumor bearing male A/J mice treated with SPLPs comprising a PEG-DAA conjugate and containing a plasmid encoding luciferase under the control of the CMV promoter and SNALPs comprising a PEG-DAA conjugate and containing anti-luciferase siRNA.
Figure 10:
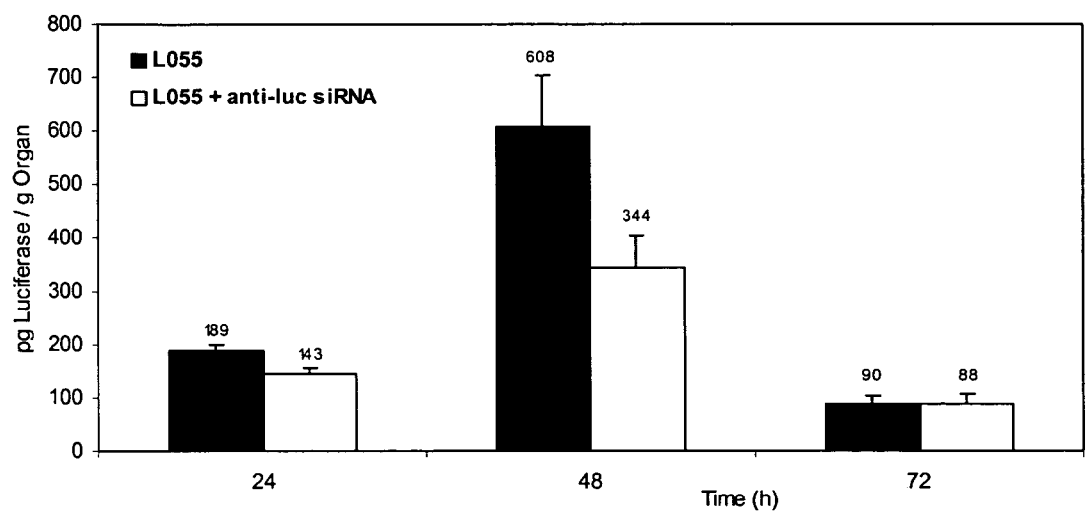
FIG. 10 illustrates in vivo data demonstrating silencing of luciferase expression in Neuro-2a tumor bearing male A/J mice treated with SPLPs comprising a PEG-DAA conjugate and containing a plasmid encoding luciferase under the control of the CMV promoter and SNALPs comprising a PEG-DAA conjugate and containing anti-luciferase siRNA.
Figure 11:
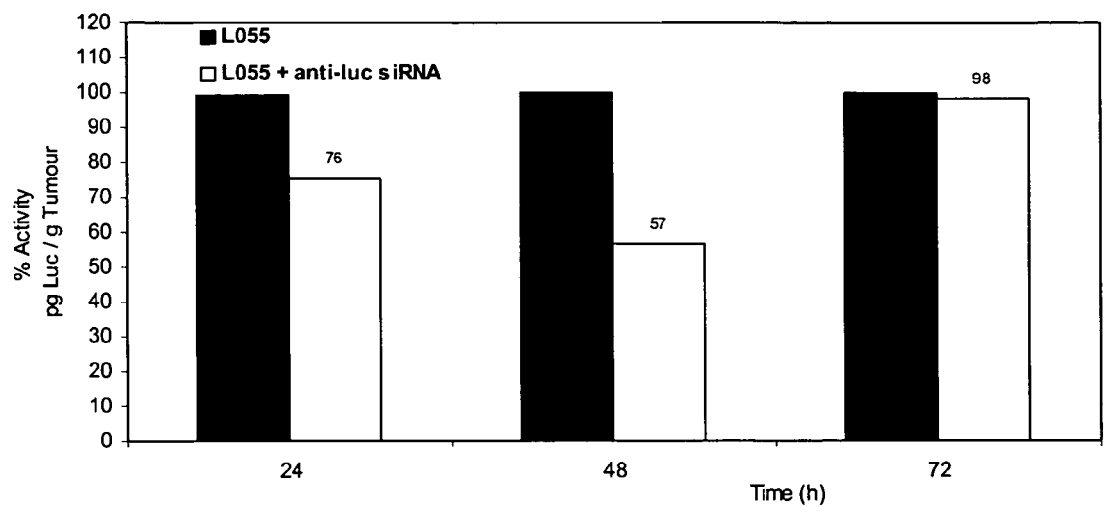
FIG. 11 illustrates in vivo data demonstrating silencing of luciferase expression in Neuro-2a tumor bearing male A/J mice treated with SPLPs comprising a PEG-DAA conjugate and containing a plasmid encoding luciferase under the control of the CMV promoter and SNALPs comprising a PEG-DAA conjugate and containing anti-luciferase siRNA.
Figure 12:
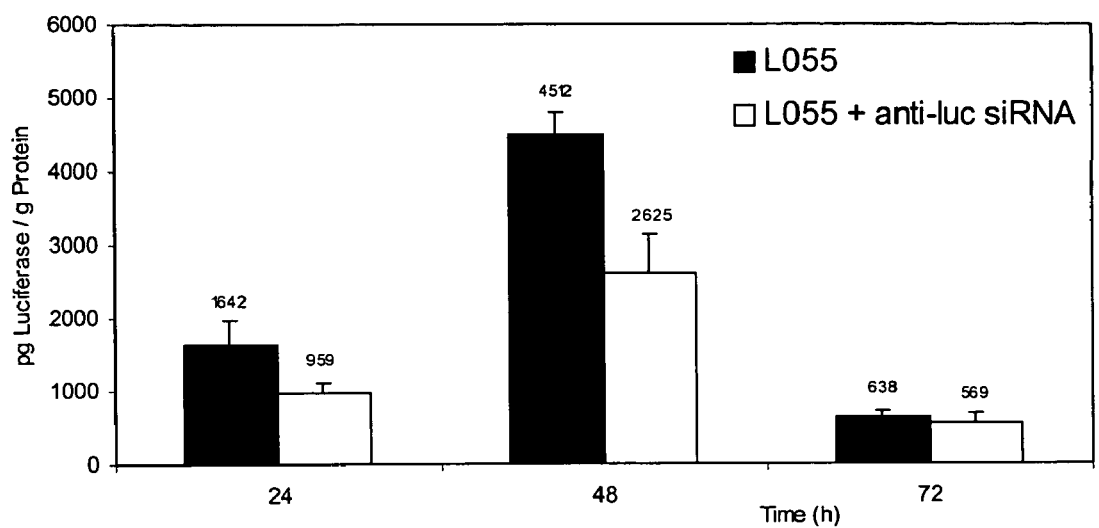
FIG. 12 illustrates in vivo data demonstrating silencing of luciferase expression in Neuro-2a tumor bearing male A/J mice treated with SPLPs comprising a PEG-DAA conjugate and containing a plasmid encoding luciferase under the control of the CMV promoter and SNALPs comprising a PEG-DAA conjugate and containing anti-luciferase siRNA.
Figure 13:
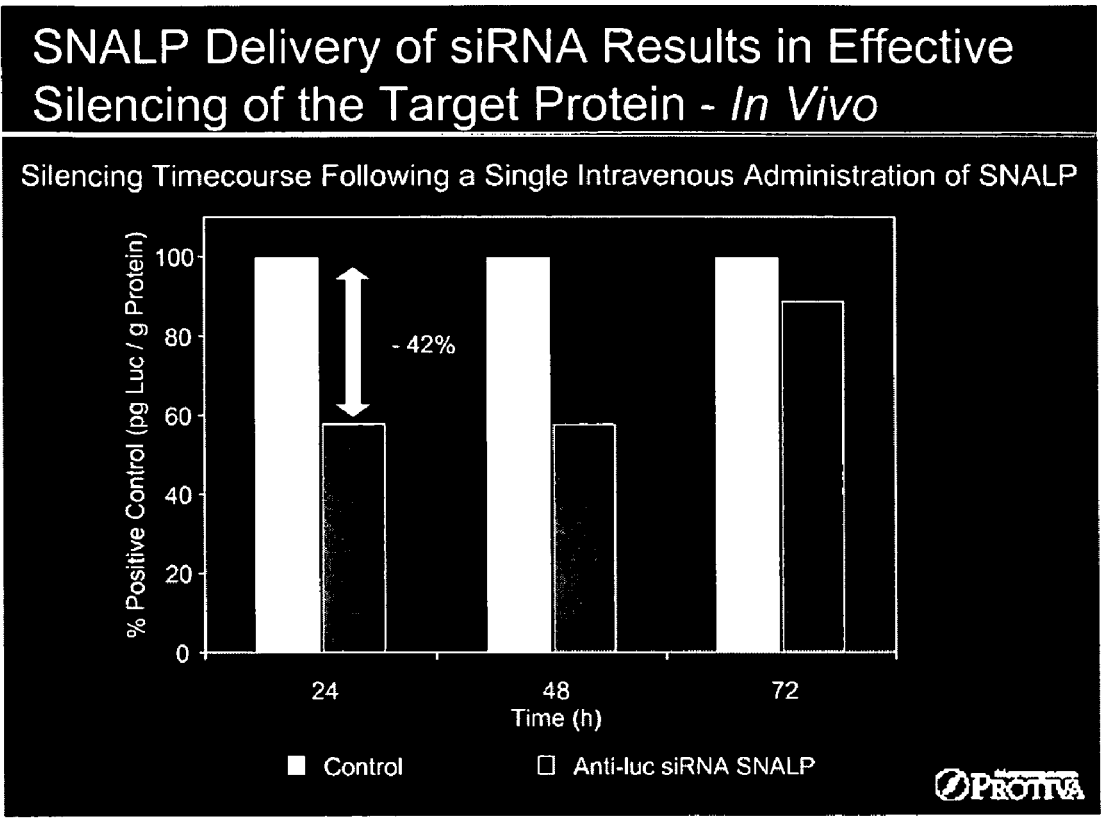
FIG. 13 illustrates in vivo data demonstrating silencing of luciferase expression in Neuro-2a tumor bearing male A/J mice treated with SPLPs comprising a PEG-DAA conjugate and containing a plasmid encoding luciferase under the control of the CMV promoter and SNALPs comprising a PEG-DAA conjugate and containing anti-luciferase siRNA.

Gene expression in collected tissues was determined by assaying for enzymatic activity of expressed luciferase reporter protein. The results are shown in FIGS. 7 and 8.

| Group | No. Mice | Tumor SC | SPLP Treatments | Termination |
|---|---|---|---|---|
| A | 4 | Day 0 | Day 12 | Day 14 |
| B | 4 | Day 0 | Day 12 | Day 14 |
| C | 4 | Day 0 | Day 12 | Day 14 |
| D | 4 | Day 0 | Day 12 | Day 14 |
| E | 4 | Day 0 | Day 12 | Day 14 |
| F | 4 | Day 0 | Day 12 | Day 14 |
| G | 4 | Day 0 | Day 12 | Day 14 |
| H | 4 | Day 0 | Day 12 | Day 14 |

-continued

| Group | No. Mice | Tumor SC | SPLP Treatments | Termination |
|---|---|---|---|---|
| I | 4 | Day 0 | Day 12 | Day 14 |
| J | 4 | Day 0 | Day 12 | Day 14 |

The results indicate that the presence of the short chain PEG-lipids (i.e. PEG-DMG and PEG-A-DMA) in pSPLP results in an approximate 5-10 fold decrease in tumor transfection compared to the long chained versions (i.e. PEG-DSG and PEG-A-DSA). Taken together these results indicate that the enhancement in tumor transfection seen with the pSPLP ($C_{18}$ PEG-lipids) over the SPLP is completely abolished when the pSPLP contains the $C_{14}$ PEG-lipids. This could be due to a number of factors: (1) a decrease in stability of the pSPLP when the PEG-lipid leaves the bilayer of the pSPLP, (2) an increase in charge upon PEG-lipid removal, or (3) the conditions for the C14 PEG-lipids have not been optimized (e.g. amount of anionic lipid in the bilayer). Further experiments will need to be performed to determine which of these if any is the issue. Also, the activities in the other organs tested were quite low for all the systems. Interestingly, a 20 mg/kg dose of PEG-A-DMA SPLP gave comparable levels of luciferase gene expression in the tumor as the 5 mg/kg dose, but much higher gene expression in the liver compared to the same 5 mg/kg dose.

Example 5

Silencing of Gene Expression with SNALPS

This example illustrates silencing of gene expression in Neuro 2A tumor bearing mice after co-administration of SPLPs containing a plasmid encoding luciferase under the control of the CMV promoter and SNALPs containing anti-luciferase siRNA.

| Group | # Mice | Tumor | Route | Treatment | Timepoint | Route | # Doses |
|---|---|---|---|---|---|---|---|
| 1 | 3 | Neuro-2a | SQ | PBS/PBS | 48 h | IV | 1 |
| 24A | 4 | | | L055-SPLP/PBS mix | 24 h | | |
| 24B | 4 | | | L055-SPLP/anti-luc siRNA liposomes mix | | | |
| 48A | 4 | | | L055-SPLP/PBS mix | 48 h | | |
| 48B | 4 | | | L055-SPLP/anti-luc siRNA liposomes mix | | | |
| 72A | 4 | | | L055-SPLP/PBS mix | 72 h | | |
| 72B | 4 | | | L055-SPLP/anti-luc siRNA liposomes mix | | | |

| Group | # Mice | Seeding Date | Route | IV Treatment | Timepoint | Injection date | Collection Date |
|---|---|---|---|---|---|---|---|
| 1 | 3 | Day 0 | SQ | PBS/PBS | 48 h | Day 13 | Day 15 |
| 24A | 4 | | | L055-SPLP/PBS mix | 24 h | Day 14 | |
| 24B | 4 | | | L055-SPLP/anti-luc siRNA liposomes mix | | Day 14 | |
| 48A | 4 | | | L055-SPLP/PBS mix | 48 h | Day 13 | |
| 48B | 4 | | | L055-SPLP/anti-luc siRNA liposomes mix | | Day 13 | |
| 72A | 4 | | | L055-SPLP/PBS mix | 72 h | Day 12 | |
| 72B | 4 | | | L055-SPLP/anti-luc siRNA liposomes mix | | Day 12 | |

36 male A/J mice (Jackson Laboratories) were seeded subcutaneously with Neuro 2A cells at a dose of $1.5 \times 10^6$ cells in a total volume of 50 µL phosphate buffered saline on day zero. Once tumors reached appropriate size (typically on day 9 or later), 200-240 µl PBS, SPLP, or SNALP formulations (100 µg nucleic acid total) prepared as described in Example 6 above, were administered intravenously. 24, 48, or 72 after administration of PBS, SPLP or a mixture of SPLP and SNALP, mice were sacrificed and organs (e.g., liver, lung, spleen, kidney, heart) and tumors were collected and evaluated for luciferase activity.

Co-administration of pL055 SPLP and anti-luc siRNA SNALP (both containing PEG-A-DMA) maximally decreases luciferase gene expression by 40% forty-eight hours after a single iv dose. The results are shown in FIGS. 9-13.

Example 6

Uptake of SPLP Comprising PEG-DAA Conjugates

This example illustrates the uptake of SPLP comprising PEG-DAA conjugates by mammalian cells in vitro. The SPLP formulations set forth in the table below were labeled with $^3$H-CHE and incubated on the cells at either 4° C. or 37° C. for 24 hours. The SPLP comprised either 2, 4, or 10 mol % PEG-C-DMA.

| | Mol % (DSPC:Chol:PEG-C-DMA:DODMA) |
|---|---|
| A | 20:50:10:15 |
| B | 20:61:4:15 |
| C | 20:63:2:15 |

Figure 14:
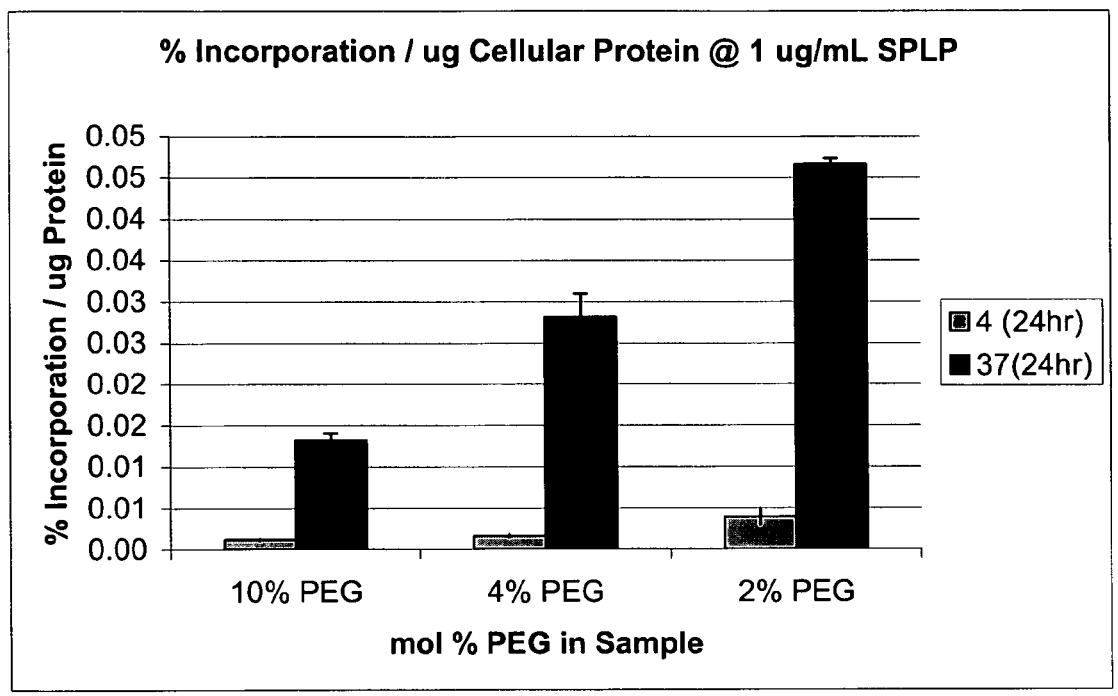
FIG. 14 illustrates data demonstrating uptake of SPLP comprising PEG-C-DMA conjugates by cells.

Uptake of SPLP occurred with greater efficiency at 37° C. and with decreasing amounts of PEG-C-DMA. The data is illustrated in FIG. 14.

Example 7

Biodistribution and Blood Clearance of SPLP Comprising PEG-DAA Conjugates

This example illustrates the biodistribution and blood clearance of SPLP comprising PEG-DAA conjugates. $^3$H-CHE-labeled SPLP comprising either PEG-C-DMA or PEG-C-DSA were administered intravenously to Neuro-2a tumor-bearing male A/J mice. SPLP were formulated as follows:

| Group | Treatment | Mol % (DSPC:Chol:PEG-C-DMA:Cationic Lipid) |
|---|---|---|
| A | SPLP (15 mol % PEG-C-DMA) | 20:50:15:15 |

| Group | Treatment | Mol % (DSPC:Chol:PEG-C-DMA:Cationic Lipid) |
|---|---|---|
| B | SPLP (10 mol % PEG-C-DMA) | 20:55:10:15 |
| C | SPLP (5 mol % PEG-C-DMA) | 20:60:5:15 |

Figure 15:
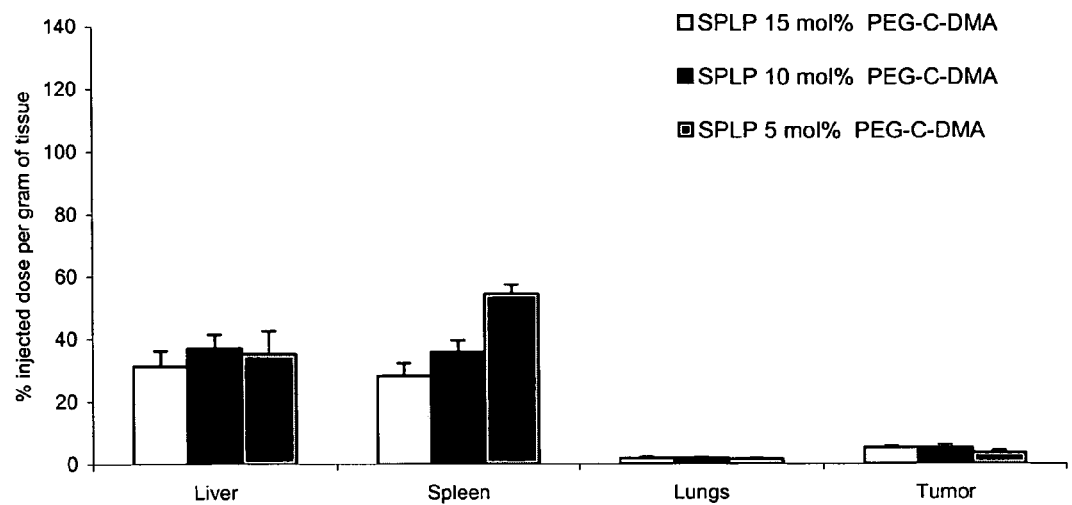
FIG. 15 illustrates data demonstrating the biodistribution of SPLP and SNALP comprising PEG-C-DMA or PEG-C-DSA in Neuro-2a tumor bearing male A/J mice 24 hours after administration of the SPLP or SNALP.

Biodistribution of SPLP in liver, spleen, lungs, and tumor was determined 48 hrs after SPLP administration. The results are shown in FIG. 15.

Figure 16:
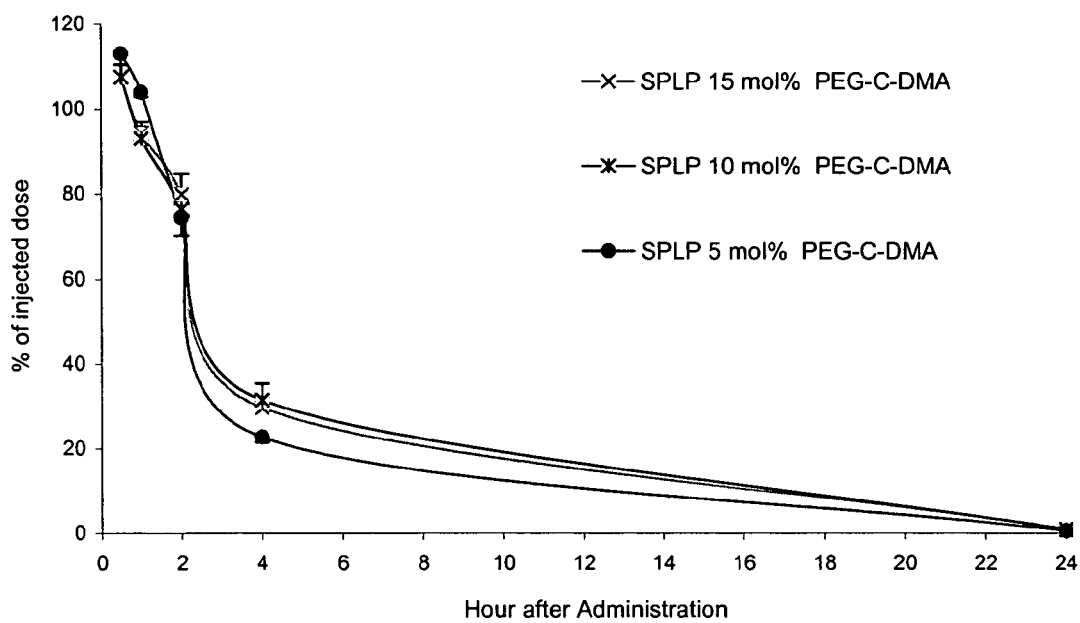
FIG. 16 illustrates data demonstrating the blood clearance of SPLP comprising PEG-C-DMA male A/J mice up to 24 hours after administration of the SPLP.

Blood clearance of SPLP was determined 1, 2, 4, and 24 hours after SPLP administration. The results are shown in FIG. 16.

Example 8

Biodistribution and Blood Clearance of SPLP and SNALP Comprising PEG-DAA Conjugates This example illustrates the biodistribution and blood clearance of SPLP and SNALP comprising PEG-DAA conjugates. $^3$H-CHE-labeled SPLP or SNALP comprising either PEG-C-DMA or PEG-C-DSA were administered intravenously to Neuro-2a tumor-bearing male A/J mice. SPLP comprised an encapsulated plasmid encoding luciferase and SNALP comprised an encapsulated an anti-luciferase siRNA sequence. The SPLP and SNALP formulations all had the following lipid ratios: DSPC 20%: Cholesterol 55%: PEG-Lipid 10%: DODMA 15%.

Figure 17:
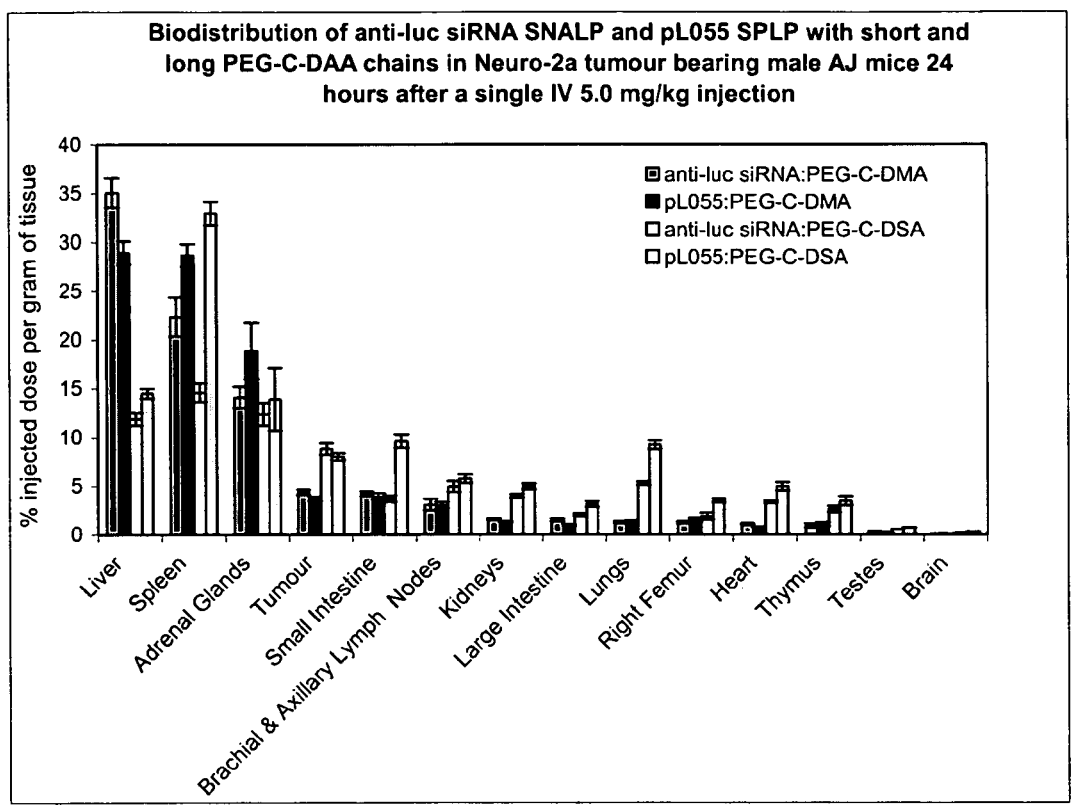
FIG. 17 illustrates data demonstrating the biodistribution of SPLP and SNALP comprising PEG-C-DMA in Neuro-2a tumor bearing male A/J mice 48 hours after administration of the SPLP or SNALP.

Biodistribution of SPLP or SNALP in liver, spleen, adrenal glands, tumor, small intestine, lymph nodes, kidneys, large intestine, femur, heart, thymus, testes, and brain was determined 24 hrs after administration of SPLP or SNALP. The results are shown in FIG. 17.

Figure 18:
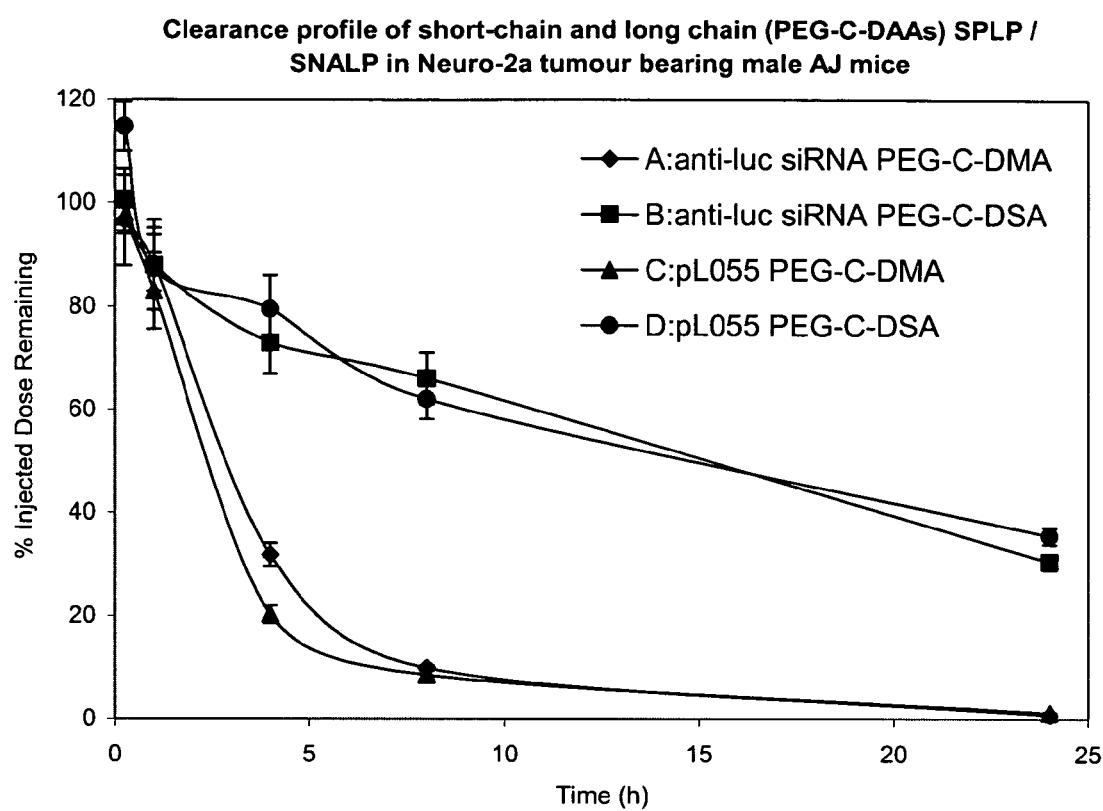
FIG. 18 illustrates data demonstrating the blood clearance of SPLP and SNALP comprising PEG-C-DMA or PEG-C-DSA in male A/J mice up to 24 hours after administration of the SPLP and SNALP.

Blood clearance of SPLP and SNALP comprising PEG-C-DMA or PEG-C-DSA was determined 1, 2, 4, 8, and 24 hours after administration of the SPLP and SNALP. The results are shown in FIG. 18.

Example 9

Transfection of Cells by SPLP and pSPLP Comprising PEG-DAA Conjugates

This example describes three separate experiments conducted to assess gene expression in organs and tumors following in vivo transfection with various SPLP formulations encapsulating a plasmid encoding luciferase under the control of the CMV promoter.

The first experiment assessed luciferase gene expression in Neuro2A tumor bearing male A/J mice after intravenous administration of SPLP and pSPLP. Formulations comprising C14 and C18 PEG-C-DAAs were compared to the equivalent PEG-DAGs. The PEG moieties had a molecular weight of 2000 daltons. DODMA was used as the cationic lipid in the SPLP. Either POPG or DOP was used as the anionic lipid in the pSPLP. The SPLP and pSPLP were formulated as follows:

| | Sample Description, (PEG-Lipid type, Charged Lipid type) | Mol % (DSPC:Chol:PEG-Lipid:Charged Lipid) |
|---|---|---|
| A | SPLP (PEG-DSG, DODMA) | 20:50:15:15 |
| B | SPLP (PEG-DMG, DODMA) | 20:55:10:15 |
| C | SPLP (PEG-C-DSA, DODMA) | 20:60:5:15 |
| D | SPLP (PEG-C-DMA, DODMA) | 20:62.5:2.5:15 |
| E | pSPLP (PEG-C-DSA, POPG) | 20:55:10:15 |
| F | pSPLP (PEG-C-DSA, DOP) | 20:60:5:15 |
| G | pSPLP (PEG-DSG, POPG) | 20:62.5:2.5:15 |

Figure 19:
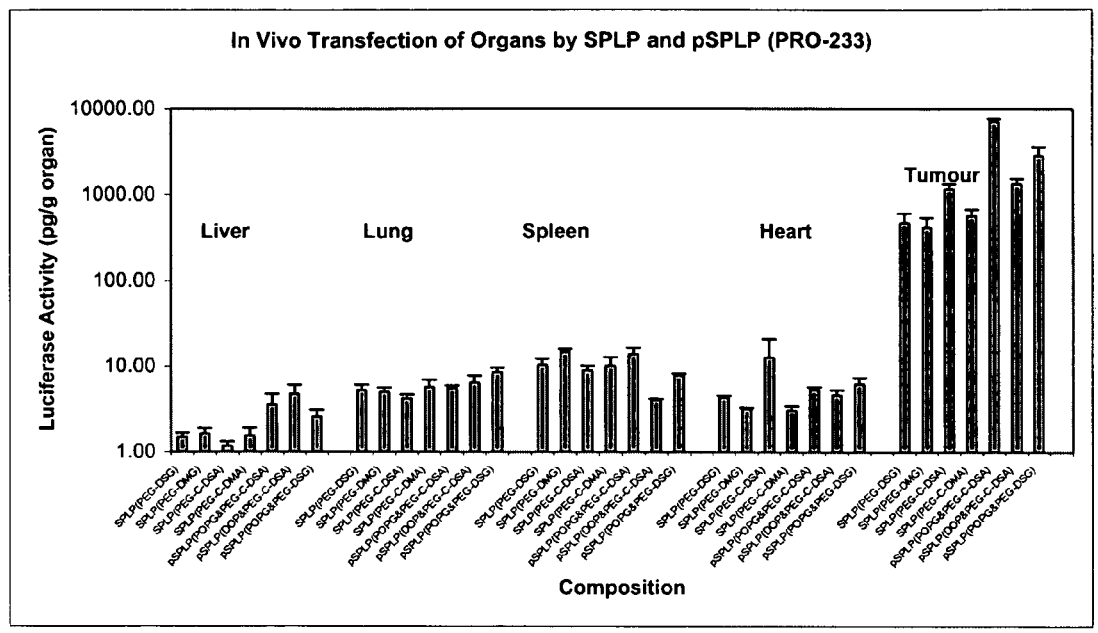
FIG. 19 illustrates data demonstrating in vivo transfection by SPLP and pSPLP comprising PEG-DAA conjugates and PEG-DAG conjugates and encapsulating a plasmid encoding luciferase.

Luciferase gene expression was measured in liver, lung, spleen, heart, and tumors 48 hours after intravenous administration of SPLP and pSPLP. Luciferase expression was highest in tumors relative to other tissue types for all SPLP and pSPLP formulations tested. The results are shown in FIG. 19.

The second experiment assessed luciferase gene expression in Neuro2A tumor bearing male A/J mice after intravenous administration of SPLP comprising varying percentages (i.e., 15%, 10%, 5%, or 2.5%) of PEG-C-DMA.

| | Mol % (DSPC:Chol:PEG-C-DMA:DODMA) |
|---|---|
| A | 20:50:15:15 |
| B | 20:55:10:15 |
| C | 20:60:5:15 |
| D | 20:62.5:2.5:15 |

Figure 20:
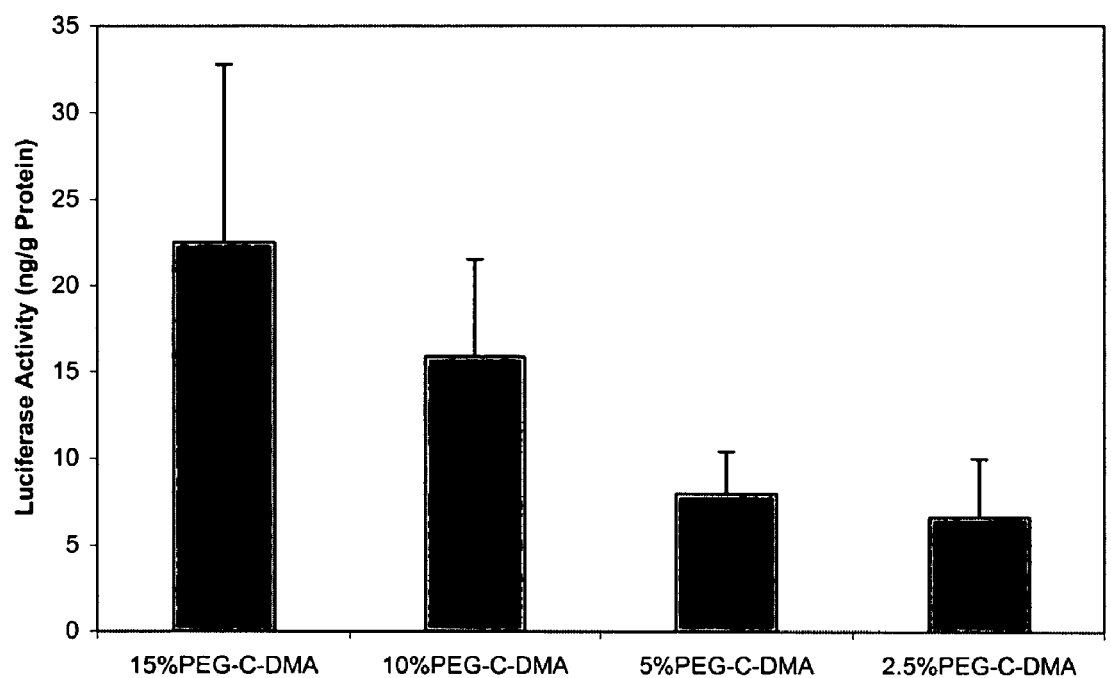
FIG. 20 illustrates data demonstrating in vivo transfection by SPLP comprising PEG-C-DMA conjugates and encapsulating a plasmid encoding luciferase.

Luciferase expression in tumors was measured 48 hours after administration of SPLP. The results are shown in FIG. 20.

The third set of experiments assessed luciferase gene expression in Neuro2A tumor bearing male A/J mice after intravenous administration of SPLP comprising PEG-C-DMA conjugates with various sizes of PEG moieties (i.e., 2000 or 750 daltons).

| | Sample Description |
|---|---|
| A | SPLP-PEG$_{2000}$-C-DMA (CHOL:DSPC:DODMA:PEG$_{2000}$-C-DMA 55:20:15:10 mol %) |
| B | SPLP-PEG$_{750}$-C-DMA/DODMA (CHOL:DSPC:DODMA:PEG$_{750}$-C-DMA 55:20:15:10 mol %) |
| C | SPLP-High PEG$_{750}$-C-DMA (CHOL:DSPC:DODMA:PEG$_{750}$-C-DMA 50:20:15:15 mol %) |
| D | SPLP-DODAC (CHOL:DSPC:DODMA:PEG$_{2000}$-C-DMA:DODAC 45:20:15:10:10 mol %) 0.35 mg/ml |

Figure 21:
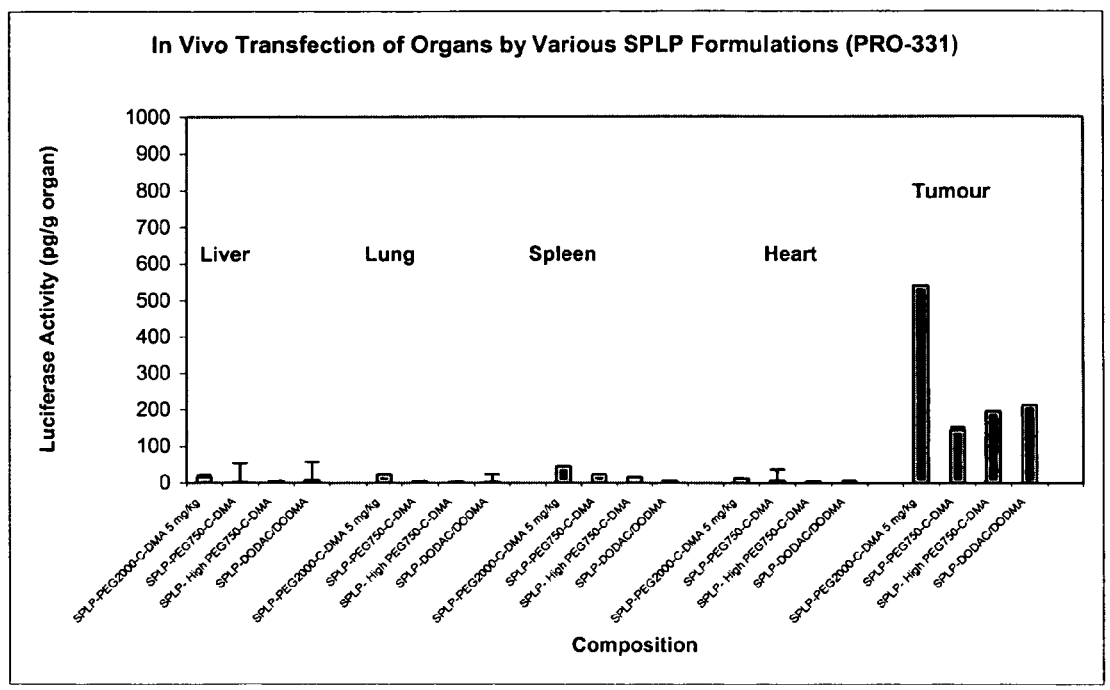
FIG. 21 illustrates data demonstrating in vivo transfection by SPLP comprising PEG-C-DMA conjugates and encapsulating a plasmid encoding luciferase.

Luciferase gene expression was measured in liver, lung, spleen, heart, and tumors 48 hours after administration of SPLP. Luciferase expression was highest in tumors relative to other tissue types for all SPLP formulations tested. The results are shown in FIG. 21.

Example 10

In Vitro Silencing of Gene Expression with SNALPs Comprising PEG-DAA Conjugates This example describes in vitro silencing of gene expression following delivery of SNALP encapsulating siRNA. Neuro2A-G cells expressing luciferase were contacted with SNALP formulations encapsulating anti-luciferase siRNA (i.e., siRNA comprising the following sequence: GAUUAUGUCCGGUUAUGUAUU (SEQ ID NO:1) and targeting the DNA sequence: GATTATGTCCGGTTATGTATT (SEQ ID NO:2)) for 48 hours in the presence or absence of chloroquine. The SNALP formulations contained varying amounts of PEG-C-DMA ($C_{14}$), i.e., 1%, 2%, 4%, or 10%. The cationic lipid was DODMA.

| Group | Treatment | Mol % (DSPC:Chol:PEG-C-DAA:DODMA) |
|---|---|---|
| A | PBS | — |
| B | Naked siRNA | — |
| C | SNALP (PEG-C-DMA) | 20:40:10:30 |
| D | SNALP (PEG-C-DMA) | 20:46:4:30 |
| E | SNALP (PEG-C-DMA) | 20:48:2:30 |
| F | SNALP (PEG-C-DMA) | 20:49:1:30 |

Figure 22:
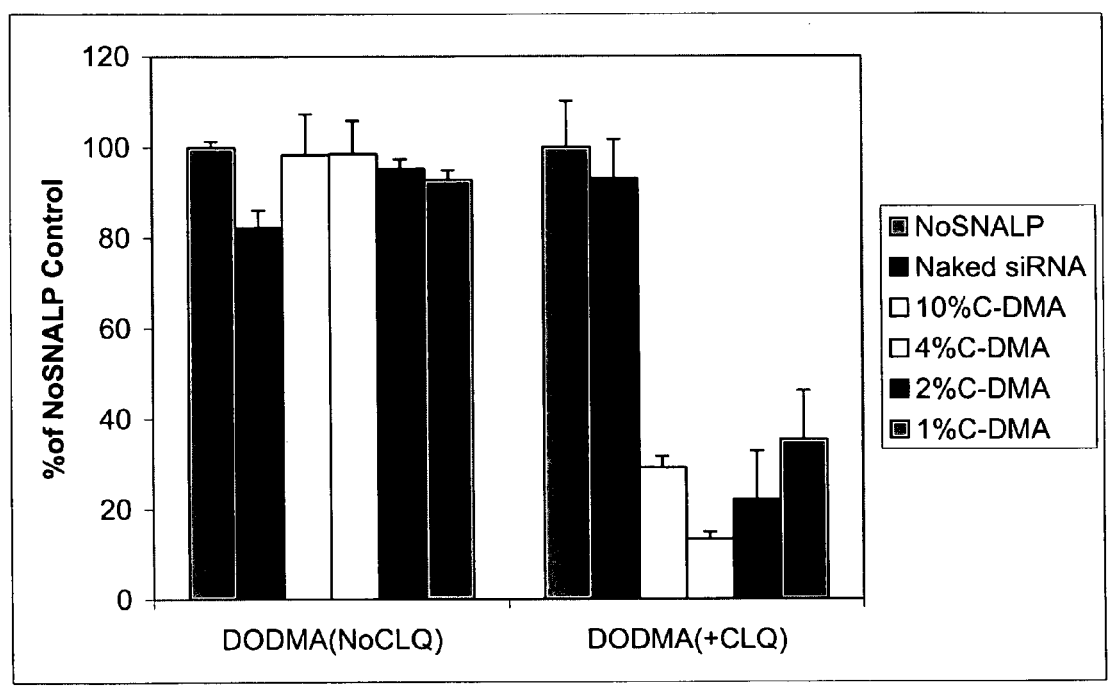
FIG. 22 illustrates data demonstrating silencing of luciferase expression in Neuro-2a cells contacted with SNALPs comprising a PEG-C-DMA conjugate and containing anti-luciferase siRNA.

The results are shown in FIG. 22.

Example 11

In Vivo Silencing of Gene Expression with SNALPs Comprising PEG-DAA Conjugates This example describes an experiment that demonstrates in vivo silencing of gene expression following administration of SNALP encapsulating siRNA.

Figure 23:
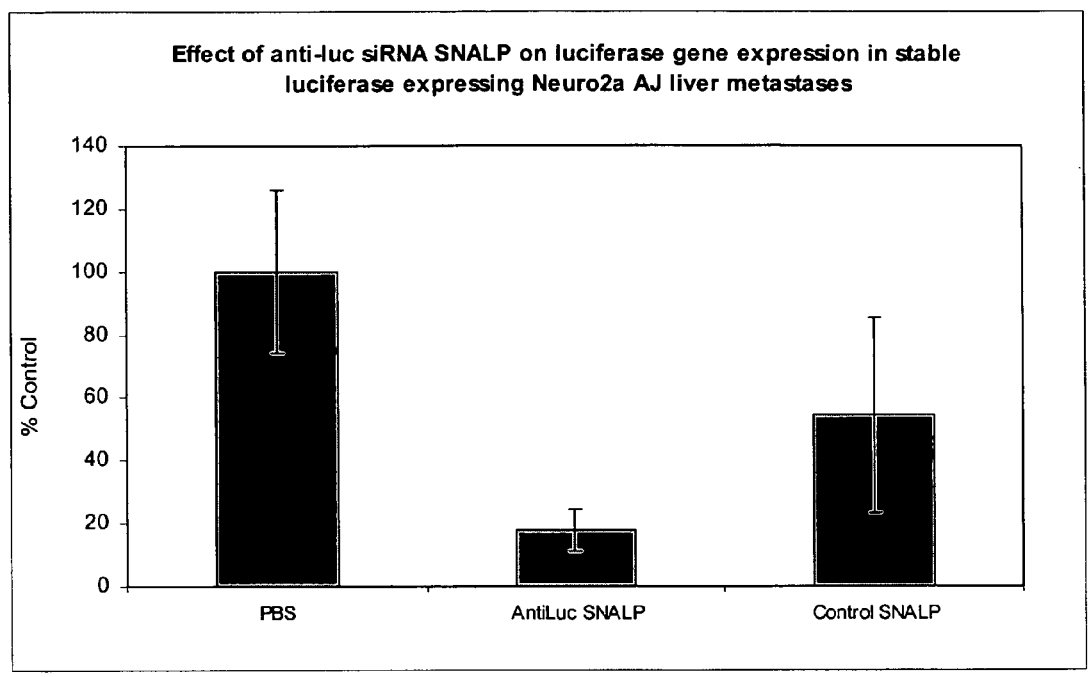
FIG. 23 illustrates in vivo data demonstrating silencing of luciferase expression in metastatic Neuro-2a tumors in male A/J mice expressing luciferase and treated SNALPs comprising a PEG-C-DMA conjugate and encapsulating anti-luciferase siRNA.

The experiment demonstrates that administration of SNALP encapsulating siRNA can silence gene expression in metastatic tumors. Neuro-2a tumor bearing male A/J mice expressing luciferase with metastatic liver tumors were treated with SNALPs comprising a PEG-DAA conjugate and encapsulating anti-luciferase siRNA (i.e., siRNA comprising the following sequence: GAUUAUGUCCGGUUAUGUAUU (SEQ ID NO:1) and targeting the DNA sequence: GATTATGTCCGGTTATGTATT (SEQ ID NO:2)). All SNALPs had the following formulation: DSPC 20% : Cholesterol 55% : PEG-C-DMA 10% : DODMA 15%. Mice received a single intravenous administration of SNALP. Luciferase expression in the tumors was determined 48 hours after SNALP injection. The results demonstrate that administration of SNALP can silence gene expression in vivo at a site distal to the site of SNALP administration. These results are shown in FIG. 23.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents and PCT publications, are incorporated herein by reference for all purposes.

---

What is claimed is:

1. A compound of Formula I:

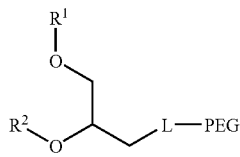

(I)

wherein:
$R^1$ and $R^2$ are independently selected and are alkyl groups having from about 10 to about 20 carbon atoms;
PEG is a polyethyleneglycol, wherein the terminal hydroxyl group is substituted with a methyl group; and
L is a carbamate linker moiety.

2. The compound in accordance with claim 1, wherein $R^1$ and $R^2$ are selected from the group consisting of lauryl (C12), myristyl (C14), palmityl (C16), stearyl (C18) and icosyl (C20).

3. The compound in accordance with claim 1, wherein $R^1$ and $R^2$ are the same.

4. The compound in accordance with claim 3, wherein $R^1$ and $R^2$ are both myristyl (C14).

5. The compound in accordance with claim 3, wherein $R^1$ and $R^2$ are both palmityl (C16).

6. The compound in accordance with claim 3, wherein $R^1$ and $R^2$ are both stearyl (C18).

7. The compound in accordance with claim 1, wherein said alkyl groups are saturated.

8. The compound in accordance with claim 1, wherein said alkyl groups are unsaturated.

9. The compound in accordance with claim 1, wherein said PEG has an average molecular weight ranging from about 550 daltons to about 10,000 daltons.

10. The compound in accordance with claim 9, wherein said PEG has an average molecular weight ranging from about 750 to about 5,000 daltons.

11. The compound in accordance with claim 9, wherein said PEG has an average molecular weight ranging from about 1,000 to about 5,000 daltons.

12. The compound in accordance with claim 9, wherein said PEG has an average molecular weight ranging from about 1,500 to about 3,000 daltons.

13. The compound in accordance with claim 9, wherein said PEG has an average molecular weight of about 2,000 daltons.

14. The compound in accordance with claim 1, having the formula

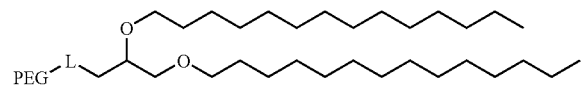

wherein PEG is a polyethyleneglycol, wherein the terminal hydroxyl group is substituted with a methyl group.

15. The compound in accordance with claim 14, wherein L has a formula selected from the group consisting of:

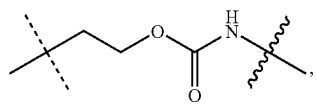

wherein the dashed line indicates the point of attachment to the PEG terminal oxygen and the wavy line indicates the point of attachment to the rest of the compound.

* * * * *